US009289465B2

(12) United States Patent
Kurihara et al.

(10) Patent No.: US 9,289,465 B2
(45) Date of Patent: Mar. 22, 2016

(54) IMMUNITY-INDUCING AGENT

(75) Inventors: Akira Kurihara, Kamakura (JP); Fumiyoshi Okano, Kamakura (JP)

(73) Assignee: TORAY INDUSTRIES, INC., Tokyo (JP)

( * ) Notice: Subject to any disclaimer, the term of this patent is extended or adjusted under 35 U.S.C. 154(b) by 0 days.

(21) Appl. No.: 13/391,595

(22) PCT Filed: Sep. 2, 2010

(86) PCT No.: PCT/JP2010/064993

§ 371 (c)(1), (2), (4) Date: Mar. 9, 2012

(87) PCT Pub. No.: WO2011/027807

PCT Pub. Date: Mar. 10, 2011

(65) Prior Publication Data

US 2012/0177673 A1 Jul. 12, 2012

(30) Foreign Application Priority Data

Sep. 3, 2009 (JP) ................................ 2009-203489

(51) Int. Cl.

| | |
|---|---|
| ***A61K 38/00*** | (2006.01) |
| ***A61K 39/00*** | (2006.01) |
| ***A61P 35/00*** | (2006.01) |
| ***G01N 33/53*** | (2006.01) |
| ***A61K 38/16*** | (2006.01) |
| ***A61K 35/17*** | (2015.01) |

(52) U.S. Cl.

CPC ................ *A61K 38/16* (2013.01); *A61K 35/17* (2013.01); *A61K 39/0011* (2013.01)

(58) Field of Classification Search

None

See application file for complete search history.

(56) References Cited

U.S. PATENT DOCUMENTS

| | | | | |
|---|---|---|---|---|
| 7,842,467 | B1 * | 11/2010 | Heidbrink et al. | 435/7.1 |
| 2003/0215809 | A1 * | 11/2003 | Sun et al. | 435/6 |
| 2004/0249144 | A1 * | 12/2004 | Sun et al. | 536/23.5 |

FOREIGN PATENT DOCUMENTS

| | | | |
|---|---|---|---|
| JP | 2008-534008 | A | 8/2008 |
| WO | WO 02/081641 | A2 | 10/2002 |
| WO | WO 03/029421 | A2 * | 4/2003 |
| WO | WO 2006/109943 | A1 | 10/2006 |
| WO | WO 2009/090651 | A2 | 7/2009 |

OTHER PUBLICATIONS

Lerner et al. 'Tapping the immunological repertoire to produce antibodies of predetermined specificity.' Nature 299:593-596, 1982.*

Ngo et al. 'Computational Complexity, Protein Structure Prediction, and the Levinthal Paradox'. The Protein Folding Problem and Tertiary Structure Prediction. Ed. K. Merz and S. Le Grand. Boston: Birkhauser, 491-495, 1994.*

Skolnick et al. 'From genes to protein strucJ, i~e and function: novel applications of computational approaches in the genomic era.' Trends in Biotech. 18:34-39, 2000.*

Attwood et al. The Babel of Bioinformatics. Science. 290(5491):471-473, 2000.*

International Search Report for PCT/JP2010/064993 dated Oct. 1, 2010.

Kumar, et al. "SCC-12, a novel cell cycle-regulated molecule, exhibits reduced expression in human renal carinomas", GENE, vol. 328, pp. 187-196, Mar. 17, 2004.

Losada, et al, "Functional contribution of Pds5 to cohesin-mediated cohesion in human cells and Xenopus egg extracts", Journal of Cell Science, vol. 118, No. 10, pp. 2133-2141, 2005, USA.

Sahin et al., "Human neoplasms elicit multiple specific immune responses in the autologous host", Proc. Natl. Acad. Sci., vol. 92, pp. 11810-11813, Dec. 1995, USA.

van der Bruggen, et al. "A gene encoding an antigen recognized by cytolytic T lymphocytes on a human melanoma," Dec. 1991, Science, vol. 254, 5038, pp. 1643-1647. (Abstract Only).

Zheng et al. "SCC-112 gene is involved in tumor progression and promotes the cell proliferation in G2/M phase—J Cancer Res Clin Oncol.", Apr. 2008, pp. 453-462. (Abstract Only).

Extended European Search Report for European Application No. 10813755.5, dated Mar. 15, 2013.

Zheng et al. "SCC-112 gene is involve | in tumor progression and promotes the cell proliferation in G2/M phase"—J Cancer Res Clin Oncol., vol. 134, Apr. 2008, pp. 453-462.

* cited by examiner

*Primary Examiner* — Nora Rooney

(74) *Attorney, Agent, or Firm* — Birch, Stewart, Kolasch & Birch, LLP

(57) ABSTRACT

An immunity-inducing agent comprising as an effective ingredient(s) a polypeptide(s) selected from the polypeptides: (a) a polypeptide consisting essentially of not less than 7 consecutive amino acids in any one of the amino acid sequences shown in SEQ ID NOs:2, 4, 6, 8, 10, 12 and 44 in SEQUENCE LISTING; (b) a polypeptide having a sequence identity of not less than 90% with the polypeptide (a) and consisting essentially of not less than 7 amino acids; and (c) a polypeptide comprising the polypeptide (a) or (b) as a partial sequence thereof; which polypeptide(s) has/have an immunity-inducing activity/activities, or as an effective ingredient (s) a recombinant vector(s) which comprise(s) a polynucleotide(s) encoding the polypeptide(s) and is/are capable of expressing the polypeptide(s) in vivo, is useful as a therapeutic and/or prophylactic agent for cancer, and/or the like.

1 Claim, 9 Drawing Sheets

IMMUNITY-INDUCING AGENT

TECHNICAL FIELD

The present invention relates to a novel immunity-inducing agent useful as a therapeutic and/or prophylactic agent for cancer.

BACKGROUND ART

Cancer is the commonest cause for death among all of the causes for death, and therapies carried out therefor at present are mainly surgical treatment, which may be carried out in combination with radiotherapy and/or chemotherapy. In spite of the developments of new surgical methods and discovery of new anti-cancer agents in recent years, treatment results of cancers have not been improved very much at present except for some cancers. In recent years, by virtue of the development in molecular biology and cancer immunology, cancer antigens recognized by cytotoxic T cells reactive with cancers, as well as the genes encoding the cancer antigens, were identified, and expectations for antigen-specific immunotherapies have been raised.

In immunotherapy, in order to reduce side effects, it is necessary that the peptide or protein to be recognized as the antigen exist hardly in normal cells and exist specifically in cancer cells. In 1991, Boon et al. of Ludwig Institute in Belgium isolated a human melanoma antigen MAGE 1, which is recognized by CD8-positive T cells, by a cDNA-expression cloning method using an autologous cancer cell line and cancer-reactive T cells (Non-patent Document 1). Thereafter, the SEREX (serological identifications of antigens by recombinant expression cloning) method, wherein tumor antigens recognized by antibodies produced in the living body of a cancer patient in response to the cancer of the patient himself are identified by application of a gene expression cloning method, was reported (Patent Document 1, Non-patent Document 2), and several cancer antigens have been isolated by this method. Using a part of the cancer antigens as targets, clinical tests for cancer immunotherapy have started.

On the other hand, as in human, a number of tumors such as mammary gland tumor and squamous cell carcinoma are known in dogs and cats, and they rank high also in the statistics of diseases in dogs and cats. However, at present, no therapeutic agent, prophylactic agent or diagnostic agent exists which is effective for cancers in dogs and cats. Most of tumors in dogs and cats are realized by owners only after they advanced to grow bigger, and in many cases, it is already too late to visit a hospital to receive surgical excision of the tumor or administration of a human drug (an anticancer drug or the like), so that those dogs and cats often die shortly after the treatment. Under such circumstances, if therapeutic agents and prophylactic agents for cancer effective for dogs and cats become available, their uses for canine cancers are expected to be developed.

PDS5A (PDS5, regulator of cohesion maintenance, homolog A) is a protein also called SSC-112 which was identified as a cell cycle regulator involved in distribution of chromosomes, and reported to show higher expression in nasopharyngeal carcinoma, renal cancer, liver cancer and a certain type of breast cancer cells, compared to normal tissues (Patent Document 2, Non-patent Documents 3 to 5). It has been reported that the growth of cancer cells can be suppressed by suppressing expression of PDS5A in cancer cells using an antisense nucleic acid, ribozyme or siRNA against the PDS5A gene or using an antibody that specifically binds to the PDS5A protein, and that cancer cells can be induced to cause apoptosis by administering the full-length PDS5A protein or a partial peptide of the PDS5A protein (Patent Document 3). Further, in Patent Document 3, increase in the mRNA level of the PDS5A protein in cancer cells was confirmed. However, there is no report suggesting that the PDS5A protein and a partial peptide of the protein has an action to induce immunity against cancer cells and hence the protein and a partial peptide of the protein is useful for therapy or prophylaxis of cancer, and whether or not the PDS5A protein has a function as a marker that can be used for diagnosis of cancer has not been confirmed.

PRIOR ART DOCUMENTS

Patent Documents

[Patent Document 1] U.S. Pat. No. 5,698,396 B
[Patent Document 2] WO2006/109943
[Patent Document 3] WO2002/081641

Non-Patent Documents

[Non-patent Document 1] Science, 254: 1643-1647 (1991)
[Non-patent Document 2] Proc. Natl. Acad. Sci. USA, 92: 11810-11813 (1995)
[Non-patent Document 3] Gene. 17; 328: 187-96 (2004)
[Non-patent Document 4] J. Cell. Sci. 15; 118 (Pt 10): 2133-41 (2005)
[Non-patent Document 5] J. Cancer Res. Clin. Oncol.: 134 (4):453-62 (2008)

SUMMARY OF THE INVENTION

Problems to be Solved by the Invention

The present invention aims to discover a novel polypeptide useful for a therapeutic and/or prophylactic agent for cancer or useful for detection of cancer, to provide the polypeptide for use in an immunity-inducing agent or in detection of cancer

Means for Solving the Problems

By the SEREX method using a canine breast cancer-derived cDNA library and serum obtained from a tumor-bearing dog, the present inventors intensively studied to obtain a cDNA encoding a protein which binds to antibodies existing in the serum derived from a tumor-bearing living body, and, based on the cDNA, the canine PDS5 protein, a regulator of cohesion maintenance, homolog A (hereinafter also referred to as PDS5A), having the amino acid sequence shown in SEQ ID NO:2 was prepared. Further, based on human and murine homologous genes of the obtained gene, human PDS5A having the amino acid represented by SEQ ID NO:4 or 44 (SEQ ID NO:4 corresponds to a partial sequence of SEQ ID NO:44) and murine PDS5A having the amino acid sequence shown in SEQ ID NO:6 were prepared. The present inventors then discovered that that these PDS5A are specifically expressed in tissues or cells of breast cancer, brain tumor, esophagus cancer, lung cancer, renal cancer, colon cancer, perianal adenocarcinoma, neuroblastoma and leukemia. Further, the present inventors discovered that, by administration of these PDS5A to a living body, immunocytes against PDS5A can be induced in the living body, and a tumor in the living body expressing PDS5A can be regressed. Further, the present inventors discovered that a recombinant vector which can express a polynucleotide encoding the full-length PDS5A protein or a fragment thereof can induce an anti-tumor effect against cancer expressing PDS5A in the living body.

Further, the present inventors discovered that a partial peptide of PDS5A has a capacity to be presented by antigen-presenting cells, thereby allowing activation and growth of cytotoxic T cells specific to the peptide (immunity-inducing activity), and therefore that the peptide is useful for therapy and/or prophylaxis of cancer, and, further, that antigen-presenting cells which have contacted with the peptide and T cells which have contacted with the antigen-presenting cells are useful for therapy and/or prophylaxis of cancer, thereby completing the present invention.

Thus, the present invention has the following characteristics.

(1) An immunity-inducing agent comprising as an effective ingredients) at least one polypeptide selected from the polypeptides (a) to (c) below, the polypeptide(s) having an immunity-inducing activity/activities, or as an effective ingredient(s) a recombinant vector(s) which comprise(s) a polynucleotide(s) encoding the polypeptide(s) and is/are capable of expressing the polypeptide(s) in vivo:

(a) a polypeptide consisting essentially of not less than 7 consecutive amino acids in any one of the amino acid sequences shown in SEQ ID NOs:2, 4, 6, 8, 10, 12 and 44 in SEQUENCE LISTING;

(b) a polypeptide having a sequence identity of not less than 90% with the polypeptide (a) and consisting essentially of not less than 7 amino acids; and (c) a polypeptide comprising the polypeptide (a) or (b) as a partial sequence thereof.

(2) The immunity-inducing agent according to (1), wherein the polypeptide (b) has a sequence identity of not less than 95% with the polypeptide (a).

(3) The immunity-inducing agent according to (1), wherein each of the polypeptide(s) having an immunity-inducing activity/activities is a polypeptide consisting essentially of not less than 7 consecutive amino acids in any one of the amino acid sequences shown in SEQ ID NOs:2, 4, 6, 8, 10, 12 and 44, or a polypeptide comprising the polypeptide as a partial sequence thereof; or a polypeptide having the same amino acid sequence as a polypeptide consisting essentially of not less than 7 consecutive amino acids in any one of the amino acid sequences shown in SEQ ID NOs:2, 4, 6, 8, 10, 12 and 44 except that one or several amino acids are deleted, substituted and/or added, or a polypeptide comprising the polypeptide as a partial sequence thereof.

(4) The immunity-inducing agent according to (3), wherein each of the polypeptide(s) having an immunity-inducing activity/activities is a polypeptide having any one of the amino acid sequences shown in SEQ ID NOs:2, 4, 6, 8, 10, 12 and 44 in SEQUENCE LISTING.

(5) The immunity-inducing agent according to (3), wherein each of the polypeptide(s) having an immunity-inducing activity/activities is a polypeptide consisting essentially of not less than 7 consecutive amino acids in the region of aa111-140, aa211-240, aa248-278, aa327-357, aa459-522, aa909-972, aa959-1022, aa994-1057 or aa1018-1080 in any one of the amino acid sequences shown in SEQ ID NOs:2, 6, 8, 10, 12 and 44 in SEQUENCE LISTING, or a polypeptide comprising the polypeptide as a partial sequence thereof; or a polypeptide having the same amino acid sequence as a polypeptide consisting essentially of not less than 7 consecutive amino acids in the region of aa111-140, aa211-240, aa248-278, aa327-357, aa459-522, aa909-972, aa959-1022, aa994-1057 or aa1018-1080 in any one of the amino acid sequences shown in SEQ ID NOs:2, 6, 8, 10, 12 and 44 in SEQUENCE LISTING except that one or several amino acids are deleted, substituted and/or added, or a polypeptide comprising the polypeptide as a partial sequence thereof.

(6) The immunity-inducing agent according to (5), wherein each of the polypeptide(s) having an immunity-inducing activity/activities is a polypeptide having any one of the amino acid sequences shown in SEQ ID NOs:27 to 35 in SEQUENCE LISTING, or a polypeptide comprising the polypeptide as a partial sequence thereof and having 10 to 12 amino acid residues; or a polypeptide having the same amino acid sequence as a polypeptide having any one of the amino acid sequences shown in SEQ ID NOs:27 to 35 in SEQUENCE LISTING except that one or several amino acids are deleted, substituted and/or added, or a polypeptide comprising the polypeptide as a partial sequence thereof and having 10 to 12 amino acid residues.

(7) The immunity-inducing agent according to any one of (1) to (6), for prophylaxis of a cancer in an animal.

(8) The immunity-inducing agent according to (5) or (6), for therapy of a cancer in an animal.

(9) The immunity-inducing agent according to (7) or (8), wherein the cancer is a cancer expressing PDS5A.

(10) The immunity-inducing agent according to any one of (7) to (9), wherein the cancer is breast cancer, brain tumor, esophagus cancer, lung cancer, renal cancer, colon cancer, perianal adenocarcinoma, neuroblastoma or leukemia.

(11) The immunity-inducing agent according to any one of (1) to (10), further comprising an immunoenhancer.

(12) An isolated antigen-presenting cell comprising a complex between the polypeptide having an immunity-inducing activity and an MHC molecule.

(13) An isolated T cell which selectively binds to a complex between the polypeptide having an immunity-inducing activity and an MHC molecule.

(14) A polypeptide having any one of the amino acid sequences shown in SEQ ID NOs:27 to 35 in SEQUENCE LISTING, or a polypeptide comprising the polypeptide as a partial sequence thereof and having 10 to 12 amino acid residues; or a polypeptide having the same amino acid sequence as a polypeptide having any one of the amino acid sequences shown in SEQ ID NOs:27 to 35 in SEQUENCE LISTING except that one or several amino acids are deleted, substituted and/or added, or a polypeptide comprising the polypeptide as a partial sequence thereof and having 10 to 12 amino acid residues, which polypeptide has an immunity-inducing activity.

(15) A method for detecting a cancer, the method comprising measurement of expression of a polypeptide having any one of the amino acid sequences shown in SEQ ID NOs:2, 4, 6, 8, 10, 12 and 44 in SEQUENCE LISTING or a polypeptide having a sequence identity of not less than 90% with the polypeptide, in a sample separated from a living body.

(16) A method for inducing immunity, the method comprising administering to an individual at least one polypeptide selected from the polypeptides (a) to (c) below, the polypeptide(s) having an immunity-inducing activity/activities, or a recombinant vector(s) which comprise(s) a polynucleotide(s) encoding the polypeptide(s) and is/are capable of expressing the polypeptide(s) in vivo:

(a) a polypeptide consisting essentially of not less than 7 consecutive amino acids in any one of the amino acid sequences shown in SEQ ID NOs:2, 4, 6, 8, 10, 12 and 44 in SEQUENCE LISTING;

(b) a polypeptide having a sequence identity of not less than 90% with the polypeptide (a) and consisting essentially of not less than 7 amino acids; and (c) a polypeptide comprising the polypeptide (a) or (b) as a partial sequence thereof.

Effect of the Invention

By the present invention, a novel immunity-inducing agent useful for therapy and/or prophylaxis and/or the like of cancer is provided. As particularly described in later-mentioned Examples, by administering the polypeptide used in the present invention to a living body, immunocytes can be induced in the living body, and a cancer which has already occurred can be reduced or regressed. Therefore, the polypeptide is useful for therapy and/or prophylaxis of cancer.

BRIEF DESCRIPTION OF THE DRAWINGS

In FIG. 12, the reference numerals 25 to 33 along the abscissa indicate the abilities of HLA-A0201-positive CD8-positive T cells to produce IFN-γ in response to stimulation by T2 cells pulsed with the respective peptides of SEQ ID NOs:27 to 35. The reference numeral 23 shows a result obtained when the above treatment was carried out without addition of a polypeptide, and the reference numeral 24 shows a result obtained when the above treatment was carried out with addition of the polypeptide shown in SEQ ID NO:36, which is outside the scope of the present invention.

In FIG. 13, the reference numerals 36 to 44 along the abscissa indicate the cytotoxic activities, against T98G cells, of HLA-A0201-positive CD8-positive T cells stimulated with the respective peptides of SEQ ID NOs:27 to 35. The reference numeral 34 shows the cytotoxic activity of CD8-positive T cells induced without addition of a polypeptide, and the reference numeral 35 shows the cytotoxic activity of CD8-positive T cells induced using a negative control peptide (SEQ ID NO:36).

BEST MODE FOR CARRYING OUT THE INVENTION

Figure 1:
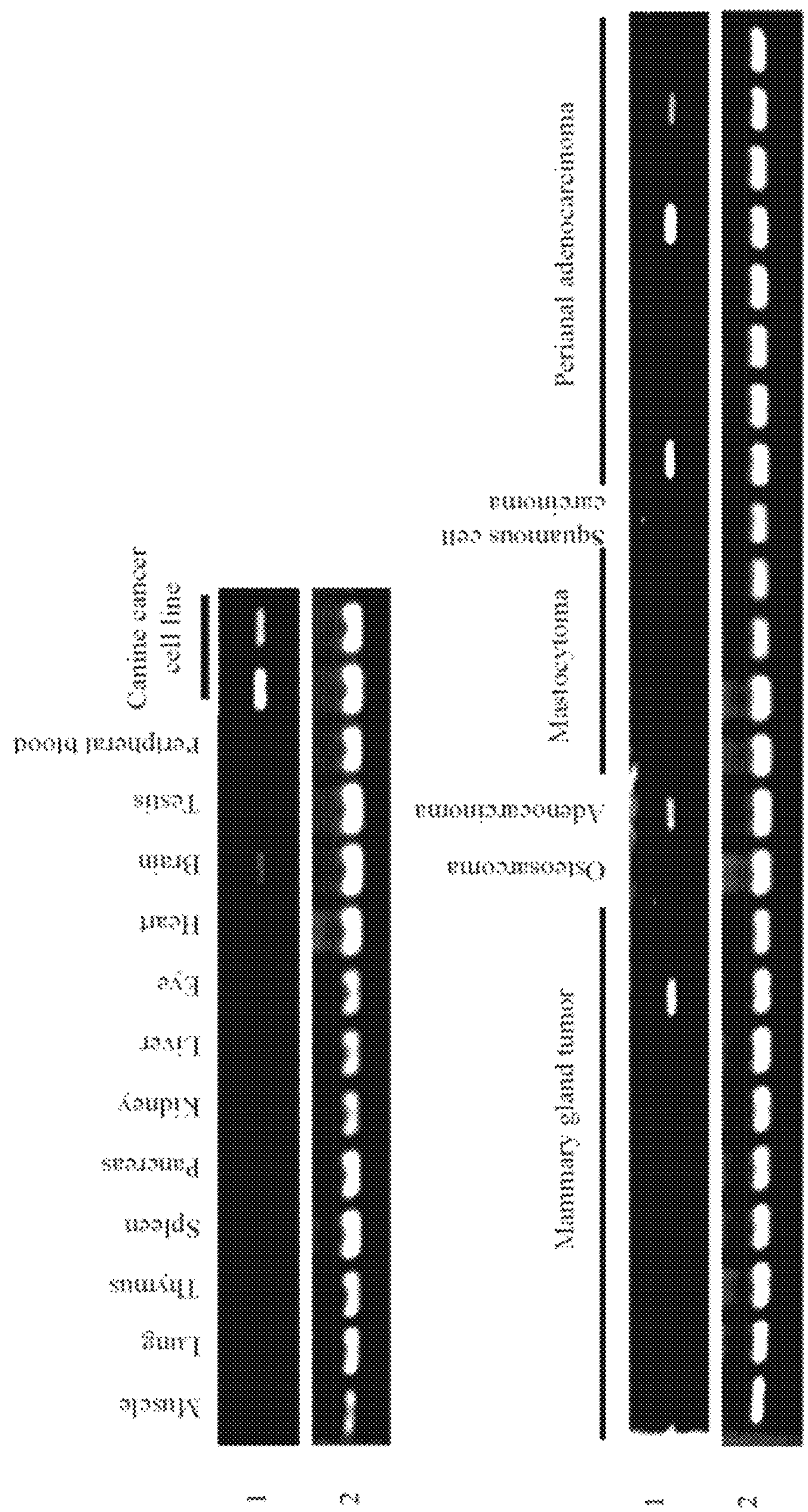
FIG. 1 shows the expression patterns of the identified PDS5A gene in canine normal tissues, tumor tissues and tumor cell lines. Reference numeral 1, the expression patterns of the canine PDS5A gene in various canine tissues and cell lines; reference numeral 2, the expression patterns of the canine GAPDH gene in various canine tissues and cell lines.

Examples of the polypeptide contained in the immunity-inducing agent of the present invention as an effective ingredient include the followings. In the present invention, the term "polypeptide" means a molecule formed by a plurality of amino acids linked together by peptide bonds, and includes not only polypeptide molecules having large numbers of amino acids constituting them, but also low-molecular-weight molecules having small numbers of amino acids (oligopeptides), and full-length proteins. In the present invention, the full-length PDS5A proteins having the amino acid sequences shown in SEQ ID NO:2, 4, 6, 8, 10, 12 and 44 are also included therein.

(a) A polypeptide which consists essentially of not less than 7 consecutive amino acids in a polypeptide having the amino acid sequence shown in SEQ ID NO:2, 4, 6, 8, 10, 12 or 44 in SEQUENCE LISTING, and has an immunity-inducing activity.

(b) a polypeptide which has a sequence identity of not less than 90% with the polypeptide (a), consists essentially of not less than 7 amino acids, and has an immunity-inducing activity.

(c) a polypeptide which comprises the polypeptide (a) or (b) as a partial sequence thereof, and has an immunity-inducing activity.

In the present invention, the term "having an amino acid sequence" means that amino acid residues are arrayed in such an order. Therefore, for example, "polypeptide having the amino acid sequence shown in SEQ ID NO:2" means the polypeptide having the amino acid sequence of Met Asp Phe Thr . . . (snip). Asp Leu Gln Arg shown in SEQ ID NO:2, which polypeptide has a size of 1337 amino acid residues. Further, for example, "polypeptide having the amino acid sequence shown in SEQ ID NO:2" may be abbreviated as "polypeptide of SEQ ID NO:2". This also applies to the term "having a base sequence". In this case, the term "having" may be replaced with the expression "essentially consisting of".

As used herein, the term "immunity-inducing activity" means an ability to induce immunocytes which secrete cytokines such as interferon in a living body.

Whether or not the polypeptide has an immunity-inducing activity can be confirmed using, for example, the known ELISPOT assay. More particularly, for example, as described in the Examples below, cells such as peripheral blood mononuclear cells are obtained from a living body to which a polypeptide whose immunity-inducing activity is to be evaluated was administered, which cells are then cocultured with the polypeptide, followed by measuring the amount(s) of a cytokine(s) produced by the cells using a specific antibody/antibodies, thereby measuring the number of immunocytes in the cells, which enables evaluation of the immunity-inducing activity.

Alternatively, as described in the later-mentioned Examples, when a recombinant polypeptide in any of (a) to (c) described above is administered to a tumor-bearing animal, the tumor can be regressed by its immunity-inducing activity. Thus, the above immunity-inducing activity can be evaluated also as an ability to suppress the growth of cancer cells or to cause reduction or disappearance of a cancer tissue (tumor) (hereinafter referred to as "anti-tumor activity"). The anti-tumor activity of a polypeptide can be confirmed by, for example, as more particularly described in the Examples below, observation of whether or not a tumor is reduced when the polypeptide was actually administered to a tumor-bearing living body.

Alternatively, the anti-tumor activity of a polypeptide can be evaluated also by observation of whether or not T cells stimulated with the polypeptide (that is, T cells brought into contact with antigen-presenting cells presenting the polypeptide) show a cytotoxic activity against tumor cells in vitro. The contact between the T cells and the antigen-presenting cells can be carried out by coculture of the both in a liquid medium, as mentioned below. Measurement of the cytotoxic activity can be carried out by, for example, the known method called $^{51}$Cr release assay described in Int. J. Cancer, 58: p 317, 1994. In cases where the polypeptide is to be used for therapy and/or prophylaxis of cancer, the evaluation of the immunity-inducing activity is preferably carried out using the anti-tumor activity as an index, although the index is not restricted.

The amino acid sequences shown in SEQ ID NOs:2, 4, 6, 8, 10, 12 and 44 in SEQUENCE LISTING are the amino acid sequences of the PDS5A proteins which were isolated, by the SEREX method using a canine testis-derived cDNA library and serum of a tumor-bearing dog, as a polypeptide that specifically binds to an antibody existing in the serum of the tumor-bearing dog and homologous factors of the polypeptide in human (SEQ ID NOs:4 and 44), mouse (SEQ ID NO:6), cow (SEQ ID NO:8), horse (SEQ ID NO:10) and chicken (SEQ ID NO:12) (see Example 1). Human PDS5A, which is a human homologous factor of canine PDS5A, has a sequence identity of 94% in terms of the base sequence and 99% in terms of the amino acid sequence; murine PDS5A, which is a murine homologous factor, has a sequence identity of 91% in terms of the base sequence and 99% in terms of the amino acid sequence; bovine PDS5A, which is a bovine homologous factor, has a sequence identity of 95% in terms of the base sequence and 99% in terms of the amino acid sequence; equine PDS5A, which is an equine homologous factor, has a sequence identity of 96% in terms of the base sequence and 99% in terms of the amino acid sequence; and chicken PDS5A, which is a chicken homologous factor, has a sequence identity of 83% in terms of the base sequence and 98% in terms of the amino acid sequence.

The polypeptide (a) is a polypeptide which consists essentially of not less than 7 consecutive, preferably 8, 9 or not less than 10 consecutive amino acids in the polypeptide having the amino acid sequence shown in SEQ ID NO:2, 4, 6, 8, 10, 12 or 44, and has an immunity-inducing activity. The polypeptide especially preferably has the amino acid sequence shown in SEQ ID NO:2, 4, 6, 8, 10, 12 or 44. As is known in the art, a polypeptide having not less than about 7 amino acid residues can exert its antigenicity and immunogenicity. Thus, a polypeptide having not less than 7 consecutive amino acid residues in the amino acid sequence shown in SEQ ID NO:2, 4, 6, 8, 10, 12 or 44 can have an immunity-inducing activity, so that it can be used for preparation of the immunity-inducing agent of the present invention.

As a principle of immune induction by administration of a cancer antigenic polypeptide, the following process is known: a polypeptide is incorporated into an antigen-presenting cell and then degraded into smaller fragments by peptidases in the cell, followed by presentation of the fragments on the surface of the cell. The fragments are then recognized by a cytotoxic T cell or the like, which selectively kills cells presenting the antigen. The size of the polypeptide presented on the surface of the antigen-presenting cell is relatively small and about 7 to 30 amino acids. Therefore, from the viewpoint of presenting thereof on the surface of the antigen-presenting cell, one preferred mode of the above-described polypeptide (a) is a polypeptide composed of about 7 to 30 consecutive amino acids in the amino acid sequence shown in SEQ ID NO:2, 4, 6, 8, 10, 12 or 44, and more preferably, a polypeptide composed of about 8 to 30 or about 9 to 30 amino acids is sufficient as the polypeptide (a). In some cases, these relatively small polypeptides are presented directly on the surface of the antigen-presenting cell without being incorporated into the antigen-presenting cells.

Further, since a polypeptide incorporated into an antigen-presenting cell is cleaved at random sites by peptidases in the cell to yield various polypeptide fragments, which are then presented on the surface of the antigen-presenting cell, administration of a large polypeptide such as the full-length region of SEQ ID NO:2, 4, 6, 8, 10, 12 or 44 inevitably causes production of polypeptide fragments by degradation thereof in the antigen-presenting cell, which fragments are effective for immune induction via the antigen-presenting cell. Therefore, also for immune induction via antigen-presenting cells, a large polypeptide can be preferably used, and the polypeptide may be composed of not less than 30, preferably not less than 100, more preferably not less than 200, still more preferably not less than 250 amino acids. The polypeptide may be still more preferably composed of the full-length region of SEQ ID NO:2, 4, 6, 8, 10, 12 or 44.

Further, the polypeptides of the present invention can be checked with a checking medium by which epitope peptides having binding motifs of various types of HLA and consisting essentially of 8 to 12, preferably 9 to 10 amino acids can be searched, for example, HLA Peptide Binding Predictions (http://bimas.dcrt.nih.gov/molbio/hla_bind/index.html) in Bioinformatics & Molecular Analysis Selection (BIMAS), to screen peptides which may be epitope peptides. More particularly, a polypeptide consisting essentially of not less than 7 consecutive amino acids in the region of amino acid residue positions aa111-140, aa211-240, aa248-278, aa327-357, aa459-522, aa909-972, aa959-1022, aa994-1057 or aa1018-1080 in the amino acid sequence shown in SEQ ID NO:2, 6, 8, 10, 12 or 44 is preferred, and, in the polypeptide of SEQ ID NO:4 or 44, the polypeptide shown in any of SEQ ID NOs:27 to 35, or a polypeptide which comprises a polypeptide having the amino acid sequence shown in any of SEQ ID NOs:27 to 35 as a partial sequence and has 10 to 12 amino acid residues is more preferred.

The polypeptide (b) is the same polypeptide as the polypeptide (a) except that a small number of (preferably, one or several) amino acid residues are substituted, deleted and/or inserted, which has a sequence identity of not less than 90%, preferably not less than 95%, more preferably not less than 98%, still more preferably not less than 99% or not less than 99.5% to the original sequence and has an immunity-inducing activity. It is well known in the art that, in general, there are cases where a protein antigen retains almost the same antigenicity as the original protein even if the amino acid sequence of the protein is modified such that a small number of amino acids are substituted, deleted and/or inserted. Therefore, since the polypeptide (b) may also exert an immunity-inducing activity, it can be used for preparation of the immunity-inducing agent of the present invention. Further, the polypeptide (b) is also preferably the same polypeptide as one having the amino acid sequence shown in SEQ ID NO:2, 4, 6, 8, 10, 12 or 44 except that one or several amino acid residues are substituted, deleted and/or inserted. As used herein, the term "several" means an integer of 2 to 10, preferably an integer of 2 to 6, more preferably an integer of 2 to 4.

As used herein, the term "sequence identity" of amino acid sequences or base sequences means the value calculated by aligning two amino acid sequences (or base sequences) to be compared such that the number of matched amino acid residues (or bases) is maximum between the amino acid sequences (or base sequences), and dividing the number of matched amino acid residues (or the number of matched bases) by the total number of amino acid residues (or the total number of bases), which value is represented as a percentage. When the alignment is carried out, a gap(s) is/are inserted into one or both of the two sequences to be compared as required. Such alignment of sequences can be carried out using a well-known program such as BLAST, FASTA or CLUSTAL W. When a gap(s) is/are inserted, the above-described total number of amino acid residues is the number of residues calculated by counting one gap as one amino acid residue. When the thus counted total number of amino acid residues is different between the two sequences to be compared, the sequence identity (%) is calculated by dividing the number of matched amino acid residues by the total number of amino acid residues in the longer sequence.

The 20 types of amino acids constituting naturally occurring proteins may be classified into groups in each of which similar properties are shared, for example, into neutral amino acids with side chains having low polarity (Gly, Re, Val, Leu, Ala, Met, Pro), neutral amino acids having hydrophilic side chains (Asn, Gln, Thr, Ser, Tyr, Cys), acidic amino acids (Asp, Glu), basic amino acids (Arg, Lys, His) and aromatic amino acids (Phe, Tyr, Trp). It is known that, in most cases, substitutions of amino acids within the same group do not change the properties of the polypeptide. Therefore, in cases where an amino acid residue(s) in the polypeptide (a) of the present invention is/are substituted, the probability that the immunity-inducing activity can be maintained may be increased by introducing the substitution(s) within the same group, which is preferred.

As the polypeptide (b), which corresponds to the above-described epitope peptide, a polypeptide which is the same as the polypeptide consisting essentially of not less than 7 consecutive amino acids in the region of aa111-140, aa211-240, aa248-278, aa327-357, aa459-522, aa909-972, aa959-1022, aa994-1057 or aa1018-1080 in any one of the amino acid sequences shown in SEQ ID NOs:2, 6, 8, 10, 12 and 44 except that one or several amino acids are deleted, substituted and/or added, or a polypeptide comprising the polypeptide as a partial sequence thereof and having an immunity-inducing activity is preferred, and, in the polypeptide of SEQ ID NO:4 or 44, a polypeptide which is the same as the polypeptide having the amino acid sequence shown in any of SEQ ID NOs:27 to 35 except that one or several amino acids are deleted, substituted and/or added, or a polypeptide comprising the polypeptide as a partial sequence and having 10 to 12 amino acid residues is more preferred.

The polypeptide (c) comprises the polypeptide (a) or (b) as a partial sequence and has an immunity-inducing activity. That is, the polypeptide (c) has another/other amino acid(s) or polypeptide(s) added at one or both ends of the polypeptide (a) or (b), and has an immunity-inducing activity. Such a polypeptide can also be used for preparation of the immunity-inducing agent of the present invention.

As the polypeptide (c), which corresponds to the above-described epitope, a polypeptide comprising as a partial sequence the polypeptide consisting essentially of not less than 7 consecutive amino acids in the region of aa111-140, aa211-240, aa248-278, aa327-357, aa459-522, aa909-972, aa959-1022, aa994-1057 or aa1018-1080 in any one of the amino acid sequences shown in SEQ ID NOs:2, 6, 8, 10, 12 and 44 is preferred, and, in the polypeptide of SEQ ID NO:4 or 44, a polypeptide comprising as a partial sequence: a polypeptide which is the same as the polypeptide having the amino acid sequence shown in any of SEQ ID NOs:27 to 35 except that one or several amino acids are deleted, substituted and/or added; or a polypeptide comprising the polypeptide as a partial sequence and having 10 to 12 amino acid residues; is more preferred.

The above-described polypeptides can be synthesized by, for example, a chemical synthesis method such as the Fmoc method (fluorenylmethyloxycarbonyl method) or the tBoc method (t-butyloxycarbonyl method). Further, they can be synthesized by conventional methods using various types of commercially available peptide synthesizers. Further, the polypeptide of interest can be obtained using known genetic engineering techniques, by preparing a polynucleotide encoding the above polypeptide and incorporating the polynucleotide into an expression vector, which is then introduced into a host cell, followed by allowing the polypeptide to be produced in the host cell.

The polynucleotide encoding the above polypeptide can be easily prepared by a known genetic engineering technique or a conventional method using a commercially available nucleic acid synthesizer. For example, DNA having the base sequence shown in SEQ ID NO:1 can be prepared by carrying out PCR using a canine chromosomal DNA or cDNA library as a template, and a pair of primers designed such that the base sequence shown in SEQ ID NO:1 can be amplified therewith. DNA having the base sequence of SEQ ID NO:3 or 43 can be similarly prepared by using a human chromosomal DNA or cDNA library as the template. The reaction conditions for the PCR can be set appropriately, and examples thereof include, but are not limited to, repeating the reaction process of 94° C. for 30 seconds (denaturation), 55° C. for 30 seconds to 1 minute (annealing) and 72° C. for 2 minutes (extension) for, for example, 30 cycles, followed by the reaction at 72° C. for 7 minutes. Further, the desired DNA can be isolated by preparing an appropriate probe(s) or primer(s) based on the information of the base sequences and the amino acid sequences shown in SEQ ID NO:1, 3, 5, 7, 9, 11 and 43 in SEQUENCE LISTING in the present specification, and screening a cDNA library of dog, human or the like using the probe(s) or primer(s). The cDNA library is preferably prepared from a cell, organ or tissue expressing the protein of SEQ ID NO:2, 4, 6, 8, 10, 12 or 44. The above-described operations such as preparation of a probe(s) or primer(s), construction of a cDNA library, screening of a cDNA library and cloning of a gene of interest are known to those skilled in the art, and can be carried out according to the methods described in Molecular Cloning, Second Edition; Current Protocols in Molecular Biology; and/or the like. From the thus obtained DNA, DNA encoding the polypeptide (a) can be obtained. Further, since the codons encoding each amino acid are known, the base sequence of a polynucleotide encoding a specific amino acid sequence can be easily specified. Therefore, since the base sequence of a polynucleotide encoding the polypeptide (b) or polypeptide (c) can also be easily specified, such a polynucleotide can also be easily synthesized using a commercially available nucleic acid synthesizer according to a conventional method.

The host cells are not restricted as long as those can express the above-described polypeptide, and examples thereof include, but are not limited to, prokaryotic cells such as *E. coli*; and eukaryotic cells such as mammalian cultured cells including monkey kidney cells COS1 and Chinese hamster ovary cells CHO; budding yeast; fission yeast; silkworm cells; and *Xenopus laevis* egg cells.

In cases where prokaryotic cells are used as the host cells, an expression vector in which an origin that enables replication of the vector in a prokaryotic cell, promoter, ribosome binding site, DNA cloning site, terminator and/or the like is/are contained is used. Examples of the expression vector for *E. coli* include the pUC system, pBluescriptII, pET expression system and pGEX expression system. By incorporating a DNA encoding the above polypeptide into such an expression vector and transforming prokaryotic host cells with the vector, followed by culturing the resulting transformants, the polypeptide encoded by the DNA can be expressed in the prokaryotic host cells. In this process, the polypeptide can also be expressed as a fusion protein with another protein.

In cases where eukaryotic cells are used as the host cells, an expression vector for eukaryotic cells having a promoter, splicing site, poly(A) addition site and/or the like is used as the expression vector. Examples of such an expression vector include pKA1, pCDM8, pSVK3, pMSG, pSVL, pBK-CMV, pBK-RSV, EBV vector, pRS, pcDNA3, pMSG and pYES2. In the same manner as described above, by incorporating a DNA encoding the above polypeptide into such an expression vector and transforming eukaryotic host cells with the vector, followed by culturing the resulting transformants, the polypeptide encoded by the DNA can be expressed in the eukaryotic host cells. In cases where pIND/V5-His, pFLAG-CMV-2, pEGFP-N1, pEGFP-C1 or the like is used as the expression vector, the above polypeptide can be expressed as a fusion protein wherein a tag such as a His tag, FLAG tag, myc tag, HA tag or GFP was added.

For the introduction of the expression vector into the host cells, a well-known method such as electroporation, the calcium phosphate method, the liposome method or the DEAE dextran method may be used.

Isolation and purification of the polypeptide of interest from the host cells can be carried out by a combination of known separation operations. Examples of the known separation operations include, but are not limited to, treatment with a denaturant such as urea or with a surfactant; ultrasonication treatment; enzyme digestion; salting-out or solvent fractional precipitation; dialysis; centrifugation; ultrafiltration; gel filtration; SDS-PAGE; isoelectric focusing; ion-exchange chromatography; hydrophobic chromatography; affinity chromatography; and reversed-phase chromatography.

The polypeptides obtained by the above method also include, as mentioned above, those in the form of a fusion protein with another arbitrary protein. Examples thereof include fusion proteins with glutathion S-transferase (GST) and with a His tag. Such a polypeptide in the form of a fusion protein is also included within the scope of the present invention as the above-described polypeptide (c). Further, in some cases, a polypeptide expressed in a transformed cell is modified in various ways in the cell after translation. Such a post-translationally modified polypeptide is also included within the scope of the present invention as long as it has an immunity-inducing activity. Examples of such a post-translational modification include: elimination of N-terminal methionine; N-terminal acetylation; glycosylation; limited degradation by an intracellular protease; myristoylation; isoprenylation; and phosphorylation.

As described more particularly in the later-mentioned Examples, by administration of the polypeptide having an immunity-inducing activity or an expression vector comprising the gene encoding the polypeptide to a tumor-bearing living body, an already existing tumor can be regressed. Further, by administration of the polypeptide having an immunity-inducing activity or the gene encoding the polypeptide to a living body before occurrence of cancer, development of a tumor can be prevented. Therefore, the immunity-inducing agent of the present invention can be used as a therapeutic and/or prophylactic agent for cancer. Further, the polypeptide having an immunity-inducing activity can be used for a method of therapy and/or prophylaxis of cancer by immune induction.

As used herein, the terms “tumor” and “cancer” mean a malignant neoplasm, and are used interchangeably In this case, the cancer to be treated is not restricted as long as PDS5A is expressed in the cancer, and the cancer is preferably breast cancer, brain tumor, esophagus cancer, lung cancer, renal cancer, colon cancer, perianal adenocarcinoma, neuroblastoma or leukemia.

The subject animal is preferably a mammal, more preferably a mammal such as a primate, pet animal, domestic animal or sport animal, especially preferably human, dog or cat.

The administration route of the immunity-inducing agent of the present invention to a living body may be either oral administration or parenteral administration, and is preferably parenteral administration such as intramuscular administration, subcutaneous administration, intravenous administration or intraarterial administration. In cases where the immunity-inducing agent is used for therapy of cancer, it may be administered to a regional lymph node in the vicinity of the tumor to be treated, as described in the Examples below, in order to enhance its anticancer activity. The dose may be any dose as long as the dose is effective for immune induction, and, for example, in cases where the agent is used for therapy and/or prophylaxis of cancer, the dose may be one effective for therapy and/or prophylaxis of the cancer. The dose effective for therapy and/or prophylaxis of cancer is appropriately selected depending on the size and symptoms of the tumor and the like, and the effective dose is usually, 0.0001 μg to 1000 μg, preferably 0.001 μg to 1000 μg per subject animal per day, which may be administered once or in several times. The agent is preferably administered in several times, every several days to several months. As concretely shown in the Examples below, the immunity-inducing agent of the present invention can cause regression of an already occurred tumor. Therefore, since the agent can exert its anticancer activity also against a small number of cancer cells at an early stage, development or recurrence of cancer can be prevented by using the agent before development of the cancer or after therapy for the cancer. That is, the immunity-inducing agent of the present invention is effective for both therapy and prophylaxis of cancer.

The immunity-inducing agent of the present invention may contain only a polypeptide or may be formulated by being mixed as appropriate with an additive such as a pharmaceutically acceptable carrier, diluent or vehicle suitable for each administration mode. Formulation methods and additives which may be used are well-known in the field of formulation of pharmaceuticals, and any of the methods and additives may be used. Specific examples of the additives include, but are not limited to, diluents such as physiological buffer solutions; vehicles such as sugar, lactose, corn starch, calcium phosphate, sorbitol and glycine; binders such as syrup, gelatin, gum arabic, sorbitol, polyvinyl chloride and tragacanth; and lubricants such as magnesium stearate, polyethylene glycol, talc and silica. Examples of the formulation include oral preparations such as tablets, capsules, granules, powders and syrups; and parenteral preparations such as inhalants, injection solutions, suppositories and solutions. These formulations may be prepared by commonly known production methods.

The immunity-inducing agent of the present invention may be used in combination with an immunoenhancer capable of enhancing the immune response in a living body. The immunoenhancer may be contained in the immunity-inducing agent of the present invention or administered as a separate composition to a patient in combination with the immunity-inducing agent of the present invention.

Examples of the immunoenhancer include adjuvants. Adjuvants can enhance the immune response by providing a reservoir of antigen (extracellularly or within macrophages), activating macrophages and stimulating specific sets of lymphocytes, thereby enhancing the immune response and hence the anticancer action. Therefore, especially in cases where the immunity-inducing agent of the present invention is used for therapy and/or prophylaxis of cancer, the immunity-inducing agent preferably comprises an adjuvant, in addition to the above-described polypeptide as an effective ingredient. Many types of adjuvants are well-known in the art, and any of these adjuvants may be used. Specific examples of the adjuvants include MPL (SmithKline Beecham), homologues of *Salmonella minnesota* Re 595 lipopolysaccharide obtained after purification and acid hydrolysis of the lipopolysaccharide; QS21 (SmithKline Beecham), pure QA-21 saponin purified from an extract of *Quillja saponaria*; DQS21 described in PCT application WO96/33739 (SmithKline Beecham); QS-7, QS-17, QS-18 and QS-L1 (So and 10 colleagues, "Molecules and cells", 1997, Vol. 7, p. 178-186); Freund's incomplete adjuvant; Freund's complete adjuvant; vitamin E; Montanide; alum; CpG oligonucleotides (see, for example, Kreig and 7 colleagues, Nature, Vol. 374, p. 546-549); poly-I:C and derivatives thereof (e.g., poly ICLC); and various water-in-oil emulsions prepared from biodegradable oils such as squalene and/or tocopherol. Among these, Freund's incomplete adjuvant; Montanide; poly-I:C and derivatives thereof; and CpG oligonucleotides are preferred. The mixing ratio between the above-described adjuvant and the polypeptide is typically about 1:10 to 10:1, preferably about 1:5 to 5:1, more preferably about 1:1. However, the adjuvant is not limited to the above-described examples, and adjuvants known in the art other than those described above may also be used when the immunity-inducing agent of the present invention is administered (see, for example, Goding, "Monoclonal Antibodies: Principles and Practice, 2nd edition", 1986). Preparation methods for mixtures or emulsions of a polypeptide and an adjuvant are well-known to those skilled in the art of vaccination.

Further, in addition to the above-described adjuvants, factors that stimulate the immune response of the subject may be used as the above-described immunoenhancer. For example, various cytokines having a property to stimulate lymphocytes and/or antigen-presenting cells may be used as the immunoenhancer in combination with the immunity-inducing agent of the present invention. A number of such cytokines capable of enhancing the immune response are known to those skilled in the art, and examples thereof include, but are not limited to, interleukin-12 (IL-12), GM-CSF, IL-18, interferon-α, interferon-β, interferon-ω, interferon-γ, and Flt3 ligand, which have been shown to enhance the prophylactic action of vaccines. Such factors may also be used as the above-described immunoenhancer, and may be contained in the immunity-inducing agent of the present invention, or may be prepared as a separate composition to be used in combination with the immunity-inducing agent of the present invention, to be administered to a patient.

By bringing the above-described polypeptide into contact with antigen-presenting cells in vitro, the antigen-presenting cells can be made to present the polypeptide. That is, the polypeptides (a) to (c) described above can be used as agents for treating antigen-presenting cells. Examples of the antigen-presenting cells which may be preferably used include dendritic cells and B cells having MHC class I molecules. Various MHC class I molecules have been identified and are well-known. MHC molecules in human are called HLA. Examples of HLA class I molecules include HLA-A, HLA-B and HLA-C, more specifically, HLA-A1, HLA-A0201, HLA-A0204, HLA-A0205, HLA-A0206, HLA-A0207, HLA-A11, HLA-A24, HLA-A31, HLA-A6801, HLA-B7, HLA-B8, HLA-B2705, HLA-B37, HLA-Cw0401 and HLA-Cw0602.

The dendritic cells or B cells having MHC class I molecules can be prepared from peripheral blood by a well-known method. For example, tumor-specific dendritic cells can be induced by inducing dendritic cells from bone marrow, umbilical cord blood or patient's peripheral blood using granulocyte-macrophage colony-stimulating factor (GM-CSF) and IL-3 (or IL-4), and then adding a tumor-related peptide to the culture system.

By administering an effective amount of such dendritic cells, a response desired for therapy of a cancer can be induced. As the cells to be used, bone marrow or umbilical cord blood donated by a healthy individual, or bone marrow, peripheral blood or the like from the patient himself may be used. When autologous cells of the patient are used, high safety can be attained and serious side effects are expected to be avoided. The peripheral blood or bone marrow may be any of a fresh sample, cold-stored sample and frozen sample. As for the peripheral blood, whole blood may be cultured or the leukocyte components alone may be separated and cultured, and the latter is more efficient and thus preferred. Further, among the leukocyte components, mononuclear cells may be separated. In cases where the cells are originated from bone marrow or umbilical cord blood, the whole cells constituting the bone marrow may be cultured, or mononuclear cells may be separated therefrom and cultured. Peripheral blood, the leukocyte components thereof and bone marrow cells contain mononuclear cells, hematopoietic stem cells and immature dendritic cells, from which dendritic cells are originated, and also CD4-positive cells and the like. As for the cytokine to be used, the production method thereof is not restricted, and a naturally-occurring or recombinant cytokine or the like may be employed as long as its safety and physiological activity have been confirmed. Preferably, a preparation with assured quality for medical use is used in a minimum necessary amount. The concentration of the cytokine(s) to be added is not restricted as long as the dendritic cells are induced at the concentration, and usually, the total concentration of the cytokine(s) is preferably about 10 to 1000 ng/mL, more preferably about 20 to 500 ng/mL. The culture may be carried out using a well-known medium usually used for culture of leukocytes. The culturing temperature is not restricted as long as proliferation of the leukocytes is attained at the temperature, and a temperature of about 37° C., which is the body temperature of human, is most preferred. The atmospheric environment during the culturing is not restricted as long as proliferation of the leukocytes is attained under the environment, and 5% $CO_2$ is preferably allowed to flow. The culturing period is not restricted as long as a necessary number of the cells are induced therewith, and usually 3 days to 2 weeks. As for the apparatuses used for separation and culturing of the cells, appropriate apparatuses, preferably those whose safety upon application to medical uses have been confirmed and whose operations are stable and simple, may be employed. In particular, as for the cell-culturing apparatus, not only a general vessel such as a Petri dish, flask or bottle, but also a layer type vessel, multistage vessel, roller bottle, spinner type bottle, bag type culturing vessel, hollow fiber column or the like may be used.

The method per se to be used for bringing the above-described polypeptide into contact with the antigen presenting cells in vitro may be carried out by a well-known method. For example, it may be carried out by culturing the antigen-presenting cells in a culture medium containing the above-described polypeptide. The concentration of the peptide in the medium is not restricted, and usually about 1 to 100 μg/ml, preferably about 5 to 20 μg/ml. The cell density during the culture is not restricted and usually about $10^3$ to $10^7$ cells/ml, preferably about $5\times10^4$ to $5\times10^6$ cells/ml. The culture may be carried out according to a conventional method at 37° C. under the atmosphere of 5% $CO_2$. The maximum length of the peptide which can be presented on the surface of the antigen-presenting cells is usually about 30 amino acid residues. Therefore, in cases where the antigen-presenting cells are brought into contact with the polypeptide in vitro, the polypeptide may be prepared such that its length is not more than about 30 amino acid residues, although the length is not restricted.

By culturing the antigen-presenting cells in the coexistence of the above-described polypeptide, the polypeptide is incorporated into an MHC molecule of the antigen-presenting cells and presented on the surface of the antigen-presenting cells. Therefore, using the above-described polypeptide, isolated antigen-presenting cells containing the complex between the polypeptide and the MHC molecule can be prepared. Such antigen-presenting cells can present the polypeptide against T cells in vivo or in vitro, and thereby induce, and allow proliferation of, cytotoxic T cells specific to the polypeptide.

By bringing the thus prepared antigen-presenting cells having the complex between the above-described polypeptide and the MHC molecule into contact with T cells in vitro, cytotoxic T cells specific to the polypeptide can be induced and allowed to proliferate. This may be carried out by coculturing the above-described antigen-presenting cells and T cells in a liquid medium. For example, it may be attained by suspending the antigen-presenting cells in a liquid medium, placing the suspension in vessels such as wells of a microplate, adding T cells thereto and then culturing the cells. The mixing ratio of the antigen-presenting cells with respect to the T cells in the coculture is not restricted, and is usually about 1:1 to 1:100, preferably about 1:5 to 1:20 in terms of the ratio between the numbers of the cells. The density of the antigen-presenting cells to be suspended in the liquid medium is not restricted, and is usually about 100 to 10,000,000 cells/ml, preferably about 10,000 to 1,000,000 cells/ml. The coculture is preferably carried out in accordance with a conventional method at 37° C. under the atmosphere of 5% $CO_2$. The culturing period is not restricted, and is usually 2 days to 3 weeks, preferably about 4 days to 2 weeks. The coculture is preferably carried out in the presence of one or more interleukins such as IL-2, IL-6, IL-7 and/or IL-12. In such cases, the concentration of IL-2 or IL-7 is usually about 5 to 20 U/ml, the concentration of IL-6 is usually about 500 to 2000 U/ml, and the concentration of IL-12 is usually about 5 to 20 ng/ml, but the concentrations of the interleukins are not restricted thereto. The above coculture may be repeated once to several times with addition of fresh antigen-presenting cells. For example, the operation of discarding the culture supernatant after the coculture and adding a fresh suspension of antigen-presenting cells to further conduct the coculture may be repeated once to several times. The conditions of each coculture may be the same as described above.

By the above-described coculture, cytotoxic T cells specific to the polypeptide are induced and allowed to proliferate. Thus, using the above-described polypeptide, isolated T cells can be prepared which selectively bind to the complex between the polypeptide and the MHC molecule.

As described in the Examples below, the gene encoding PDS5A is expressed specifically in breast cancer cells, breast cancer tissues, brain tumor cells, brain tumor tissues, esophagus cancer cells, esophagus cancer tissues, lung cancer cells, lung cancer tissues, renal cancer cells, renal cancer tissues, colon cancer cells, colon cancer tissues, perianal adenocarcinoma tissues, perianal adenocarcinoma cells, neuroblastoma cells and leukemia cells. Therefore, it is thought that, in these cancer species, a significantly larger amount of PDS5A exists than in normal cells. When cytotoxic T cells prepared as described above are administered to a living body while a part of PDS5A existing in cancer cells is presented by MHC molecules on the surface of the cancer cells, the cytotoxic T cells can damage the cancer cells using the presented polypeptide as a marker. Since antigen-presenting cells presenting the above-described polypeptide can induce, and allow proliferation of, cytotoxic T cells specific to the polypeptide also in vivo, cancer cells can be damaged also by administering the antigen-presenting cells to a living body. That is, the cytotoxic T cells and the antigen-presenting cells prepared using the polypeptide are also effective as therapeutic and/or prophylactic agents for cancer, similarly to the immunity-inducing agent of the present invention.

In cases where the above-described isolated antigen-presenting cells or isolated T cells are administered to a living body, these are preferably prepared by treating antigen presenting cells or T cells collected from the patient to be treated with the polypeptide (a) to (c) as described above in order to avoid the immune response in the living body that attacks these cells as foreign bodies.

The therapeutic and/or prophylactic agent for cancer comprising as an effective ingredient the antigen-presenting cells or T cells is preferably administered via a parenteral administration route, for example, by intravenous or intraarterial administration. The dose is appropriately selected depending on the symptoms, the purpose of administration and the like, and is usually 1 cell to 10,000,000,000,000 cells, preferably 1,000,000 cells to 1,000,000,000 cells, which dose is preferably administered once every several days to once every several months. The formulation may be, for example, the cells suspended in physiological buffered saline, and the formulation may be used in combination with another/other anticancer preparation(s) and/or cytokine(s). Further, one or more additives well-known in the field of formulation of pharmaceuticals may also be added.

Also by expressing a polynucleotide encoding any of the polypeptides (a) to (c) in the body of the subject animal, antibody production and cytotoxic T cells can be induced in the living body, and an effect comparable to that obtained in the case of administration of the polypeptide can be obtained. That is, the immunity-inducing agent of the present invention may be one comprising as an effective ingredient a recombinant vector having a polynucleotide encoding any of the polynucleotides (a) to (c), which recombinant vector is capable of expressing the polypeptide in a living body. Such a recombinant vector capable of expressing an antigenic polypeptide as shown in the later-mentioned Examples is also called a gene vaccine.

The vector used for production of the gene vaccine is not restricted as long as it is a vector capable of expressing the polypeptide in a cell of the subject animal (preferably in a mammalian cell), and may be either a plasmid vector or a virus vector, and any known vector in the field of gene vaccines may be used. The polynucleotide such as DNA or RNA encoding the above-described polypeptide can be easily prepared as mentioned above by a conventional method. Incorporation of the polynucleotide into the vector can be carried out using a method well-known to those skilled in the art.

The administration route of the gene vaccine is preferably a parenteral route such as intramuscular, subcutaneous, intravenous or intraarterial administration, and the dose may be appropriately selected depending on the type of the antigen and the like, and is usually about 0.1 μg to 100 mg, preferably about 1 μg to 10 mg in terms of the weight of the gene vaccine per 1 kg of body weight.

Examples of the method using a virus vector include those wherein a polynucleotide encoding the above-described polypeptide is incorporated into an RNA virus or DNA virus, such as a retrovirus, adenovirus, adeno-associated virus, herpes virus, vaccinia virus, pox virus, poliovirus or Sindbis virus, and then a subject animal is infected with the resulting virus. Among these methods, those using a retrovirus, adenovirus, adeno-associated virus, vaccinia virus or the like are especially preferred.

Examples of other methods include a method wherein an expression plasmid is directly intramuscularly administered (DNA vaccine method), liposome method, lipofectin method, microinjection method, calcium phosphate method and electroporation method, and the DNA vaccine method and liposome method are especially preferred.

Methods for actually making the gene encoding the above-described polypeptide used in the present invention act as a pharmaceutical include the in vivo method wherein the gene is directly introduced into the body, and the ex vivo method wherein a certain kind of cells are collected from a subject animal and the gene is introduced into the cells ex vivo, followed by returning the cells to the body (Nikkei Science, 1994, April, p. 20-45; The Pharmaceutical Monthly, 1994, Vol. 36, No. 1, p. 23-48; Experimental Medicine, Extra Edition, 1994, Vol. 12, No. 15; and references cited in these literatures, and the like). The in vivo method is more preferred.

In cases where the gene is administered by the in vivo method, the gene may be administered through an appropriate administration route depending on the disease to be treated, symptoms and so on. It may be administered by, for example, intravenous, intraarterial, subcutaneous or intramuscular administration. In cases where the gene is administered by the in vivo method, the gene may be formulated into a preparation such as a solution, and in general, it is formulated into an injection solution or the like containing DNA encoding the above-described peptide of the present invention as an effective ingredient. A commonly used carrier(s) may be also added thereto as required. In the case of a liposome or membrane fusion liposome (Sendai virus (HVJ)-liposome or the like) containing the DNA, the liposome may be formulated into a liposome preparation such as a suspension, frozen preparation or centrifugally concentrated frozen preparation.

In the present invention, "the base sequence shown in SEQ ID NO:1" includes not only the base sequence expressly written in SEQ ID NO:1, but also the sequence complementary thereto. Thus, "the polynucleotide having the base sequence shown in SEQ ID NO:1" includes a single-stranded polynucleotide having the base sequence expressly written in SEQ ID NO:1, a single-stranded polynucleotide having the base sequence complementary thereto, and a double-stranded polynucleotide composed of these single-stranded polynucleotides. When a polynucleotide encoding the polypeptide used in the present invention is prepared, any one of these base sequences is appropriately selected, and those skilled in the art can easily carry out the selection.

Further, since the polypeptide used in the present invention is expressed specifically in cancer, the polypeptide specifically reacts only with the serum in a cancer-bearing living body, so that the polypeptide of the present invention is used also for detection of cancer.

In the above-described method for detecting cancer, a sample separated from a living body is used to measure expression of a polypeptide having any one of the amino acid sequences shown in SEQ ID NOs:2, 4, 6, 8, 10, 12 and 44, or a polypeptide as a homologous factor thereof, having a sequence identity of not less than 90%, preferably not less than 95%, more preferably not less than 98%, still more preferably not less than 99% or not less than 99.5% to the polypeptide. Examples of the method for measuring the expression of the polypeptide using the sample includes a method in which an antibody against the polypeptide, which antibody is contained in the sample, is measured by immunoassay (Method 1); a method in which the polypeptide per se contained in the sample is measured by immunoassay (Method 2); and a method in which mRNA contained in the sample and encoding the polypeptide is measured (Method 3). In the method of the present invention, the expression of the polypeptide may be measured by any of these methods. In the present invention, the term "measurement" includes detection, quantification and semi-quantification.

Here, PDS5A is a polypeptide identified, by the SEREX method using a canine breast cancer-derived cDNA library and serum obtained from the same patient dog, as a polypeptide that binds to an antibody specifically existing in the serum derived from the tumor-bearing dog (cancer-specific antibody) (see Example 1). That is, in the living body of the tumor-bearing dog, an antibody against PDS5A is specifically induced. Therefore, by measuring the antibody against PDS5A in the living body of the tumor-bearing dog, a cancer expressing PDS5A can also be detected. Further, also by measuring PDS5A as an antigen by Method 2, the canine cancer can be detected. Further, since, as described in the later-mentioned Examples, mRNA encoding the antigen polypeptide is expressed at significantly higher levels in cancer cells and cancer tissues, especially in breast cancer cells, breast cancer tissues, brain tumor cells, brain tumor tissues, esophagus cancer cells, esophagus cancer tissues, lung cancer cells, lung cancer tissues, renal cancer cells, renal cancer tissues, colon cancer cells, colon cancer tissues, perianal adenocarcinoma cells, perianal adenocarcinoma tissues, neuroblastoma cells and leukemia cells, compared to the normal tissues (see Example 1), the canine cancer can be detected also by measuring the mRNA.

In Method 1 above, measurement of the cancer-specific antibody which may exist in the sample can be easily carried out by immunoassay using an antigenic substance which undergoes antigen-antibody reaction with the antibody. The immunoassay per se is a conventional well-known method as explained in detail below. Examples of the antigenic substance which may be used in the immunoassay include the polypeptides (a) to (c). Since antibodies have cross-reactivity, even a molecule other than the antigenic substance corresponding to the original immunogen may be bound to an antibody induced against the immunogen by antigen-antibody reaction, as long as the molecule has a structure thereon similar to an epitope of the immunogen. For example, polypeptides having a high sequence identity therebetween often have similar epitope structures, and, in this case, the both polypeptides may have the same antigenicity. As concretely described in the Examples below, the human-derived polypeptide of SEQ ID NO:4 or 44 undergoes antigen-antibody reaction with the above-described antibody induced in the body of a cancer-bearing dog. Therefore, in Method 1 of the present invention, any mammalian homologous factor may be used as the antigen in the immunoassay.

An antigenic substance having a complex structure and a large molecular weight, such as a protein, usually has a plurality of sites having different structures on the molecule. Therefore, against such an antigenic substance, a plurality of kinds of antibodies which recognize the respective plurality of sites are produced in a living body. That is, an antibody induced in a living body against an antigenic substance such as a protein is a polyclonal antibody, which is a mixture of a plurality of kinds of antibodies. It should be noted that, in the present invention, the term "polyclonal antibody" means antibodies which exist in serum from a living body having an antigenic substance therein and were induced in the living body against the antigenic substance.

Measurement of the antibody in a sample may easily be carried out by immunoassay using the above-described polypeptide as an antigen. Immunoassays per se are well-known in the art, and include, when classified based on the reaction mode, the sandwich method, competition method, agglutination method, Western blotting and the like. When classified based on the label, immunoassays include radioimmunoassay, fluorescence immunoassay, enzyme immunoassay, biotin immunoassay and the like, and the immunoassay of the above-described antibody may be carried out by any of these immunoassays. Although not restricted, the sandwich ELISA and the agglutination method may be preferably applied as the method of immunoassay of the above antibody in the present invention, since the operations are simple and a large-scale apparatus is not necessary in these methods. In cases where an enzyme is used as the label of the antibody, the enzyme is not particularly restricted as long as it satisfies conditions such as a large turnover number, stability upon binding with the antibody, and specific coloring of the substrate, and examples of the enzyme which may be used include enzymes used in an ordinary enzyme immunoassay, such as peroxidase, β-galactosidase, alkaline phosphatase, glucose oxidase, acetylcholinesterase, glucose-6-phosphate dehydrogenase, and malate dehydrogenase. An enzyme inhibitor, coenzyme and/or the like may also be used. Binding of the enzyme with the antibody may be carried out by a known method using a cross-linking agent such as a maleimide compound. As a substrate, a known substance may be used depending on the type of the enzyme to be used. For example, in cases where peroxidase is used as the enzyme, 3,3',5,5'-tetramethylbenzidine may be used; and in cases where alkaline phosphatase is used as the enzyme, para-nitrophenol or the like may be used. As a radioisotope, one used in an ordinary radioimmunoassay, such as $^{125}I$ or $^{3}H$ may be used. As a fluorescent dye, one used in an ordinary fluorescent antibody technique, such as fluorescein isothiocyanate (FITC), tetramethylrhodamine isothiocyanate (TRITC) or the like may be used.

These immunoassays per se are well-known in the art and do not need to be explained in the present specification. Briefly, in a sandwich immunoassay, for example, the above-mentioned polypeptide used as an antigen is immobilized on a solid phase and then reacted with a sample such as a serum. After washing the solid phase, the resultant is reacted with an appropriate secondary antibody. After washing the solid phase, the secondary antibody bound to the solid phase is measured. This method is preferred as an embodiment of the method of the present invention for detecting cancer since, in this method, immobilization of the antigen polypeptide to the solid phase enables simple removal of unbound secondary antibodies. As the secondary antibody, an anti-dog IgG antibody may be used in cases where, for example, the sample is derived from a dog. By preliminarily labeling the secondary antibody with a labeling substance exemplified above, the secondary antibody bound to the solid phase can be measured. The thus measured amount of the secondary antibody corresponds to the amount of the above-mentioned antibody in the serum sample. In cases where an enzyme is used as the labeling substance, the amount of the antibody may be measured by adding a substrate which develops a color upon decomposition by an enzymatic activity, and then optically measuring the amount of decomposition of the substrate. In cases where a radioisotope is used as the labeling substance, the amount of radiation emitted from the radioisotope may be measured with a scintillation counter or the like.

In Method 2 of the present invention, the polypeptide of SEQ ID NO:2, 4, 6, 8, 10, 12 or 44 or a homologous factor thereof, which may be contained in a sample obtained from a living body is measured. As mentioned above, the amount of a cancer-specific antibody which undergoes antigen-antibody reaction with the polypeptide of SEQ ID NO:2, 4, 6, 8, 10, 12 or 44 or a homologous factor thereof is significantly larger in cancer patients, and this indicates that the amount of production of the polypeptide or a homologous factor thereof, which corresponds to an antigen of the cancer-specific antibody, is significantly larger in the cancer patients. Therefore, cancer in a living body can be detected also by measuring the polypeptide of SEQ ID NO:2, 4, 6, 8, 10, 12 or 44 or a homologous factor thereof similarly to Method 1 described above.

The polypeptide in a sample can be easily measured by a well-known immunoassay. More particularly, for example, by preparing an antibody or an antigen-binding fragment thereof which undergoes antigen-antibody reaction with the polypeptide shown in SEQ ID NO:2, 4, 6, 8, 10, 12 or 44 and using this in an immunoassay, the polypeptide having the sequence shown in SEQ ID NO:2, 4, 6, 8, 10, 12 or 44 or a homologous factor thereof which may exist in the sample can be measured. The immunoassay per se is a well-known conventional method as described above.

The term "antigen-binding fragment" herein means an antigen fragment such as the Fab fragment or F(ab')2 fragment contained in the antibody molecule, which has a binding capacity to an antigen. The antibody may be either a polyclonal antibody or monoclonal, and a monoclonal antibody is preferred in an immunoassay and the like because a high reproducibility can be obtained therewith. The methods of preparation of a polyclonal antibody and a monoclonal antibody using a polypeptide as an immunogen are well known, and can be easily carried out by conventional methods. For example, antibodies against a polypeptide can be induced by immunizing an animal with, as an immunogen, the polypeptide conjugated to a carrier protein such as keyhole limpet hemocyanin (KLH) or casein, together with an adjuvant. Antibody-producing cells such as spleen cells or lymphocytes are then collected from the immunized animal and fused with myeloma cells to prepare hybridomas. Among the hybridomas, one producing an antibody which binds to the polypeptide shown in SEQ ID NO:2, 4, 6, 8, 10, 12 or 44, or a homologous factor thereof is selected and proliferated, and then a monoclonal antibody whose corresponding antigen is the above-mentioned protein can be obtained from the culture supernatant. The above-described method is a conventional well-known method.

In Method 3 of the present invention, mRNA which may be contained in a sample obtained from a living body and encodes PDS5A is measured. As concretely shown in the Examples below, mRNA encoding PDS5A is significantly highly expressed in tissues and cells of cancer, breast cancer, brain tumor, esophagus cancer, lung cancer, renal cancer, colon cancer, perianal adenocarcinoma, neuroblastoma and leukemia. Therefore, also by measuring the mRNA in the sample, cancer in the living body can be detected.

In the detection method of the present invention, whether or not a subject living body is suffering from cancer is judged based on the expression level of the polypeptide measured as described above. Although the cancer detection may be attained simply by measuring expression of the polypeptide in the subject living body, it is preferred, from the viewpoint of enhancement of the detection accuracy, to obtain a normal reference value by investigating the expression level of the polypeptide (the amount of the antibody, polypeptide or mRNA) in one or more samples from healthy individuals, followed by comparison of the measured value in the subject living body with the normal reference value. In cases where a higher detection accuracy is required, a cancer reference value may be obtained by investigating the expression level of the polypeptide in samples obtained from many patients known to be suffering from cancer, followed by comparison of the measured value in the subject living body both with the normal reference value and with the cancer reference value. The reference values may be determined by, for example, digitizing the expression level of the polypeptide in each sample and calculating the mean value. The normal reference value and the cancer reference value may be preliminarily determined by investigating the expression level of the polypeptide in many healthy individuals and cancer patients. Thus, in cases where comparison with the reference value(s) is carried out in the method of the present invention, a preliminarily determined reference value(s) may be used.

The detection method of the present invention may be used in combination with detection with another cancer antigen or cancer marker. By this, the accuracy of detection of cancer can be further increased.

By the detection method of the present invention, cancers in a living body can be detected. By the method of the present invention, even an invisible small cancer or a cancer which exists in a deep part of a body can be detected, and thus the method is useful for early detection of cancers. Further, by applying the detection method of the present invention to patients in the follow-up period after cancer therapy, a recurrent cancer, if any, can be detected at an early stage.

In a tumor-bearing living body, as the number of cancer cells expressing the specific polypeptide to be measured in the present invention increases, the amounts of accumulation of the polypeptide and the mRNA encoding it in the living body increase, leading to increased production of antibodies against the polypeptide in the serum. On the other hand, as the number of cancer cells decreases, the amounts of accumulation of the polypeptide and the mRNA encoding it in the living body decrease, leading to decrease in antibodies against the polypeptide in the serum. Thus, in cases where the expression level of the specific polypeptide is high, it can be determined that tumor growth and/or metastasis of cancer occurred, that is, the stage of progression of cancer is advanced.

Further, as shown in the Examples below, when compared between the same kind of tumors, a malignant one produces a significantly higher amount of the antibodies than a benign one. Therefore, in cases where the expression level of the specific polypeptides is high, it can be determined that the grade of cancer malignancy is high. That is, the grade of cancer malignancy can also be detected by the method of the present invention.

Furthermore, the effect of a cancer therapy can be monitored based on increase or decrease of the expression level of the specific polypeptide. Therefore, by observing the expression level of the above-mentioned polypeptide in an individual during or after a cancer therapy, one can obtain a clue(s) to know the effect of an anticancer drug, presence/absence of a residual tumor after extirpation of the tumor, and/or, even during the follow-up, metastasis and/or recurrence, as early as possible. In cases where a therapy is/was appropriate, the expression level of the polypeptide becomes lower than that in the patient in the tumor-bearing state before the therapy, and therefore the effect of the therapy that was (or is being) provided for the living body can be judged to have been (or to be) excellent. In cases where the expression level of the polypeptide increased or is maintained, or in cases where the expression level once decreased and then increased again, the therapeutic effect can be judged to be insufficient, and this observation can be a useful basis for selection of a therapeutic method, such as use of another therapeutic method or alteration of the dose of an anti-cancer agent.

Preferred examples of the cancer as the subject of the method for detecting cancer of the present invention include cancers expressing PDS5A, such as breast cancer, brain tumor, esophagus cancer, lung cancer, renal cancer, colon cancer, perianal adenocarcinoma, neuroblastoma and leukemia. The living body as the subject of the method of the present invention is preferably a mammal, more preferably human, dog or cat.

The sample to be provided for the method of the present invention include body fluids such as blood, serum, plasma, ascites and pleural effusion, and tissues and cells. Particularly, serum, plasma, ascites and pleural effusion may be preferably used in Method 1 and Method 2 above. A tissue sample and cell sample are preferred in the case of Method 3 above in which mRNA is measured.

The polypeptide used as the antigen for the immunoassay in Method 1 may be provided as a reagent for cancer detection. The reagent may consist essentially of the above-mentioned polypeptide, or may contain, for example, various additives useful for stabilizing the polypeptide, and/or the like. The reagent may be provided also in a state where it is immobilized on a solid phase such as a plate or membrane.

When the polypeptide shown in SEQ ID NO:2, 4, 6, 8, 10, 12 or 44 or a homologous factor thereof is to be immunoassayed in Method 2, an antibody or an antigen-binding fragment thereof which undergoes antigen-antibody reaction with the polypeptide or a homologous factor thereof may also be provided as a reagent for cancer detection. Also in this case, the reagent for cancer detection may consist essentially of the antibody or antigen-binding fragment, or may contain, for example, various additives useful for stabilizing the antibody or antigen-binding fragment, and/or the like. The antibody or antigen-binding fragment may also be in a state where a metal such as manganese or iron is bound thereto. Administration of such a metal-bound antibody or antigen-binding fragment into a living body causes higher accumulation of the antibody or antigen-binding fragment at locations where the antigen protein exists in a larger amount, so that measurement of the metal by MRI or the like enables detection of existence of cancer cells that produces the antigen protein.

Furthermore, the above-described polynucleotide for cancer detection to be used for measuring mRNA in Method 3 may also be provided as a reagent for cancer detection. Also in this case, the reagent for cancer detection may consist essentially of the polynucleotide, or may contain, for example, various additives useful for stabilizing the polynucleotide, and/or the like. The polynucleotide for cancer detection contained in the reagent is preferably a primer or a probe.

EXAMPLES

The present invention will now be described more concretely by way of Examples.

Example 1

Obtaining Novel Cancer Antigen Protein by SEREX Method (1) Preparation of cDNA Library Total RNA was extracted from a breast cancer tissue of a tumor-bearing dog by the Acid guanidium-Phenol-Chloroform method, and poly(A) RNA was purified using Oligotex-dT30 mRNA purification Kit (manufactured by Takara Shuzo Co., Ltd.) in accordance with the protocol attached to the kit.

Using the obtained mRNA (5 μg), a cDNA phage library was synthesized. For the preparation of the cDNA phage library, cDNA Synthesis Kit, ZAP-cDNA Synthesis Kit, and ZAP-cDNA Gigapack III Gold Cloning Kit (manufactured by STRATAGENE) were used in accordance with the protocols attached to the kits. The size of the prepared cDNA phage library was $1\times10^6$ pfu/ml.

(2) Screening of cDNA Library with Serum

Using the prepared cDNA phage library, immunoscreening was carried out. More particularly, the host *E. coli* (XL1-Blue MRF') was infected with the library such that 2340 clones appear on an NZY agarose plate having a size of Φ90×15 mm, and cultured at 42° C. for 3 to 4 hours to allow the phage to form plaques. The plate was covered with a nitrocellulose membrane (Hybond C Extra: manufactured by GE Healthcare Bio-Science) impregnated with IPTG (isopropyl-β-D-thiogalactoside) at 37° C. for 4 hours to allow induction and expression of proteins, which were thus transferred to the membrane. Subsequently, the membrane was recovered and soaked in TBS (10 mM Tris-HCl, 150 mM NaCl; pH 7.5) containing 0.5% non-fat dry milk, followed by shaking it at 4° C. overnight to suppress non-specific reactions. This filter was then allowed to react with 500-fold diluted canine patient serum at room temperature for 2 to 3 hours.

As the above-described canine patient serum, serum collected from a canine patient suffering from perianal tumor was used. The serum was stored at −80° C. and pretreated immediately before use. The method of the pretreatment of the serum was as follows. That is, the host *E. coli* (XL1-Blue MRF') was infected with λ ZAP Express phage to which no foreign gene was inserted, and then cultured on NZY plate medium at 37° C. overnight. Subsequently, 0.2 M $NaHCO_3$ buffer (pH 8.3) containing 0.5 M NaCl was added to the plate, and the plate was left to stand at 4° C. for 15 hours, followed by collecting the supernatant as an *E. coli*/phage extract. Thereafter, the collected *E. coli*/phage extract was allowed to flow through an NHS column (manufactured by GE Healthcare Bio-Science) to immobilize proteins derived from the *E. coli*/phage thereon. The serum from the canine patient was allowed to flow through and react with this protein-immobilized column to remove antibodies adsorbed to *E. coli* and/or the phage. The serum fraction that passed through the column was 500-fold diluted with TBS containing 0.5% non-fat dry milk, and the resulting diluent was used as the material for the immunoscreening.

The membrane on which the thus treated serum and the above-described fusion protein were blotted was washed 4 times with TBS-T (0.05% Tween 20/TBS), and allowed to react with goat anti-dog IgG (Goat anti Dog IgG-h+I HRP conjugated: manufactured by BETHYL Laboratories) 5.000-fold diluted with TBS containing 0.5% non-fat dry milk as a secondary antibody at room temperature for 1 hour, followed by detection by the enzyme coloring reaction using the NBT/BCIP reaction solution (manufactured by Roche). Colonies at positions where a positive coloring reaction was observed were recovered from the NZY agarose plate having a size of Φ90×15 mm, and dissolved in 500 μl of SM buffer (100 mM NaCl, 10 mM $MgClSO_4$, 50 mM Tris-HCl, 0.01% gelatin; pH 7.5). The screening was repeated as a second and third screening in the same manner as described above until a single coloring reaction-positive colony was obtained, thereby isolating one positive clone after screening of 30940 phage clones reactive with IgG in the serum.

(3) Sequence Homology Search of Isolated Antigen Gene

To subject the single positive clone isolated by the above-described method to a base sequence analysis, an operation of conversion of the phage vector to a plasmid vector was carried out. More particularly, 200 µl of a solution prepared such that the host *E. coli* (XL1-Blue MRF') was contained at an absorbance $OD_{600}$ of 1.0 was mixed with 100 µl of a purified phage solution and further with 1 µl of ExAssist helper phage (manufactured by STRATAGENE), and the reaction was allowed to proceed at 37° C. for 15 minutes. To the reaction mixture, 3 ml of LB medium was added, and the resulting mixture was cultured at 37° C. for 2.5 to 3 hours, followed by immediate incubation in a water bath at 70° C. for 20 minutes. The mixture was then centrifuged at 4° C. at 1,000×g for 15 minutes, and the supernatant was recovered as a phagemid solution. Subsequently, 200 µl of a solution prepared such that the phagemid host *E. coli* (SOLR) was contained at an absorbance $OD_{600}$ of 1.0 was mixed with 10 µl of a purified phage solution, and the reaction was allowed to proceed at 37° C. for 15 minutes. Thereafter, 50 µl of the reaction mixture was plated on LB agar medium supplemented with ampicillin (final concentration: 50 µg/ml), and cultured at 37° C. overnight. A single colony of transformed SOLR was recovered and cultured in LB medium supplemented with ampicillin (final concentration: 50 µg/ml) at 37° C., followed by purification of plasmid DNA having the insert of interest using QIAGEN plasmid Miniprep Kit (manufactured by Qiagen).

The purified plasmid was subjected to analysis of the full-length sequence of the insert by the primer walking method using the T3 primer described in SEQ ID NO:13 and the T7 primer described in SEQ ID NO:14. By this sequence analysis, the gene sequence described in SEQ ID NO:1 was obtained. Using the base sequence and the amino acid sequence of this gene, homology search against known genes was carried out using a sequence homology search program BLAST (http://www.ncbi.nlm.nih.gov/BLAST/). As a result, it was revealed that the obtained gene is the PDS5A gene. Human PDS5A, which is a human homologous factor of canine PDS5A, had a sequence identity of 94% in terms of the base sequence and 99% in terms of the amino acid sequence; murine PDS5A, which is a murine homologous factor, had a sequence identity of 91% in terms of the base sequence and 99% in terms of the amino acid sequence; bovine PDS5A, which is a bovine homologous factor, had a sequence identity of 95% in terms of the base sequence and 99% in terms of the amino acid sequence; equine PDS5A, which is a equine homologous factor, had a sequence identity of 96% in terms of the base sequence and 99% in terms of the amino acid sequence; and chicken PDS5A, which is a chicken homologous factor, had a sequence identity of 83% in terms of the base sequence and 98% in terms of the amino acid sequence. In terms of human PDS5A, the base sequence is shown in SEQ ID NOs:3 and 43, and the amino acid sequence is shown in SEQ ID NOs:4 and 44; in terms of murine PDS5A, the base sequence is shown in SEQ ID NO:5, and the amino acid sequence is shown in SEQ ID NO:6; in terms of bovine PDS5A, the base sequence is shown in SEQ ID NO:7, and the amino acid sequence is shown in SEQ ID NO:8; in terms of equine PDS5A, the base sequence is shown in SEQ ID NO:9, and the amino acid sequence is shown in SEQ ID NO:10; and in terms of chicken PDS5A, the base sequence is shown in SEQ ID NO:11, and the amino acid sequence is shown in SEQ ID NO:12.

(4) Analysis of Expression in Various Tissues

Figure 2:
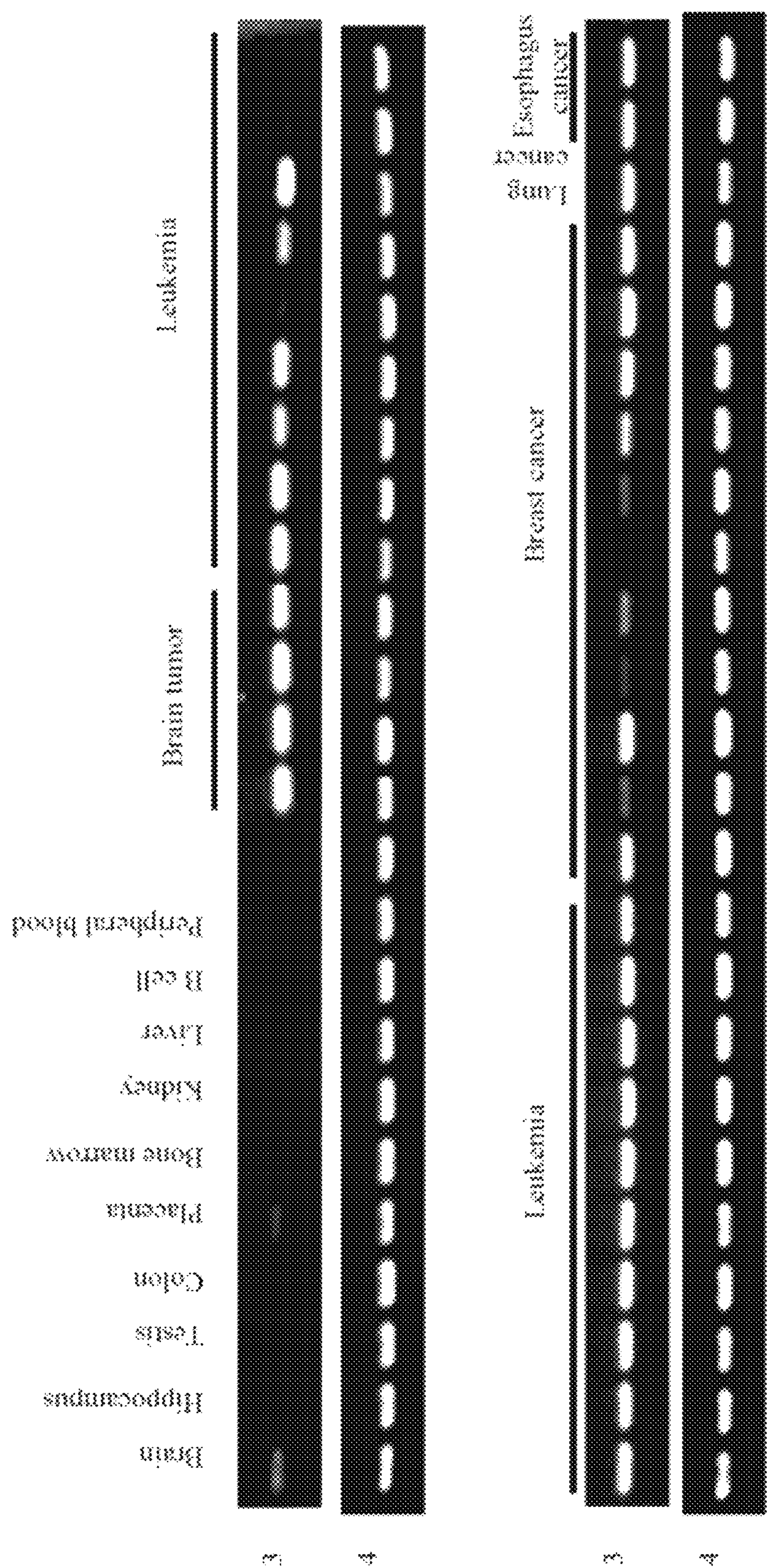
FIG. 2 shows the expression patterns of the identified PDS5A gene in human normal tissues, tumor tissues and tumor cell lines. Reference numeral 3, the expression patterns of the human PDS5A gene in various human tissues and cell lines; reference numeral 4, the expression patterns of the human GAPDH gene in various human tissues and cell lines.
Figure 3:
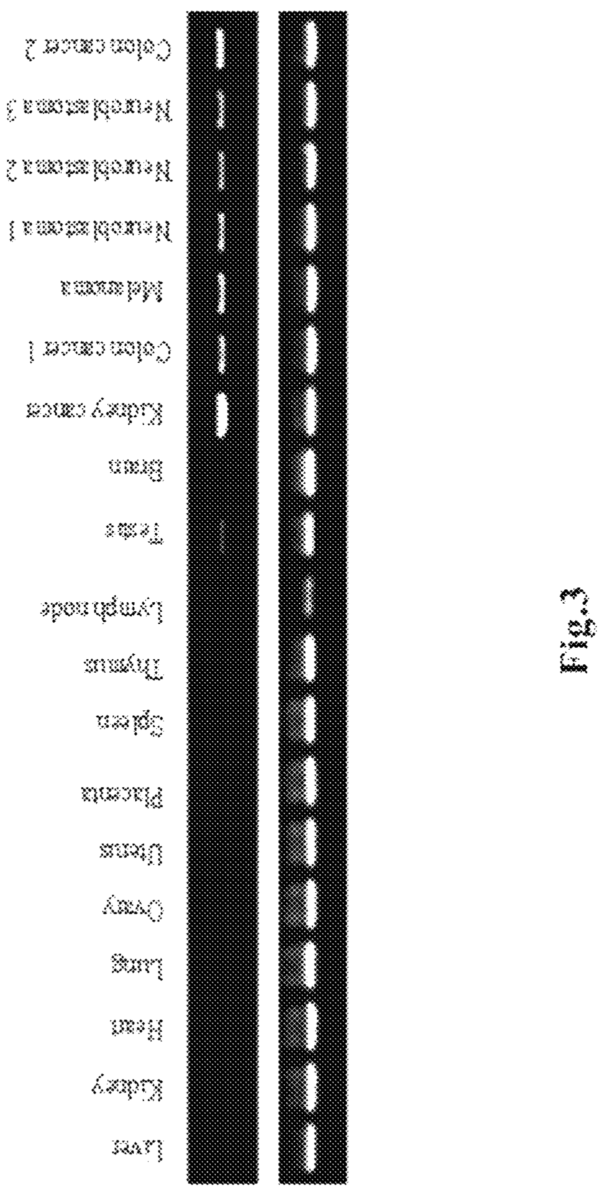
FIG. 3 shows the expression patterns of the identified PDS5A gene in murine normal tissues, tumor tissues and tumor cell lines. Reference numeral 5, the expression patterns of the murine PDS5A gene in various murine tissues and cell lines; reference numeral 6, the expression patterns of the murine GAPDH gene in various murine tissues and cell lines.

Expression of the genes obtained by the above method in canine, human and murine normal tissues and various cell lines were investigated by the RT-PCR (Reverse Transcription-PCR) method. The reverse transcription reaction was carried out as follows. That is, from 50 to 100 mg of each tissue or $5\times10^6$ to $10\times10^6$ cells of each cell line, total RNA was extracted using the TRIZOL reagent (manufactured by INVITROGEN) according to the protocol described in the attached instructions. Using this total RNA, cDNA was synthesized with the Superscript First-Strand Synthesis System for RT-PCR (manufactured by INVITROGEN) according to the protocol described in the attached instructions. As the cDNAs of human normal tissues (brain, hippocampus, testis, colon and placenta), Gene Pool cDNA (manufactured by INVITROGEN), QUICK-Clone cDNA (manufactured by CLONETECH) and Large-Insert cDNA Library (manufactured by CLONETECH) were used. The PCR reaction was carried out using gene-specific primers (the canine primers described in SEQ ID NOs:15 and 16, the human primers described in SEQ ID NOs:17 and 18, and the murine primers described in SEQ ID NOs:19 and 20) as described below. That is, reagents and an attached buffer were mixed such that 0.25 µl of the sample prepared by the reverse transcription reaction, 2 µM each of the above primers, 0.2 mM each of dNTPs, and 0.65 U ExTaq polymerase (manufactured by Takara Shuzo Co., Ltd.) were contained in a total volume of 25 µl, and the reaction was carried out by repeating 30 times the cycle of 94° C. for 30 seconds, 55° C. for 30 seconds and 72° C. for 1 minute using a Thermal Cycler (manufactured by BIO RAD). As a control for comparison, primers specific to GAPDH (the canine and human GAPDH primers are shown in SEQ ID NOs:21 and 22; and the murine GAPDH primers are shown in SEQ ID NOs:23 and 24) were used at the same time. As a result, as shown in FIG. 1, in terms of the canine PDS5A gene, expression was not observed in most of the healthy canine tissues, while strong expression was observed in the canine tumor tissues. Also in terms of the human and murine PDS5A genes, expression was not observed in most of the healthy human and murine tissues, while expression was detected in most of the cancer cell lines (FIGS. 2 and 3), as in the case of the canine PDS5A gene.

Example 2

Analysis of Cancer Antigenicity and Evaluation of Pharmacological Effect of PDS5A in Living Body (1) Preparation of Recombinant Vector that Expresses PDS5A in Living Body Based on the base sequence of SEQ ID NO:5, a recombinant vector that expresses PDS5A in a living body was prepared. Reagents and an attached buffer were mixed together such that 1 µl of the cDNA prepared from the murine cancer cell line N2a (purchased from ATCC), which showed expression in Example 1, 0.4 µM each of two kinds of primers having the NotI and XhoI restriction sites (shown in SEQ ID NOs:25 and 26), 0.2 mild dNTP and 1.25 U PrimeSTAR HS polymerase (manufactured by Takara Shuzo Co., Ltd.) were contained in a total volume of 50 µl, and PCR was carried out by repeating 30 times the cycle of 98° C. for 10 seconds, 55° C. for 15 seconds and 72° C. for 4 minute using a Thermal Cycler (manufactured by BIO RAD). The above-described two kinds of primers were those for amplification of the region encoding the full-length of the amino acid sequence shown in SEQ ID NO:5. After the PCR, the amplified DNA was subjected to electrophoresis using 1% agarose gel, and a DNA fragment of about 4000 bp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and the plasmid was then recovered. The amplified gene fragment was confirmed to have the same sequence as that of interest by sequencing. The plasmid having the same sequence as that of interest was treated with restriction enzymes NotI and XhoI, and purified using QIAquick Gel Extraction Kit, followed by inserting the gene sequence of interest into a mammalian expression vector PCDNA3.1 (manufactured by Invitrogen) that had been treated with restriction enzymes NotI and XhoI. Use of this vector enables production of the PDS5A protein in mammalian cells.

To 100 μg of the thus prepared plasmid DNA, 50 μg of gold particles (manufactured by Bio Rad), 100 μl spermidine (manufactured by SIGMA) and 100 μl of 1 M $CaCl_2$ (manufactured by SIGMA) were added, and the resulting mixture was stirred by vortexing, followed by leaving the mixture to stand for 10 minutes at room temperature (the resulting particles are hereinafter referred to as gold-DNA particles). The mixture was then centrifuged at 3000 rpm for 1 minute and the supernatant was discarded, followed by rinsing the precipitate 3 times with 100% ethanol (manufactured by WAKO). To the gold-DNA particles, 6 ml of 100% ethanol was added, and the resulting mixture was sufficiently stirred by vortexing, followed by pouring the gold-DNA particles into Tefzel Tubing (manufactured by Bio Rad) and allowing the particles to precipitate on the wall surface. The ethanol in the Tefzel Tubing to which the gold-DNA particles are attached was dried in the air, and the tube was cut into pieces having a length appropriate for a gene gun.

(2) Anti-Tumor Effect of PDS5A by DNA Vaccine Method

Each of a murine neuroblastoma cell line N2a and a colon cancer cell line CT26 were subcutaneously transplanted to 10 individuals of A/J mice (7 weeks old, male, purchased from Japan SLC) and Balb/c mice (7 weeks old, male, purchased from Japan SLC) in an amount of $1\times10^6$ cells. The above prepared tube was fixed in a gene gun, and a pressure of 400 psi was applied using pure helium gas to perform percutaneous administration of the DNA vaccine to the abdominal cavity of each mouse whose hair had been shaved, which administration was repeated a total of 3 times at intervals of 7 days (this corresponds to 2 μg/individual in terms of the dose of the inoculated amount of the plasmid DNA) to evaluate the anti-tumor effect (therapeutic model). Further, in a similar manner, the DNA vaccine was subcutaneously administered to each of 10 individuals of A/J mice and Balb/c mice a total of 3 times at intervals of 7 days, and N2a cells or CT26 cells were then transplanted to each mouse to evaluate the anti-tumor effect (prophylactic model). As a control, a plasmid DNA to which the PDS5A gene was not inserted was administered to 10 individuals in each model.

Figure 4:
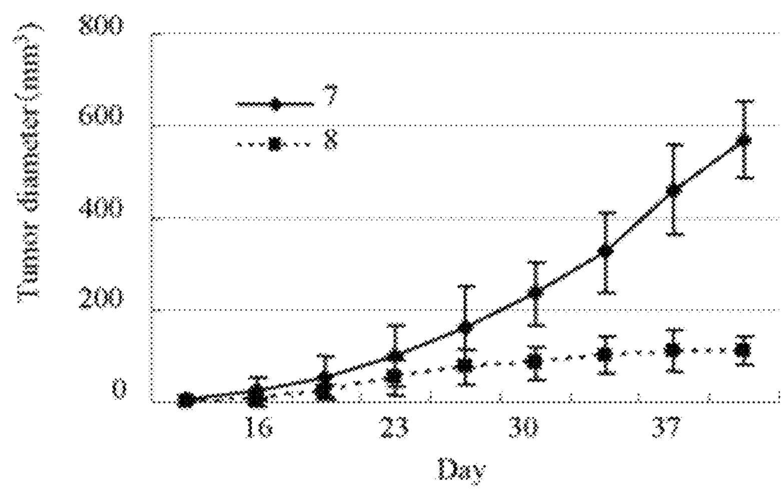
FIG. 4 is a graph showing that an anti-tumor effect (therapeutic model: neuroblastoma cell line) was observed by administration of PDS5A. Immunization was carried out with a vector alone or a plasmid encoding PDS5A using a gene gun, and the evaluation was carried out based on the area of the cancerous part and the ratio of living mice. For each group, 10 individuals of mice were used. The mice were observed twice a week. The data are represented by the mean value±SD. Reference numeral 7, the group wherein a plasmid vector was administered; reference numeral 8, the group wherein a plasmid encoding PDS5A was administered.
Figure 5:
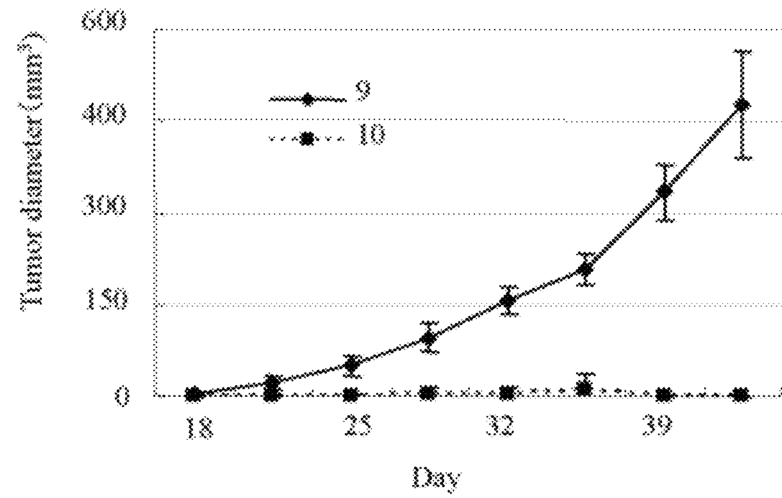
FIG. 5 is a graph showing that an anti-tumor effect (prophylactic model: neuroblastoma cell line) was observed by administration of PDS5A. Immunization was carried out with a vector alone or a plasmid encoding PDS5A using a gene gun, and the evaluation was carried out based on the area of the cancerous part and the ratio of living mice. For each group, 10 individuals of mice were used. The mice were observed twice a week. The data are represented by the mean value±SD. Reference numeral 9, the group wherein a plasmid vector was administered; reference numeral 10, the group wherein a plasmid encoding PDS5A was administered.
Figure 6:
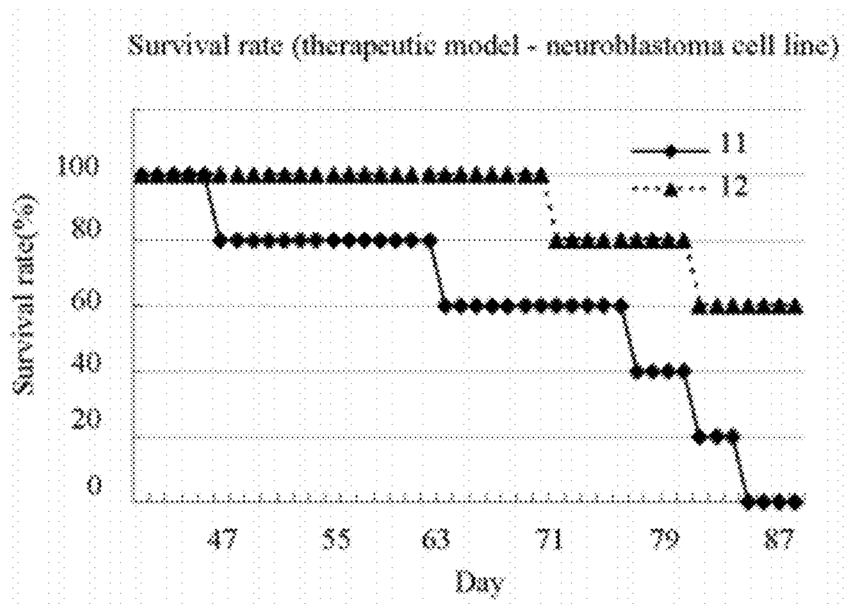
FIG. 6 shows the ratio of living mice in the experiment in FIG. 4. Reference numeral 11, the group wherein a plasmid vector was administered; reference numeral 12, the group wherein a plasmid encoding PDS5A was administered.
Figure 7:
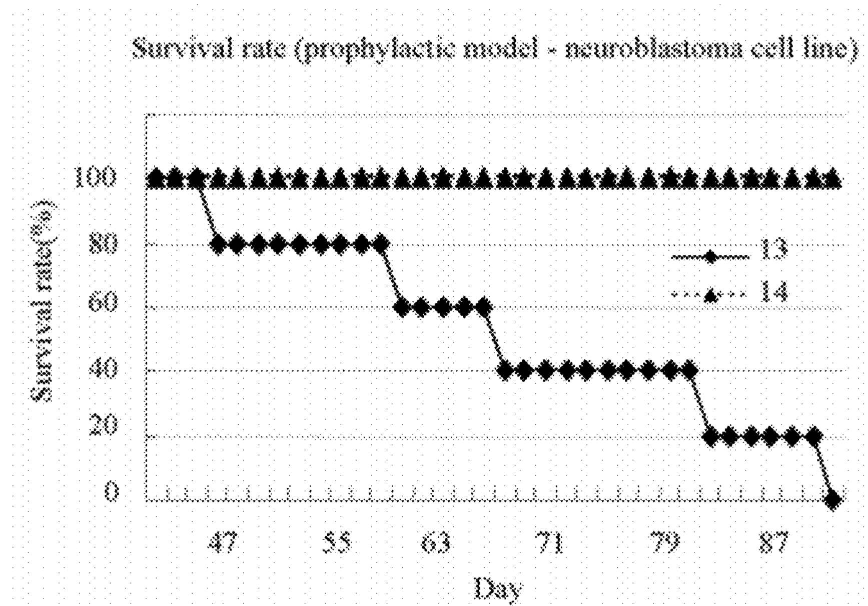
FIG. 7 shows the ratio of living mice in the experiment in FIG. 5. Reference numeral 13, the group wherein a plasmid vector was administered; reference numeral 14, the group wherein a plasmid encoding PDS5A was administered.
Figure 8:
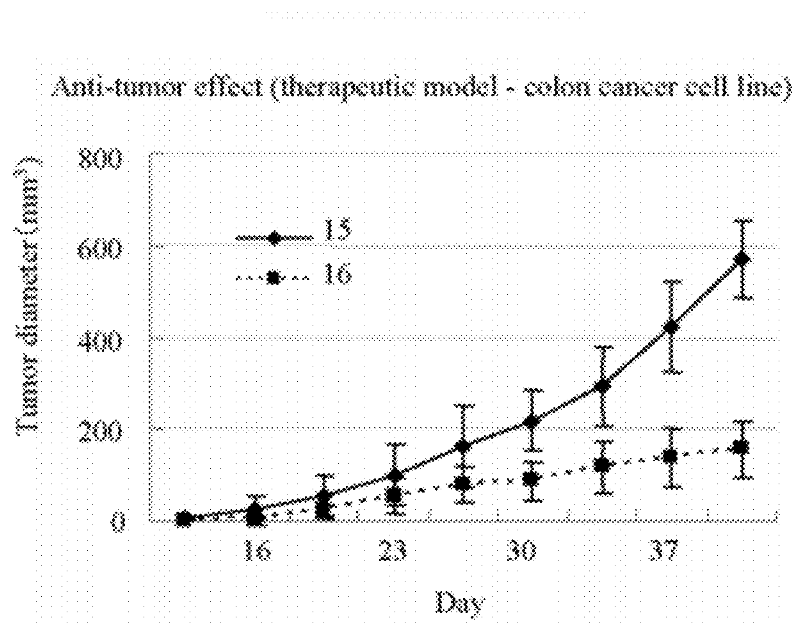
FIG. 8 is a graph showing that an anti-tumor effect (therapeutic model: colon cancer cell line) was observed by administration of PDS5A. Immunization was carried out with a vector alone or a plasmid encoding PDS5A using a gene gun, and the evaluation was carried out based on the area of the cancerous part and the ratio of living mice. For each group, 10 individuals of mice were used. The mice were observed twice a week. The data are represented by the mean value±SD. Reference numeral 15, the group wherein a plasmid vector was administered; reference numeral 16, the group wherein a plasmid encoding PDS5A was administered.
Figure 9:
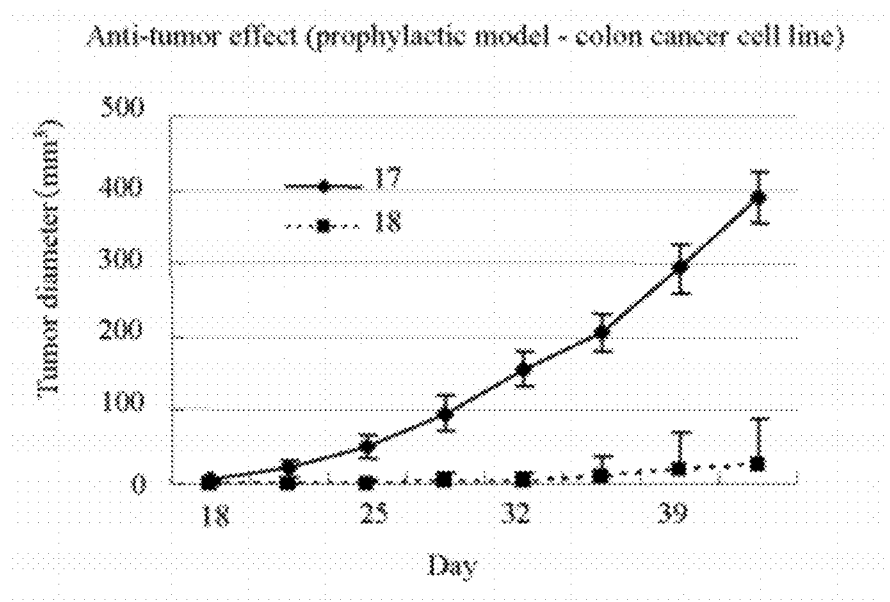
FIG. 9 is a graph showing that an anti-tumor effect (prophylactic model: colon cancer cell line) was observed by administration of PDS5A. Immunization was carried out with a vector alone or a plasmid encoding PDS5A using a gene gun, and the evaluation was carried out based on the area of the cancerous part and the ratio of living mice. For each group, 10 individuals of mice were used. The mice were observed twice a week. The data are represented by the mean value SD. Reference numeral 17, the group wherein a plasmid vector was administered; reference numeral 18, the group wherein a plasmid encoding PDS5A was administered.
Figure 10:
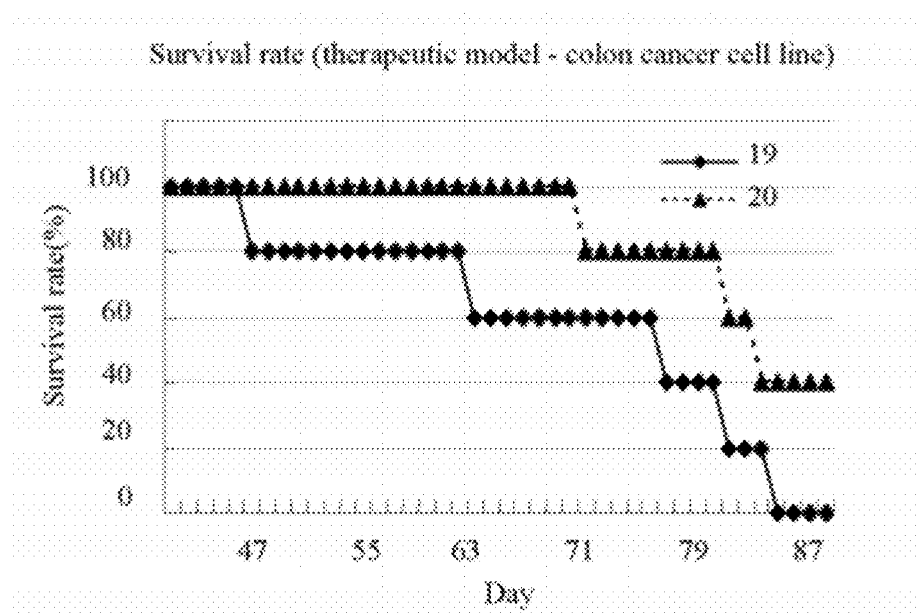
FIG. 10 shows the ratio of living mice in the experiment in FIG. 8. Reference numeral 19, the group to which a plasmid vector was administered; reference numeral 20, the group to which a plasmid encoding PDS5A was administered.
Figure 11:
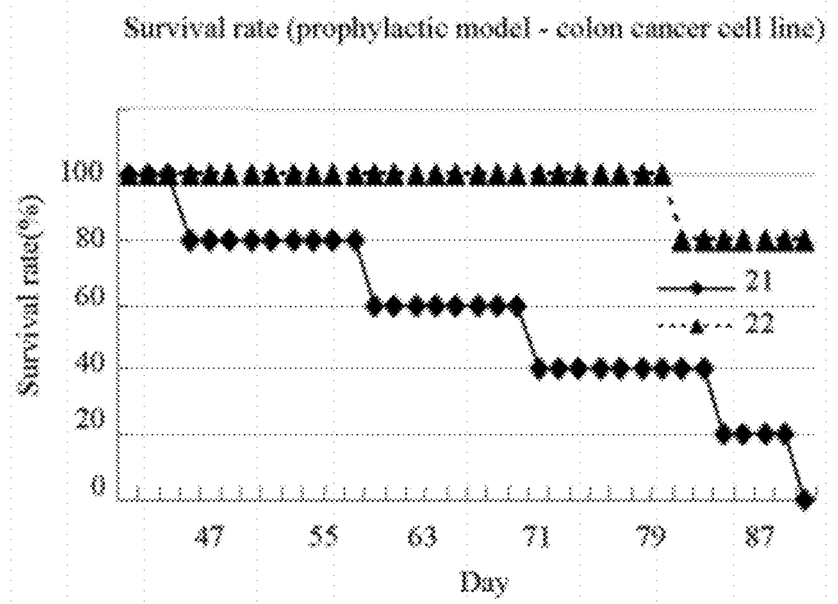
FIG. 11 shows the ratio of living mice in the experiment in FIG. 9. Reference numeral 21, the group to which a plasmid vector was administered; reference numeral 22, the group to which a plasmid encoding PDS5A was administered.

The anti-tumor effect was evaluated based on the size of the tumor (major axis×minor axis$^2$/2) and the ratio of living mice. The results are shown in FIGS. 4 to 11. As a result of this study, in the therapeutic model using the neuroblastoma cell line, the size of the tumor on Day 41 was 569 $mm^3$ and 109 $mm^3$ in the control group and the PDS5A plasmid-administered group, respectively, indicating significant reduction of the tumor in the PDS5A plasmid-administered group (FIG. 4). Similarly, in the prophylactic model using the neuroblastoma cell line, the size of the tumor on Day 43 was 476 $mm^3$ and 0 $mm^3$ in the control group and the PDS5A plasmid-administered group, respectively, indicating complete regression of the tumor in the PDS5A plasmid-administered group (FIG. 5). Further, in the therapeutic model using the colon cancer cell line, the size of the tumor on Day 41 was 589 $mm^3$ and 189 $mm^3$ in the control group and the PDS5A plasmid-administered group, respectively, indicating significant reduction of the tumor in the PDS5A plasmid-administered group (FIG. 8). Further, in the prophylactic model using the colon cancer cell line, the size of the tumor on Day 43 was 397 $mm^3$ and 43 $mm^3$ in the control group and the PDS5A plasmid-administered group, respectively, indicating significant reduction of the tumor in the PDS5A plasmid-administered group (FIG. 9). Based on observation of the process of survival in the both models using the neuroblastoma cell line, while all the cases in the control group died by Day 84 after the administration, 60% of the mice were alive at that time in the PDS5A plasmid-administered group (FIG. 6). Further, in the prophylactic model, while all the cases in the control group died by Day 90 after the administration, all the mice were alive at that time in the PDS5A plasmid-administered group (FIG. 7). Further, based on observation of the process of survival in the both models using the colon cancer cell line, while all the cases in the control group died by Day 84 after the administration, 40% of the mice were alive at that time in the PDS5A plasmid-administered group (FIG. 10). Further, in the prophylactic model, while all the cases in the control group died by Day 90 after the administration, 80% of the mice were alive at that time in the PDS5A plasmid-administered group (FIG. 11).

In the above results, a significantly higher anti-tumor effect was observed in the PDS5A-plasmid administered group than in the control group, and, by this observation, it was revealed that PDS5A is a cancer antigen having a strong cancer antigenicity and effective for therapy and prophylaxis of cancer.

Example 3

Induction of Peptide Epitope-Reactive CD8-Positive T Cells

For prediction of an HLA-A0201-binding motif in the amino acid sequence of the human PDS5A protein, a computer-based prediction program using the known BIMAS software (available at http://bimas.dcrtnih.gov/molbio/hla_bind/) was used to analyze the amino acid sequences shown in SEQ ID NOs:4 and 44, and thereby the polypeptides shown in SEQ ID NOs:27 to 35, which were expected to be capable of binding to the HLA class I molecule, were selected.

From an HLA-A0201-positive healthy individual, peripheral blood was separated, and the peripheral blood was overlaid on Lymphocyte separation medium (OrganonpTeknika, Durham, N.C.), followed by centrifuging the resultant at 1,500 rpm at room temperature for 20 minutes. A fraction containing peripheral blood mononuclear cells (PBMCs) was recovered and washed 3 times in a cold phosphate buffer, to obtain PBMCs. The obtained PBMCs were suspended in 20 ml of AIM-V medium (Life Technologies, Inc., Grand Island, N.Y., USA), and the cells were allowed to attach to a culture flask (Falcon) at 37° C. under 5% $CO_2$ for 2 hours. Unattached cells were used for preparation of T cells, and attached cells were used for preparation of dendritic cells.

The attached cells were cultured in AIM-V medium in the presence of IL-4 (1000 U/ml) and GM-CSF (1000 U/ml). The medium was replaced 6 days later with AIM-V medium supplemented with IL-4 (1000 U/ml), GM-CSF (1000 U/ml), IL-6 (1000 U/ml, Genzyme, Cambridge, Mass.), IL-1β (10 ng/ml, Genzyme, Cambridge, Mass.) and TNF-α (10 ng/ml, Genzyme, Cambridge, Mass.), and the culture was carried out for additional 2 days to obtain a population of unattached cells, which were employed as the dendritic cells.

The prepared dendritic cells were suspended in AIM-V medium at a cell density of $1\times10^6$ cells/ml, and each of the selected polypeptides was added at a concentration of 10 μg/ml to the suspension. Using a 96-well plate, the cells were cultured at 37° C. under 5% $CO_2$ for 4 hours. After the culture, X-ray irradiation (3000 rad) was carried out, and the cells were washed with AIM-V medium, followed by being suspended in AIM-V medium supplemented with 10% human AB serum (Nabi, Miami, Fla.), IL-6 (1000 U/ml) and IL-12 (10 ng/ml, Genzyme, Cambridge, Mass.). The cells were placed in a 24-well plate in an amount of $1\times10^5$ cells/well. Further, the prepared T cell population was added to each well in an amount of $1\times10^6$ cells, and cultured at 37° C. under 5% $CO_2$. Each culture supernatant was discarded 7 days later, and dendritic cells obtained in the same manner as described above by treatment with each polypeptide and the subsequent X-ray irradiation were suspended in AIM-V medium supplemented with 10% human AB serum (Nabi, Miami, Fla.), IL-7 (10 U/ml, Genzyme, Cambridge, Mass.) and IL-2 (10 U/ml, Genzyme, Cambridge, Mass.) (cell density, $1\times10^5$ cells/ml), which suspension was then added to the 24-well plate in an amount of $1\times10^5$ cells/well, followed by further culturing the cells. The same operation was repeated 4 to 6 times at intervals of 7 days, and stimulated T cells were then recovered, followed by confirmation of induction of CD8-positive T cells by flow cytometry.

Example 4

Figure 12:
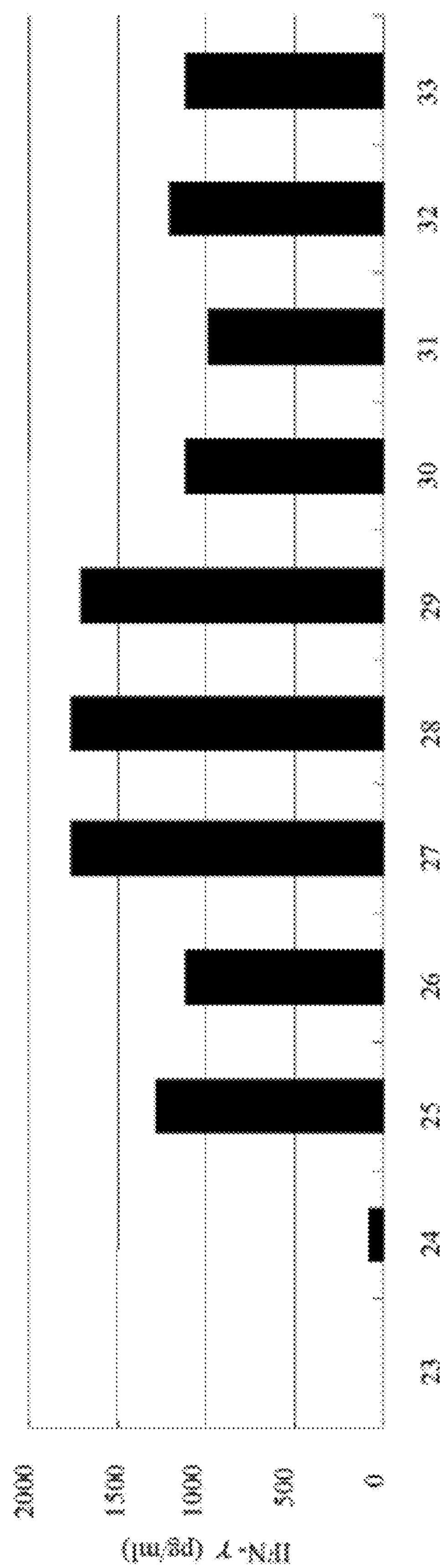
FIG. 12 is a diagram showing that CD8-positive T cells specific to each of the polypeptides having the amino acid sequences shown in SEQ ID NOs:27 to 35 in SEQUENCE LISTING recognize the complex between the polypeptide and HLA-A0201, and produce IFN-γ.

Determination of Cytotoxic T Cell Antigen Epitope in PDS5A that Stimulates HLA-A0201-Positive CD8-Positive T Cells Among the induced T cells in the respective wells, growth of T cells stimulated by each of the polypeptides of SEQ ID NOs:27 to 35 was confirmed by counting of the cell number under the microscope. In order to investigate the specificity of the respective T cells, whose growth was confirmed, to each polypeptide used for pulsing, $5\times10^3$ T cells were added with respect to $5\times10^4$ T2 cells expressing the HLA-A0201 molecule (Salter R D et al., Immunogenetics, 21: 235-246 (1985), purchased from ATCC) pulsed with the polypeptide (each polypeptide was added to AIM-V medium at a concentration of 10 μg/ml, and the cells were cultured therein at 37° C. under 5% $CO_2$ for 4 hours), and the cells were cultured in AIM-V medium supplemented with 10% human AB serum in a 96-well plate for 24 hours. After recovering the supernatant after the culture, the amount of production of IFN-γ was measured by the ELISA method. As a result, higher production of IFN-γ was confirmed in the culture supernatants in the wells containing T2 cells pulsed with the respective polypeptides shown in SEQ ID NOs:27 to 35 compared to the culture supernatants in the wells containing T2 cells which were not pulsed with a polypeptide (FIG. 12). Thus, it was revealed that each of the polypeptides of SEQ ID NOs:27 to 35 is a T cell epitope peptide having a capacity to stimulate and proliferate HLA-A0201-positive CD8-positive T cells, to induce production of IFN-γ. On the other hand, in the case where the polypeptide having the amino acid sequence shown in SEQ ID NO:36, which is outside the scope of the present invention, was added to perform the above-described treatment, no production of IFN-γ could be confirmed (FIG. 12).

Subsequently, whether or not the respective polypeptides shown in SEQ ID NOs:27 to 35, which are polypeptides to be used in the present invention, are presented on HLA-A0201 molecules on HLA-A0201-positive tumor cells expressing PDS5A, and whether or not CD8-positive cells stimulated with the polypeptides can damage HLA-A0201-positive tumor cells expressing PDS5A, were studied.

In a 50-ml centrifuge tube, $10^5$ cells of a malignant brain tumor cell line T98G, whose expression of PDS5A had been confirmed (Stein G H et al., J. Cell Physiol., 99: 43-54 (1979), purchased from ATCC), were collected, and 100 μCi of chromium 51 was added to the tube, followed by incubation at 37° C. for 2 hours. Subsequently, the cells were washed 3 times with AIM-V medium supplemented with 10% human AB serum, and placed in a 96-well V-bottomed plate in an amount of $10^3$ cells per well, followed by further addition, to each well, of $10^5$, $5\times10^4$, $2.5\times10^4$ or $1.25\times10^4$ HLA-A0201-positive CD8-positive T cells suspended in AIM-V medium supplemented with 10% human AB serum, which cells were stimulated with the respective polypeptides shown in SEQ ID NOs:27 to 35. The cells were then cultured at 37° C. under 5% $CO_2$ for 4 hours. Thereafter, the amount of chromium 51 released from damaged tumor cells into the culture supernatant was measured, and thereby the cytotoxic activity of the CD8-positive T cells stimulated with each of the polypeptides shown in SEQ ID NOs:27 to 35 was calculated.

Figure 13:
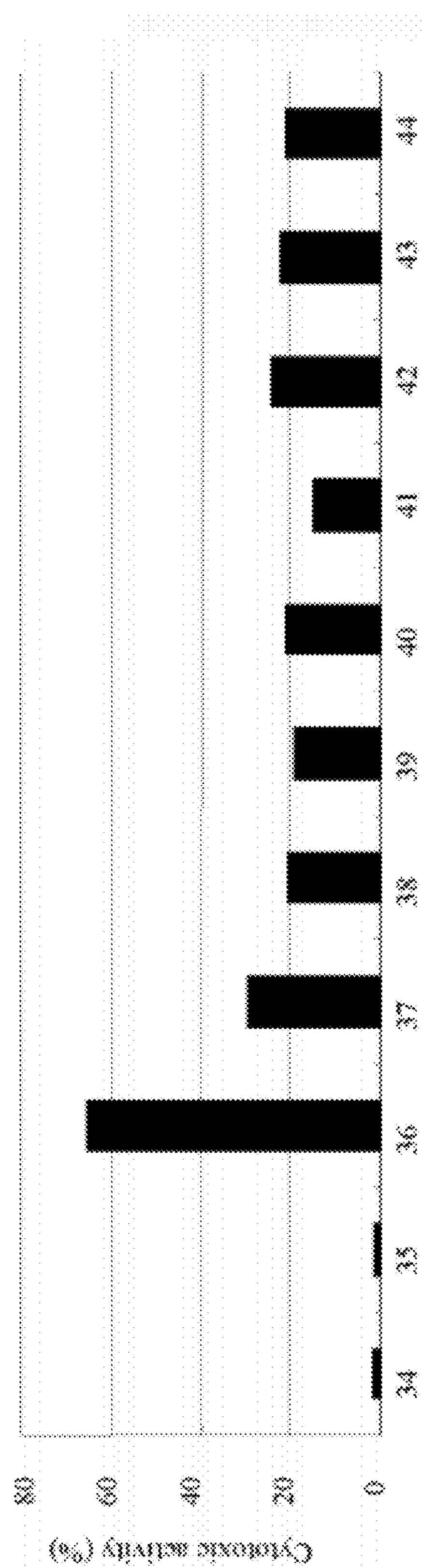
FIG. 13 is a diagram showing the cytotoxic activities, against cancer cells, of CD8-positive T cells specific to each of the polypeptides having the amino acid sequences shown in SEQ ID NOs:27 to 35 in SEQUENCE LISTING.

As a result, it was revealed that the HLA-A0201-positive CD8-positive T cells stimulated with the respective polypeptides shown in SEQ ID NOs:27 to 35 have the cytotoxic activity against T98G (FIG. 13). Therefore, it became clear that the polypeptides shown in SEQ ID NOs:27 to 35, which are polypeptide to be used in the present invention, are presented on HLA-A0201 molecules on HLA-A0201-positive tumor cells expressing PDS5A, and that these polypeptides have a capacity to induce CD8-positive cytotoxic T cells which can damage such tumor cells. On the other hand, in the case where the polypeptide having the amino acid sequence shown in SEQ ID NO:36, which is outside the scope of the present invention, was added to perform the above-described treatment, no cytotoxic activity could be observed (FIG. 13).

The cytotoxic activity was determined by, as described above, mixing $10^5$ CD8-positive T cells stimulated and induced with each of the peptides of the present invention and $10^3$ cells of a malignant brain tumor cell line T98G to which chromium 51 was incorporated; culturing the resultant for 4 hours; measuring the amount of chromium 51 released into the culture medium after the culturing; and calculating the cytotoxic activity of the CD8-positive T cells against T98G according to the following equation*.

cytotoxic activity(%)=(Amount of chromium 51 released from T98G when CD8-positive T cells were added)/(Amount of chromium 51 released from the target cells to which 1N hydrochloric acid was added)×100. *Equation:

Example 5

Preparation, and Evaluation of Pharmacological Effect, of Recombinant PDS5A Protein; Detection of Cancer; and Cancer Diagnosis (1) Preparation of Recombinant PDS5A Protein Based on the gene of SEQ ID NO:1 obtained in Example 1, a recombinant protein was prepared by the following method. Regents and an attached buffer were mixed such that 1 μl of the vector obtained in Example 1 which was prepared from the phagemid solution and subjected to the sequence analysis, 0.4 μM each of two kinds of primers having the NotI and XhoI restriction sites (shown in SEQ ID NOs:37 and 38), 0.2 mM dNTP and 1.25 U PrimeSTAR HS polymerase (manufactured by Takara Shuzo Co., Ltd.) were contained in a total volume of 50 μl, and PCR was carried out by repeating 30 times the cycle of 98° C. for 10 seconds, 55° C. for 15 seconds and 72° C. for 4 minute using a Thermal Cycler (manufactured by BIO RAD). The above-described two kinds of primers were those for amplification of the region encoding the full-length of the amino acid sequence shown in SEQ ID NO:2. After the PCR, the amplified DNA was subjected to electrophoresis using 1% agarose gel, and a DNA fragment of about 4000 bp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and the plasmid was then recovered. The amplified gene fragment was confirmed to have the same sequence as that of interest by sequencing. The plasmid having the same sequence as that of interest was treated with restriction enzymes NotI and XhoI, and purified using QIAquick Gel Extraction Kit, followed by inserting the gene sequence of interest into an expression vector for *E. coli*, pET30a (manufactured by Novagen) that had been treated with restriction enzymes NotI and XhoI. Use of this vector enables production of a His tag-fused recombinant protein. *E. coli* for expression, BL21 (DE3), was transformed with this plasmid, and expression was induced with 1 mM IPTG, to allow expression of the protein of interest in *E. coli.*

Further, based on the gene of SEQ ID NO:43, a recombinant protein of human PDS5A was prepared by the following method. Regents and an attached buffer were mixed such that 1 μl of the cDNA prepared in Example 1 whose expression could be confirmed with cDNAs from various tissues and cells by the RT-PCR method, 0.4 μM each of two kinds of primers having the NotI and XhoI restriction sites (shown in SEQ ID NOs:39 and 40), 0.2 mM dNTP and 1.25 U PrimeSTAR HS polymerase (manufactured by Takara Shuzo Co., Ltd.) were contained in a total volume of 50 μl, and PCR was carried out by repeating 30 times the cycle of 98° C. for 10 seconds, 55° C. for 15 seconds and 72° C. for 4 minute using a Thermal Cycler (manufactured by BIO RAD). The above-described two kinds of primers were those for amplification of the region encoding the full-length of the amino acid sequence shown in SEQ ID NO:44. After the PCR, the amplified DNA was subjected to electrophoresis using 1% agarose gel, and a DNA fragment of about 4000 bp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, and the plasmid was then recovered. The amplified gene fragment was confirmed to have the same sequence as that of interest by sequencing. The plasmid having the same sequence as that of interest was treated with restriction enzymes NotI and XhoI, and purified using QIAquick Gel Extraction Kit, followed by inserting the gene sequence of interest into an expression vector for *E. coli*, pET30a (manufactured by Novagen) that had been treated with restriction enzymes NotI and XhoI. Use of this vector enables production of a His tag-fused recombinant protein. *E. coli* for expression, BL21 (DE3), was transformed with this plasmid, and expression was induced with 1 mM IPTG, to allow expression of the protein of interest in *E. coli.*

Further, based on the gene of SEQ ID NO:5, a recombinant protein of murine PDS5A was prepared by the following method. Regents and an attached buffer were mixed such that 1 μl of the cDNA prepared in Example 1 whose expression could be confirmed with cDNAs from various tissues and cells by the RT-PCR method, 0.4 μM each of two kinds of primers having the NotI and XhoI restriction sites (shown in SEQ ID NOs:41 and 42), 0.2 mM dNTP and 1.25 U PrimeSTAR HS polymerase (manufactured by Takara Shuzo Co., Ltd.) were contained in a total volume of 50 μl, and PCR was carried out by repeating 30 times the cycle of 98° C. for 10 seconds, 55° C. for 15 seconds and 72° C. for 4 minute using a Thermal Cycler (manufactured by BIO RAD). The above-described two kinds of primers were those for amplification of the region encoding the full-length of the amino acid sequence shown in SEQ ID NO:6. After the PCR, the amplified DNA was subjected to electrophoresis using 1% agarose gel, and a DNA fragment of about 4000 bp was purified using QIAquick Gel Extraction Kit (manufactured by QIAGEN).

The purified DNA fragment was ligated into a cloning vector pCR-Blunt (manufactured by Invitrogen). *E. coli* was transformed with the resulting ligation product, the plasmid was then recovered. The amplified gene fragment was confirmed to have the same sequence as that of interest by sequencing. The plasmid having the same sequence as that of interest was treated with restriction enzymes NotI and XhoI, and purified using QIAquick Gel Extraction Kit, followed by inserting the gene sequence of interest into an expression vector for *E. coli*, pET30a (manufactured by Novagen) that had been treated with restriction enzymes NotI and XhoI. Use of this vector enables production of a His tag-fused recombinant protein. *E. coli* for expression, BL21 (DE3), was transformed with this plasmid, and expression was induced with 1 mM IPTG, to allow expression of the protein of interest in *E. coli.*

(2) Purification of PDS5A Protein

Each of the above obtained recombinant *E. coli* that expresses SEQ ID NO:2, SEQ ID NO:44 or SEQ ID NO:6 was cultured in LB medium supplemented with 100 μg/ml ampicillin at 37° C. until the absorbance at 600 nm reached about 0.7, and then isopropyl-β-D-1-thiogalactopyranoside was added thereto to a final concentration of 1 mM, followed by further culturing the recombinant *E. coli* at 37° C. for 4 hours. Subsequently, the bacterial cells were collected by centrifugation at 4,800 rpm for 10 minutes. The pellet of the cells was suspended in phosphate-buffered saline and father subjected to centrifugation at 4,800 rpm for 10 minutes to wash the bacterial cells.

The bacterial cells were suspended in 50 mM Tris-HCl buffer (pH 8.0) and subjected to sonication on ice. The liquid obtained by the sonication of *E. coli* was centrifuged at 6000 rpm for 20 minutes, to obtain the supernatant as the soluble fraction and the precipitate as the insoluble fraction.

The insoluble fraction was suspended in 50 mM Tris-HCl buffer (pH 8.0) and centrifuged at 6000 rpm for 15 minutes. This operation was repeated twice to perform an operation of removal of proteases.

The residue was suspended in 50 mM Tris-HCl buffer (pH 8.0) supplemented with 6 M guanidine hydrochloride and 0.15 M sodium chloride, and left to stand at 4° C. for 20 hours to denature proteins. Thereafter, the suspension was centrifuged at 6000 rpm for 30 minutes, and the obtained soluble fraction was placed in a nickel chelate column prepared by a conventional method (carrier: Chelating Sepharose (trademark) Fast Flow (GE Health Care); column volume: 5 mL; equilibration buffer: 50 mM Tris-HCl buffer (pH 8.0) supplemented with 6M guanidine hydrochloride and 0.15 M sodium chloride), followed by leaving the resultant to stand at 4° C. overnight to allow adsorption of the proteins to the nickel-chelated carrier. This column carrier was centrifuged at 1500 rpm for 5 minutes and the supernatant was then recovered. The column carrier was suspended in phosphate-buffered saline and refilled into the column.

The fraction not adsorbed to the column was washed with 10 column volumes of 0.1 M acetate buffer (pH 4.0) supplemented with 0.5 M sodium chloride, and immediately thereafter, proteins were eluted with 0.1 M acetate buffer (pH 3.0) supplemented with 0.5 M sodium chloride, to obtain a purified fraction, which was used later as a material for an administration test. The protein of interest in each eluted fraction was confirmed by Coomassie staining carried out according to a conventional method.

The buffer of the purified preparation obtained by the above method was replaced with a reaction buffer (50 mM Tris-HCl, 100 mM NaCl, 5 mM $CaCl_2$ (pH8.0)), and the resulting sample was subjected to cleavage of the His tag with factor Xa protease and purification of the protein of interest, using Factor Xa Cleavage Capture Kit (manufactured by Novagen) in accordance with the protocol attached to the kit. Subsequently, the buffer of 12 ml of the purified preparation obtained by the above method was replaced with a physiological phosphate buffer (manufactured by Nissui Pharmaceutical) using ultrafiltration NANOSEP 10K OMEGA (manufactured by PALL), and the resulting sample was subjected to aseptic filtration through HT Tuffryn Acrodisc 0.22 µm (manufactured by PALL) and used in the experiment.

(3) Anti-Tumor Effect of Recombinant Murine PDS5A Protein in Tumor-Bearing Mouse The murine neuroblastoma cell line N2a was subcutaneously transplanted to A/J mice (7 weeks old, male, purchased from Japan SLC) in an amount of $1\times10^6$ cells. When the tumor volume reached an average of 50 to 100 $mm^3$ (typically 7 days after the inoculation of the tumor), the mice were randomly divided into groups each of which contains 10 individuals, and subjected to evaluation of the anti-tumor effect of the recombinant murine PDS5A protein (therapeutic model). With 100 µg (0.5 ml) of the recombinant murine PDS5A protein purified as described above, 50 µg of poly I:C was mixed to prepare a therapeutic agent for cancer, and this therapeutic agent was subcutaneously administered to the tumor-bearing mice a total of 3 times at intervals of 1 week. As a result, on Day 31 after the administration of the therapeutic agent for cancer, complete regression of the tumor was achieved. On the other hand, in the negative control group to which PBS(−) was administered and the group to which poly I:C alone (50 µg) was administered, the mean tumor volumes on Day 31 after the administration were 1657 $mm^3$ and 932 $mm^3$, respectively.

Further, a therapeutic agent for cancer wherein 100 µg (0.5 ml) of the recombinant murine PDS5A protein and 50 µg poly I:C were mixed was prepared, and subcutaneously administered to A/J mice a total of 3 times at intervals of 1 week, followed by transplantation of $1\times10^6$ N2a cells to the mice and evaluation of the anti-tumor effect (prophylactic model). Ten individuals were included in each group, and, as controls for comparison, a negative control group to which PBS(−) was administered and a group to which poly I:C alone (50 µg) was administered were provided. As a result, in the group to which the therapeutic agent for cancer was administered, no development of a tumor was observed even on Day 40 after the administration of the therapeutic agent for cancer. On the other hand, in the negative control group to which PBS(−) was administered and the group to which poly I:C alone (50 µg) was administered, the mean tumor volumes on Day 40 after the administration were 1989 $mm^3$ and 1843 $mm^3$, respectively.

The same experiment was carried out also for a colon cancer model. The colon cancer cell line CT26 was subcutaneously transplanted to Balb/c mice (7 weeks old, male, purchased from Japan SLC) in an amount of $1\times10^6$ cells. When the tumor volume reached an average of 50 to 100 $mm^3$ (typically 7 days after the inoculation of the tumor), the mice were randomly divided into groups each of which contains 10 individuals, and subjected to evaluation of the anti-tumor effect of the recombinant murine PDS5A protein (therapeutic model). With 100 µg (0.5 ml) of the recombinant murine PDS5A protein purified as described above, 50 µg of poly I:C was mixed to prepare a therapeutic agent for cancer, and this therapeutic agent was subcutaneously administered to the tumor-bearing mice a total of 3 times at intervals of 1 week. As a result, on Day 24 after the administration of the therapeutic agent for cancer, complete regression of the tumor was achieved. On the other hand, in the negative control group to which PBS(−) was administered and the group to which poly I:C alone (50 µg) was administered, the mean tumor volumes on Day 24 after the administration were 1449 $mm^3$ and 835 $mm^3$, respectively.

Further, a therapeutic agent for cancer wherein 100 µg (0.5 ml) of the recombinant murine PDS5A protein and 50 µg poly I:C were mixed was prepared, and subcutaneously administered to Balb/c mice a total of 3 times at intervals of 1 week, followed by transplantation of $1\times10^6$ CT26 cells to the mice and evaluation of the anti-tumor effect (prophylactic model). Ten individuals were included in each group, and, as controls for comparison, a negative control group to which PBS(−) was administered and a group to which poly I:C alone (50 µg) was administered were provided. As a result, in the group to which the therapeutic agent for cancer was administered, no development of a tumor was observed even on Day 31 after the administration of the therapeutic agent for cancer. On the other hand, in the negative control group to which PBS(−) was administered and the group to which poly I:C alone (50 µg) was administered, the mean tumor volumes on Day 31 after the administration were 1781 $mm^3$ and 1675 $mm^3$, respectively.

From these results, it was revealed that the recombinant PDS5A protein is effective for therapy and prophylaxis of cancer.

(4) Anti-Tumor Effect of Recombinant PDS5A Protein in Tumor-Bearing Dog

The anti-tumor effect of the recombinant protein described in Example 5 below in 3 individuals of tumor-bearing patient dogs (3 individuals having a mammary gland tumor) having a tumor mass in the epidermis was evaluated. Before administration, the antibody titer against the recombinant protein in the serum of each patient dog was measured by the method described in Example 5 (3), and, as a result, an antibody titer higher than that of a healthy dog was detected. From these results, it was suggested that the protein having the amino acid sequence shown in SEQ ID NO:2 was expressed as a cancer antigen in the tumor tissue in the living body of these tumor-bearing patient dogs.

With 500 µg (2.5 ml) each of the recombinant PDS5A proteins (dog-derived and human-derived) purified as described above, the same amount of Freund's incomplete adjuvant (manufactured by Wako Pure Chemical Industries, Ltd.) was mixed to prepare 2 kinds of therapeutic agents for cancer, each of which was administered to a regional lymph node in the vicinity of the tumor a total of 3 times at 1-week intervals. As a result, complete regression of the tumor, which had had a size of about 500 $mm^3$ or 1000 $mm^3$ at the time of administration of each therapeutic agent for cancer, was achieved on Day 13 or Day 21, respectively. On the other hand, in the negative control group to which PBS(−) was administered, the tumor volume, which had been about 800 $mm^3$ at the time of administration of PBS, became 1625 $mm^3$ on Day 21 after the administration.

With 500 µg (2.5 ml) of the canine recombinant PDS5A protein purified as described in Example 5 below, the same amount of Freund's incomplete adjuvant (manufactured by Wako Pure Chemical Industries, Ltd.) was mixed to prepare a therapeutic agent for cancer, and this therapeutic agent was subcutaneously administered in the vicinity of the tumor in 1 individual each of patient dogs suffering from perianal adenocarcinoma and epidermal squamous cell carcinoma a total of 4 times at 1-week interval. As a result, complete regression of the tumor, which had had a size of about 370 $mm^3$ or 280 $mm^3$, respectively, at the time of administration of the therapeutic agent for cancer, was achieved on Day 35 or Day 42, respectively.

(5) Detection of Cancer Using Recombinant PDS5A Protein

Blood was collected from 112 patient dogs wherein malignant tumor was found and 30 healthy dogs, and sera were separated therefrom. Using the canine PDS5A protein (SEQ ID NO:2) prepared in the above-described (2), the titer of antibodies specifically reactive with the protein in each serum was measured by the ELISA method. Immobilization of the prepared protein was carried out by placing 100 μL/well of the recombinant protein solution diluted to 5 μg/mL with phosphate-buffered saline in a 96-well Immobilizer Amino plate (manufactured by Nunc), followed by leaving the plate to stand at 4° C. overnight. Blocking was carried out by adding 100 μL of 50 mM sodium bicarbonate buffer (pH 8.4) supplemented with 3% BSA (bovine serum albumin, manufactured by Sigma-Aldrich Co.) (hereinafter referred to as the blocking solution) to each well and shaking the plate at room temperature for 1 hour. The sera were 1000-fold diluted with the blocking solution and added to the wells in an amount of 100 μL/well, and the plate was shaken at room temperature for 3 hours to allow the reaction to proceed. The wells were washed 3 times with phosphate-buffered saline supplemented with 0.05% Tween 20 (manufactured by Wako Pure Chemical Industries, Ltd.) (hereinafter referred to as PBS-T), and 100 μL/well of an HRP-modified anti-dog IgG antibody (Goat anti Dog IgG-h+I HRP conjugated: manufactured by BETHYL Laboratories) 3000-fold diluted with the blocking solution was added thereto, followed by shaking the plate at room temperature for 1 hour to allow the reaction to proceed. After washing the wells 3 times with PBS-T, 100 μl/well of an HRP substrate TMB (1-Step Turbo TMB (tetramethylbenzidine), PIERCE) was added, and the enzyme-substrate reaction was allowed to proceed at room temperature for 30 minutes. Thereafter, 100 μl/well of 0.5 M sulfuric acid solution (manufactured by Sigma-Aldrich Japan) was added to the wells to stop the reaction, and the absorbance at 450 nm was measured using a microplate reader. To prepare controls for comparison, experiments were carried out in the same manner as described above except that the prepared recombinant protein was not immobilized or except that the tumor-bearing dog serum was not reacted.

All the 112 samples used for the above-described cancer diagnosis were those which had been definitely diagnosed as malignant by pathological diagnosis using extirpated tumor tissues.

Specifically, the samples were those diagnosed as cancers such as malignant melanoma, malignant mixed tumor, hepatocellular carcinoma, basal cell carcinoma, intraoral tumor, perianal adenocarcinoma, anal sac tumor, anal sac apocrine carcinoma, Sertoli cell tumor, vulva cancer, sebaceous adenocarcinoma, sebaceous epithelioma, sebaceous adenoma, sweat gland carcinoma, intranasal adenocarcinoma, nasal adenocarcinoma, thyroid cancer, colon cancer, bronchial adenocarcinoma, adenocarcinoma, ductal carcinoma, mammary adenocarcinoma, combined mammary adenocarcinoma, mammary gland malignant mixed tumor, intraductal papillary adenocarcinoma, fibrosarcoma, hemangiopericytoma, osteosarcoma, chondrosarcoma, soft tissue sarcoma, histiocytic sarcoma, myxosarcoma, undifferentiated sarcoma, lung cancer, mastocytoma, cutaneous leiomyoma, intra-abdominal leiomyoma, leiomyoma, squamous cell carcinoma, chronic lymphocytic leukemia, lymphoma, gastrointestinal lymphoma, digestive organ lymphoma, small cell or medium cell lymphoma, adrenomedullary tumor, granulosa cell tumor and pheochromocytoma.

Sera from these cancer-bearing dogs showed significantly higher antibody titers against the recombinant protein than sera from the healthy dogs. It was revealed that, by diagnosing a sample showing a value not less than twice as high as the average value in healthy dogs as malignant, 94 samples, which corresponds to 83.9% of the malignant cases, could be successfully diagnosed as malignant. The types of the cancers in these 94 samples were as described below. It should be noted that, although a part of the samples were suffering from a plurality of types of cancers, each value shown below is the cumulative total for each type of cancer.

Malignant melanoma, 5 cases; lymphoma, 10 cases; granulosa cell tumor, 1 case; hepatocellular carcinoma, 3 cases; malignant testicular tumor, 3 cases; intraoral tumor, 3 cases; perianal adenocarcinoma, 5 cases; sarcoma, 9 cases; mammary adenocarcinoma, 35 cases; lung cancer, 1 case; ductal carcinoma, 4 cases; sebaceous adenocarcinoma, 2 cases; mastocytoma, 5 cases; leiomyosarcoma, 1 case; squamous cell carcinoma, 4 cases; malignant mixed tumor, 2 cases; and hemangiopericytoma, 1 case.

When cancer diagnosis was carried out in the same manner as described above using the human PDS5A protein (SEQ ID NO:44) prepared in the above-described (2), a similar result was obtained.

From the above results, it was revealed that, by using the PDS5A protein to measure the titer of antibodies specifically reactive with the protein in the serum, detection and diagnosis of cancer is possible.

INDUSTRIAL APPLICABILITY

The immunity-inducing agent of the present invention comprising a polypeptide that exerts an anti-tumor activity against various types of cancers is useful for therapy and/or prophylaxis of cancer, and/or detection of cancer.

The invention claimed is:

1. A method for immunity for therapy of a cancer in an animal, said method comprising: detecting antibodies against SEQ ID NO: 44 in a patient sample from an individual with cancer wherein the patient sample from said individual with cancer comprises antibodies against SEQ ID NO: 44 at a level which is higher than that level of antibodies in a patient sample from a healthy individual; and administering a daily dose to said individual with cancer of a polypeptide comprising SEQ ID NO: 44 said polypeptide having an immunity-inducing activity/activities, wherein said daily dose comprises from 0.0001 μg to 1000 μg of the polypeptide.

* * * * *

SEQUENCE LISTING

```
<160> NUMBER OF SEQ ID NOS: 44

<210> SEQ ID NO 1
<211> LENGTH: 4396
<212> TYPE: DNA
<213> ORGANISM: Canis familiaris
<220> FEATURE:
<221> NAME/KEY: CDS
<222> LOCATION: (116)..(4129)
```

```
<223> OTHER INFORMATION:

<400> SEQUENCE: 1

ccgacgaggg gcggcggcac aaccaccaga caaaggcccg ggcgctcgat gcaccttccg      60

ccccatgagg aggaggagcc ggtagaggac tgtgaaagaa aagttgtccc ccagg atg      118
                                                             Met
                                                             1

gac ttc acc gcg cag ccc aag cct gcc act gcc ctc tgt ggc gtc gtg      166
Asp Phe Thr Ala Gln Pro Lys Pro Ala Thr Ala Leu Cys Gly Val Val
            5                   10                  15

agt gca gac ggg aag atc gct tac cct ccg ggg gta aag gag atc acc      214
Ser Ala Asp Gly Lys Ile Ala Tyr Pro Pro Gly Val Lys Glu Ile Thr
        20                  25                  30

gac aag atc acc acc gat gaa atg atc aag cga ctg aag atg gta gta      262
Asp Lys Ile Thr Thr Asp Glu Met Ile Lys Arg Leu Lys Met Val Val
    35                  40                  45

aaa act ttt atg gat atg gat cag gac tca gaa gat gaa aaa cag cag      310
Lys Thr Phe Met Asp Met Asp Gln Asp Ser Glu Asp Glu Lys Gln Gln
50                  55                  60                  65

tat ctc cca cta gcc ttg cat ctt gca tct gaa ttt ttc ctc agg aat      358
Tyr Leu Pro Leu Ala Leu His Leu Ala Ser Glu Phe Phe Leu Arg Asn
                70                  75                  80

ccc aat aaa gat gtg cgt ctc ctt gta gca tgt tgt ttg gcc gac att      406
Pro Asn Lys Asp Val Arg Leu Leu Val Ala Cys Cys Leu Ala Asp Ile
            85                  90                  95

ttt cga atc tat gcc cca gaa gct cca tat act tcc cat gat aaa ctt      454
Phe Arg Ile Tyr Ala Pro Glu Ala Pro Tyr Thr Ser His Asp Lys Leu
        100                 105                 110

aag gac ata ttt ttg ttt att acc aga caa tta aaa ggt ttg gag gat      502
Lys Asp Ile Phe Leu Phe Ile Thr Arg Gln Leu Lys Gly Leu Glu Asp
    115                 120                 125

aca aag agt cca cag ttt aat aga tac ttt tat tta tta gag aac tta      550
Thr Lys Ser Pro Gln Phe Asn Arg Tyr Phe Tyr Leu Leu Glu Asn Leu
130                 135                 140                 145

gct tgg gtt aaa tcc tat aac atc tgc ttc gaa ttg gaa gat tgc aat      598
Ala Trp Val Lys Ser Tyr Asn Ile Cys Phe Glu Leu Glu Asp Cys Asn
                150                 155                 160

gaa att ttt att cag ctt ttt agg act ctc ttc tca gtg atc aac aat      646
Glu Ile Phe Ile Gln Leu Phe Arg Thr Leu Phe Ser Val Ile Asn Asn
            165                 170                 175

agc cac aat aag aag gta caa atg cac atg tta gac ttg atg agt tct      694
Ser His Asn Lys Lys Val Gln Met His Met Leu Asp Leu Met Ser Ser
        180                 185                 190

atc atc atg gaa ggt gat gga gtt act caa gaa tta ctg gac tcc att      742
Ile Ile Met Glu Gly Asp Gly Val Thr Gln Glu Leu Leu Asp Ser Ile
    195                 200                 205

ctt att aac ctc att cct gca cat aag aac tta aat aaa cag tcc ttt      790
Leu Ile Asn Leu Ile Pro Ala His Lys Asn Leu Asn Lys Gln Ser Phe
210                 215                 220                 225

gac ctt gca aaa gtc tta ttg aaa agg aca gtc cag acc att gag gca      838
Asp Leu Ala Lys Val Leu Leu Lys Arg Thr Val Gln Thr Ile Glu Ala
                230                 235                 240

tgc att gcc aat ttt ttc aat caa gtc ctg gtg ctg gga aga tcg tcc      886
Cys Ile Ala Asn Phe Phe Asn Gln Val Leu Val Leu Gly Arg Ser Ser
            245                 250                 255

gta agt gat ttg tca gaa cat gta ttt gat ctg att cag gaa ctt ttt      934
Val Ser Asp Leu Ser Glu His Val Phe Asp Leu Ile Gln Glu Leu Phe
        260                 265                 270

gca ata gat cct cat tta tta ttg tct gtc atg ccg cag ctt gaa ttc      982
```

```
Ala Ile Asp Pro His Leu Leu Leu Ser Val Met Pro Gln Leu Glu Phe
    275                 280                 285

aaa cta aag agc aat gat gga gaa gag cga tta gct gtt gtt cga ctt      1030
Lys Leu Lys Ser Asn Asp Gly Glu Glu Arg Leu Ala Val Val Arg Leu
290                 295                 300                 305

tta gct aaa ttg ttt ggt tct aaa gat tct gat ttg gca aca cag aat      1078
Leu Ala Lys Leu Phe Gly Ser Lys Asp Ser Asp Leu Ala Thr Gln Asn
                310                 315                 320

cgt cct ctt tgg cag tgt ttt ctt gga cga ttt aat gac att cat gtt      1126
Arg Pro Leu Trp Gln Cys Phe Leu Gly Arg Phe Asn Asp Ile His Val
            325                 330                 335

cct gtg aga tta gaa agt gtg aaa ttt gcc agt cac tgt tta atg aat      1174
Pro Val Arg Leu Glu Ser Val Lys Phe Ala Ser His Cys Leu Met Asn
        340                 345                 350

cac cca gat tta gca aag gat ctc aca gaa tat ttg aaa gtt aga tcc      1222
His Pro Asp Leu Ala Lys Asp Leu Thr Glu Tyr Leu Lys Val Arg Ser
    355                 360                 365

cat gat ccc gaa gag gct att cgt cat gat gtc att gtt act ata ata      1270
His Asp Pro Glu Glu Ala Ile Arg His Asp Val Ile Val Thr Ile Ile
370                 375                 380                 385

aca gct gcc aaa aga gac ctt gcc tta gta aat gat caa cta ctt ggc      1318
Thr Ala Ala Lys Arg Asp Leu Ala Leu Val Asn Asp Gln Leu Leu Gly
                390                 395                 400

ttt gta aga gaa aga aca ctg gat aaa cgg tgg cga gta aga aaa gaa      1366
Phe Val Arg Glu Arg Thr Leu Asp Lys Arg Trp Arg Val Arg Lys Glu
            405                 410                 415

gct atg atg ggt ctg gct cag ctc tat aag aaa tac tgt ctt cat ggt      1414
Ala Met Met Gly Leu Ala Gln Leu Tyr Lys Lys Tyr Cys Leu His Gly
        420                 425                 430

gaa gca gga aag gaa gct gca gag aaa gtc agc tgg ata aag gac aaa      1462
Glu Ala Gly Lys Glu Ala Ala Glu Lys Val Ser Trp Ile Lys Asp Lys
    435                 440                 445

ctt ttg cat att tat tat caa aat agc atc gat gac aaa ctg ttg gta      1510
Leu Leu His Ile Tyr Tyr Gln Asn Ser Ile Asp Asp Lys Leu Leu Val
450                 455                 460                 465

gag aaa atc ttt gct cag tat ctt gtc ccc cac aac ctg gaa aca gaa      1558
Glu Lys Ile Phe Ala Gln Tyr Leu Val Pro His Asn Leu Glu Thr Glu
                470                 475                 480

gag aga atg aaa tgc ttg tat tat tta tac gct agt ttg gat cca aat      1606
Glu Arg Met Lys Cys Leu Tyr Tyr Leu Tyr Ala Ser Leu Asp Pro Asn
            485                 490                 495

gct gtc aaa gct ctc aat gaa atg tgg aaa tgt cag aac atg ctt cga      1654
Ala Val Lys Ala Leu Asn Glu Met Trp Lys Cys Gln Asn Met Leu Arg
        500                 505                 510

agt cat gta cga gaa ctc ttg gat ttg cac aag caa cct aca tca gag      1702
Ser His Val Arg Glu Leu Leu Asp Leu His Lys Gln Pro Thr Ser Glu
    515                 520                 525

gct aac tgt tct gcc atg ttt gga aaa ctg atg acc ata gca aag aat      1750
Ala Asn Cys Ser Ala Met Phe Gly Lys Leu Met Thr Ile Ala Lys Asn
530                 535                 540                 545

ttg cct gac cct ggg aaa gca caa gat ttt gtg aag aaa ttt aac cag      1798
Leu Pro Asp Pro Gly Lys Ala Gln Asp Phe Val Lys Lys Phe Asn Gln
                550                 555                 560

gtc ctt ggt gat gat gag aaa ttg cgg tct cag ctg gag tta cta atc      1846
Val Leu Gly Asp Asp Glu Lys Leu Arg Ser Gln Leu Glu Leu Leu Ile
            565                 570                 575

agc cca acc tgt tca tgc aaa caa gca gat gtt tgt gtg aga gaa ata      1894
Ser Pro Thr Cys Ser Cys Lys Gln Ala Asp Val Cys Val Arg Glu Ile
        580                 585                 590
```

```
gct cga aaa ctt gca aat cct aag cag cca aca aat cct ttt cta gag     1942
Ala Arg Lys Leu Ala Asn Pro Lys Gln Pro Thr Asn Pro Phe Leu Glu
    595                 600                 605

atg gtc aaa ttt ctg ttg gaa aga att gca cct gtg cac att gat tca     1990
Met Val Lys Phe Leu Leu Glu Arg Ile Ala Pro Val His Ile Asp Ser
610                 615                 620                 625

gaa gcc ata agt gca ctg gta aaa ctg atg aat aaa tca ata gaa ggg     2038
Glu Ala Ile Ser Ala Leu Val Lys Leu Met Asn Lys Ser Ile Glu Gly
                630                 635                 640

aca gca gat gat gaa gag gag ggt gta agt cca gat aca gct att cgt     2086
Thr Ala Asp Asp Glu Glu Glu Gly Val Ser Pro Asp Thr Ala Ile Arg
            645                 650                 655

tcg gga ctt gaa ctt ctt aag gtt ctg tct ttc aca cat cct acc tcg     2134
Ser Gly Leu Glu Leu Leu Lys Val Leu Ser Phe Thr His Pro Thr Ser
        660                 665                 670

ttc cac tct gca gag aca tat gag tcc ctg tta cag tgc ctc aga atg     2182
Phe His Ser Ala Glu Thr Tyr Glu Ser Leu Leu Gln Cys Leu Arg Met
    675                 680                 685

gaa gat gac aag gta gca gaa gct gct ata caa att ttt aga aat aca     2230
Glu Asp Asp Lys Val Ala Glu Ala Ala Ile Gln Ile Phe Arg Asn Thr
690                 695                 700                 705

ggc cac aaa ata gaa aca gac cta ccc cag ata cga tcg acc tta att     2278
Gly His Lys Ile Glu Thr Asp Leu Pro Gln Ile Arg Ser Thr Leu Ile
                710                 715                 720

ccc att tta cat cag aaa gca aag aga ggt act cca cat caa gca aaa     2326
Pro Ile Leu His Gln Lys Ala Lys Arg Gly Thr Pro His Gln Ala Lys
            725                 730                 735

cag gct gtt cac tgt ata cat gcc ata ttc aca aat aaa gaa gtc cag     2374
Gln Ala Val His Cys Ile His Ala Ile Phe Thr Asn Lys Glu Val Gln
        740                 745                 750

ctt gca cag att ttt gag cca ctc agt agg agt ctg aat gct gat gta     2422
Leu Ala Gln Ile Phe Glu Pro Leu Ser Arg Ser Leu Asn Ala Asp Val
    755                 760                 765

cca gaa caa ctt att act ccg tta gtt tca ttg ggc cac att tct atg     2470
Pro Glu Gln Leu Ile Thr Pro Leu Val Ser Leu Gly His Ile Ser Met
770                 775                 780                 785

tta gcc cca gat caa ttt gct tcc cca atg aaa tcc gta gta gca aat     2518
Leu Ala Pro Asp Gln Phe Ala Ser Pro Met Lys Ser Val Val Ala Asn
                790                 795                 800

ttt att gtg aaa gat ctg cta atg aat gac agg tca aca ggt gag aag     2566
Phe Ile Val Lys Asp Leu Leu Met Asn Asp Arg Ser Thr Gly Glu Lys
            805                 810                 815

aat gga aaa tta tgg tct cca gat gaa gag gtt tcc ccc gaa gta cta     2614
Asn Gly Lys Leu Trp Ser Pro Asp Glu Glu Val Ser Pro Glu Val Leu
        820                 825                 830

gca aag gta cag gca att aaa ctt ctg gta agg tgg ctg ttg ggt atg     2662
Ala Lys Val Gln Ala Ile Lys Leu Leu Val Arg Trp Leu Leu Gly Met
    835                 840                 845

aaa aac aac cag tct aaa tct gcc aat tca act ctt cga tta tta tca     2710
Lys Asn Asn Gln Ser Lys Ser Ala Asn Ser Thr Leu Arg Leu Leu Ser
850                 855                 860                 865

gcg atg ttg gtt agt gag ggt gac ctg aca gag caa aag agg atc agt     2758
Ala Met Leu Val Ser Glu Gly Asp Leu Thr Glu Gln Lys Arg Ile Ser
                870                 875                 880

aaa tct gat atg tct cgc ttg cga tta gct gct ggt agt gcc ata atg     2806
Lys Ser Asp Met Ser Arg Leu Arg Leu Ala Ala Gly Ser Ala Ile Met
            885                 890                 895

aag ctt gct cag gaa cct tgt tac cat gaa att ata act cca gaa cag     2854
Lys Leu Ala Gln Glu Pro Cys Tyr His Glu Ile Ile Thr Pro Glu Gln
        900                 905                 910
```

-continued

```
ttt cag ctc tgt gca ctt gtt att aac gat gag tgc tac caa gta agg      2902
Phe Gln Leu Cys Ala Leu Val Ile Asn Asp Glu Cys Tyr Gln Val Arg
    915                 920                 925

cag ata ttt gcc cag aag ttg cat aaa gct ctc gtg aag tta ctg ctg      2950
Gln Ile Phe Ala Gln Lys Leu His Lys Ala Leu Val Lys Leu Leu Leu
930                 935                 940                 945

cca ttg gaa tat atg gcg atc ttt gcc ttg tgt gcc aaa gat cct gtg      2998
Pro Leu Glu Tyr Met Ala Ile Phe Ala Leu Cys Ala Lys Asp Pro Val
                950                 955                 960

aag gag aga aga gca cat gca cga cag tgt tta cta aaa aat atc agt      3046
Lys Glu Arg Arg Ala His Ala Arg Gln Cys Leu Leu Lys Asn Ile Ser
            965                 970                 975

ata cgc agg gag tac att aaa cag aac ccc atg gct act gag aaa tta      3094
Ile Arg Arg Glu Tyr Ile Lys Gln Asn Pro Met Ala Thr Glu Lys Leu
        980                 985                 990

cta tca ctg ttg cct gaa tat  gta gtt cca tac atg  att cac ctg cta    3142
Leu Ser Leu Leu Pro Glu Tyr  Val Val Pro Tyr Met  Ile His Leu Leu
    995                 1000                1005

gcc  cat gat cca gat ttt  aca aga tca caa gat  gtt gat cag ctt      3187
Ala  His Asp Pro Asp Phe  Thr Arg Ser Gln Asp  Val Asp Gln Leu
1010                 1015                 1020

cgt  gat att aaa gag tgc  cta tgg ttc atg ctt  gaa gtt tta atg      3232
Arg  Asp Ile Lys Glu Cys  Leu Trp Phe Met Leu  Glu Val Leu Met
1025                 1030                 1035

aca  aag aat gaa aac aat  agc cat gca ttt atg  aag aag atg gca      3277
Thr  Lys Asn Glu Asn Asn  Ser His Ala Phe Met  Lys Lys Met Ala
1040                 1045                 1050

gag  aac atc aag tta aca  aaa gat gcc cag tct  cca gat gaa tcc      3322
Glu  Asn Ile Lys Leu Thr  Lys Asp Ala Gln Ser  Pro Asp Glu Ser
1055                 1060                 1065

aag  atg aat gaa aaa ctt  tat aca gta tgt gat  gtg gct ctg tgt      3367
Lys  Met Asn Glu Lys Leu  Tyr Thr Val Cys Asp  Val Ala Leu Cys
1070                 1075                 1080

gtt  ata aat agt aaa agt  gct ttg tgc aat gca  gat tca cca aag      3412
Val  Ile Asn Ser Lys Ser  Ala Leu Cys Asn Ala  Asp Ser Pro Lys
1085                 1090                 1095

gat  cca gtc ctt cca atg  aaa ttt ttt aca caa  cct gaa aag gat      3457
Asp  Pro Val Leu Pro Met  Lys Phe Phe Thr Gln  Pro Glu Lys Asp
1100                 1105                 1110

ttc  tgt aat gac aag agt  tat att tca gaa gag  acc aga gta ctt      3502
Phe  Cys Asn Asp Lys Ser  Tyr Ile Ser Glu Glu  Thr Arg Val Leu
1115                 1120                 1125

ctg  tta aca gga aag cca  aaa cct gct gga gta  cta ggt gca gta      3547
Leu  Leu Thr Gly Lys Pro  Lys Pro Ala Gly Val  Leu Gly Ala Val
1130                 1135                 1140

aac  aag cct tta tca gca  aca gga aga aaa cca  tat gta aga agc      3592
Asn  Lys Pro Leu Ser Ala  Thr Gly Arg Lys Pro  Tyr Val Arg Ser
1145                 1150                 1155

act  gga gct gag act gga  agc aat att aat gta  aat tca gag ctg      3637
Thr  Gly Ala Glu Thr Gly  Ser Asn Ile Asn Val  Asn Ser Glu Leu
1160                 1165                 1170

aac  cct tca acc gga aat  cga tca agg gaa caa  agt tca gag gca      3682
Asn  Pro Ser Thr Gly Asn  Arg Ser Arg Glu Gln  Ser Ser Glu Ala
1175                 1180                 1185

gta  gaa act gga gtt agt  gaa aat gaa gag aac  cct gtg aga att      3727
Val  Glu Thr Gly Val Ser  Glu Asn Glu Glu Asn  Pro Val Arg Ile
1190                 1195                 1200

att  tct gtc aca cct gta  aaa aat att gac cca  gta aag aat aag      3772
Ile  Ser Val Thr Pro Val  Lys Asn Ile Asp Pro  Val Lys Asn Lys
```

```
1205                1210                1215

gag  att aat tct gat cag  act acc cag ggc aac  atc agc agt gac      3817
Glu  Ile Asn Ser Asp Gln  Thr Thr Gln Gly Asn  Ile Ser Ser Asp
1220                1225                1230

cga  gga aag aag aga agt  gta gca gca gct ggt  aca gag aac atc      3862
Arg  Gly Lys Lys Arg Ser  Val Ala Ala Ala Gly  Thr Glu Asn Ile
1235                1240                1245

caa  caa aaa aca gat gag  aaa gta gac gaa tca  gga cca cct gcc      3907
Gln  Gln Lys Thr Asp Glu  Lys Val Asp Glu Ser  Gly Pro Pro Ala
1250                1255                1260

cct  tca aaa ccc agg aga  gga cgc cga ccc aag  tct gaa tct cag      3952
Pro  Ser Lys Pro Arg Arg  Gly Arg Arg Pro Lys  Ser Glu Ser Gln
1265                1270                1275

ggc  aat gca acc aaa aat  gat gac ata aac aaa  cct ctt ggc aag      3997
Gly  Asn Ala Thr Lys Asn  Asp Asp Ile Asn Lys  Pro Leu Gly Lys
1280                1285                1290

gga  aga aag aga gct gcg  gtc agt cag gaa agc  cct ggg ggt ctg      4042
Gly  Arg Lys Arg Ala Ala  Val Ser Gln Glu Ser  Pro Gly Gly Leu
1295                1300                1305

gaa  gca ggt aat gcc aaa  gca ccc aaa ctg caa  gat gta gcc aaa      4087
Glu  Ala Gly Asn Ala Lys  Ala Pro Lys Leu Gln  Asp Val Ala Lys
1310                1315                1320

aag  gca gta cca gca gag  aga cag att gac tta  caa agg taa          4129
Lys  Ala Val Pro Ala Glu  Arg Gln Ile Asp Leu  Gln Arg
1325                1330                1335

aaagaaaact catttgcaaa gggaaaaaat gaaggccaaa cagaagcaca gactccagct   4189

tctgcaaaaa cttggattca caatgtccct gaacagaaaa tgaagttaac ttcagaacac   4249

actttctgcc ttgaaaactg aaagaaacta ttacttcctt ttcacatgac cacaagtcct   4309

ttgatggaaa tgtacagaga aactcttgag agagagagag agagagagag agagagagag   4369

agaggctaaa agcaactcta ttctatc                                       4396


<210> SEQ ID NO 2
<211> LENGTH: 1337
<212> TYPE: PRT
<213> ORGANISM: Canis familiaris

<400> SEQUENCE: 2

Met Asp Phe Thr Ala Gln Pro Lys Pro Ala Thr Ala Leu Cys Gly Val
1               5                   10                  15

Val Ser Ala Asp Gly Lys Ile Ala Tyr Pro Pro Gly Val Lys Glu Ile
            20                  25                  30

Thr Asp Lys Ile Thr Thr Asp Glu Met Ile Lys Arg Leu Lys Met Val
        35                  40                  45

Val Lys Thr Phe Met Asp Met Asp Gln Asp Ser Glu Asp Glu Lys Gln
    50                  55                  60

Gln Tyr Leu Pro Leu Ala Leu His Leu Ala Ser Glu Phe Phe Leu Arg
65                  70                  75                  80

Asn Pro Asn Lys Asp Val Arg Leu Leu Val Ala Cys Cys Leu Ala Asp
                85                  90                  95

Ile Phe Arg Ile Tyr Ala Pro Glu Ala Pro Tyr Thr Ser His Asp Lys
            100                 105                 110

Leu Lys Asp Ile Phe Leu Phe Ile Thr Arg Gln Leu Lys Gly Leu Glu
        115                 120                 125

Asp Thr Lys Ser Pro Gln Phe Asn Arg Tyr Phe Tyr Leu Leu Glu Asn
    130                 135                 140
```

```
Leu Ala Trp Val Lys Ser Tyr Asn Ile Cys Phe Glu Leu Glu Asp Cys
145                 150                 155                 160

Asn Glu Ile Phe Ile Gln Leu Phe Arg Thr Leu Phe Ser Val Ile Asn
                165                 170                 175

Asn Ser His Asn Lys Lys Val Gln Met His Met Leu Asp Leu Met Ser
            180                 185                 190

Ser Ile Ile Met Glu Gly Asp Gly Val Thr Gln Glu Leu Leu Asp Ser
        195                 200                 205

Ile Leu Ile Asn Leu Ile Pro Ala His Lys Asn Leu Asn Lys Gln Ser
    210                 215                 220

Phe Asp Leu Ala Lys Val Leu Leu Lys Arg Thr Val Gln Thr Ile Glu
225                 230                 235                 240

Ala Cys Ile Ala Asn Phe Phe Asn Gln Val Leu Val Leu Gly Arg Ser
                245                 250                 255

Ser Val Ser Asp Leu Ser Glu His Val Phe Asp Leu Ile Gln Glu Leu
            260                 265                 270

Phe Ala Ile Asp Pro His Leu Leu Leu Ser Val Met Pro Gln Leu Glu
        275                 280                 285

Phe Lys Leu Lys Ser Asn Asp Gly Glu Glu Arg Leu Ala Val Val Arg
    290                 295                 300

Leu Leu Ala Lys Leu Phe Gly Ser Lys Asp Ser Asp Leu Ala Thr Gln
305                 310                 315                 320

Asn Arg Pro Leu Trp Gln Cys Phe Leu Gly Arg Phe Asn Asp Ile His
                325                 330                 335

Val Pro Val Arg Leu Glu Ser Val Lys Phe Ala Ser His Cys Leu Met
            340                 345                 350

Asn His Pro Asp Leu Ala Lys Asp Leu Thr Glu Tyr Leu Lys Val Arg
        355                 360                 365

Ser His Asp Pro Glu Glu Ala Ile Arg His Asp Val Ile Val Thr Ile
    370                 375                 380

Ile Thr Ala Ala Lys Arg Asp Leu Ala Leu Val Asn Asp Gln Leu Leu
385                 390                 395                 400

Gly Phe Val Arg Glu Arg Thr Leu Asp Lys Arg Trp Arg Val Arg Lys
                405                 410                 415

Glu Ala Met Met Gly Leu Ala Gln Leu Tyr Lys Lys Tyr Cys Leu His
            420                 425                 430

Gly Glu Ala Gly Lys Glu Ala Ala Glu Lys Val Ser Trp Ile Lys Asp
        435                 440                 445

Lys Leu Leu His Ile Tyr Tyr Gln Asn Ser Ile Asp Asp Lys Leu Leu
    450                 455                 460

Val Glu Lys Ile Phe Ala Gln Tyr Leu Val Pro His Asn Leu Glu Thr
465                 470                 475                 480

Glu Glu Arg Met Lys Cys Leu Tyr Tyr Leu Tyr Ala Ser Leu Asp Pro
                485                 490                 495

Asn Ala Val Lys Ala Leu Asn Glu Met Trp Lys Cys Gln Asn Met Leu
            500                 505                 510

Arg Ser His Val Arg Glu Leu Leu Asp Leu His Lys Gln Pro Thr Ser
        515                 520                 525

Glu Ala Asn Cys Ser Ala Met Phe Gly Lys Leu Met Thr Ile Ala Lys
    530                 535                 540

Asn Leu Pro Asp Pro Gly Lys Ala Gln Asp Phe Val Lys Lys Phe Asn
545                 550                 555                 560

Gln Val Leu Gly Asp Asp Glu Lys Leu Arg Ser Gln Leu Glu Leu Leu
```

```
                565                 570                 575

Ile Ser Pro Thr Cys Ser Cys Lys Gln Ala Asp Val Cys Val Arg Glu
            580                 585                 590

Ile Ala Arg Lys Leu Ala Asn Pro Lys Gln Pro Thr Asn Pro Phe Leu
        595                 600                 605

Glu Met Val Lys Phe Leu Leu Glu Arg Ile Ala Pro Val His Ile Asp
    610                 615                 620

Ser Glu Ala Ile Ser Ala Leu Val Lys Leu Met Asn Lys Ser Ile Glu
625                 630                 635                 640

Gly Thr Ala Asp Asp Glu Glu Glu Gly Val Ser Pro Asp Thr Ala Ile
                645                 650                 655

Arg Ser Gly Leu Glu Leu Leu Lys Val Leu Ser Phe Thr His Pro Thr
            660                 665                 670

Ser Phe His Ser Ala Glu Thr Tyr Glu Ser Leu Leu Gln Cys Leu Arg
        675                 680                 685

Met Glu Asp Asp Lys Val Ala Glu Ala Ala Ile Gln Ile Phe Arg Asn
    690                 695                 700

Thr Gly His Lys Ile Glu Thr Asp Leu Pro Gln Ile Arg Ser Thr Leu
705                 710                 715                 720

Ile Pro Ile Leu His Gln Lys Ala Lys Arg Gly Thr Pro His Gln Ala
                725                 730                 735

Lys Gln Ala Val His Cys Ile His Ala Ile Phe Thr Asn Lys Glu Val
            740                 745                 750

Gln Leu Ala Gln Ile Phe Glu Pro Leu Ser Arg Ser Leu Asn Ala Asp
        755                 760                 765

Val Pro Glu Gln Leu Ile Thr Pro Leu Val Ser Leu Gly His Ile Ser
    770                 775                 780

Met Leu Ala Pro Asp Gln Phe Ala Ser Pro Met Lys Ser Val Val Ala
785                 790                 795                 800

Asn Phe Ile Val Lys Asp Leu Leu Met Asn Asp Arg Ser Thr Gly Glu
                805                 810                 815

Lys Asn Gly Lys Leu Trp Ser Pro Asp Glu Glu Val Ser Pro Glu Val
            820                 825                 830

Leu Ala Lys Val Gln Ala Ile Lys Leu Leu Val Arg Trp Leu Leu Gly
        835                 840                 845

Met Lys Asn Asn Gln Ser Lys Ser Ala Asn Ser Thr Leu Arg Leu Leu
    850                 855                 860

Ser Ala Met Leu Val Ser Glu Gly Asp Leu Thr Glu Gln Lys Arg Ile
865                 870                 875                 880

Ser Lys Ser Asp Met Ser Arg Leu Arg Leu Ala Ala Gly Ser Ala Ile
                885                 890                 895

Met Lys Leu Ala Gln Glu Pro Cys Tyr His Glu Ile Ile Thr Pro Glu
            900                 905                 910

Gln Phe Gln Leu Cys Ala Leu Val Ile Asn Asp Glu Cys Tyr Gln Val
        915                 920                 925

Arg Gln Ile Phe Ala Gln Lys Leu His Lys Ala Leu Val Lys Leu Leu
    930                 935                 940

Leu Pro Leu Glu Tyr Met Ala Ile Phe Ala Leu Cys Ala Lys Asp Pro
945                 950                 955                 960

Val Lys Glu Arg Arg Ala His Ala Arg Gln Cys Leu Leu Lys Asn Ile
                965                 970                 975

Ser Ile Arg Arg Glu Tyr Ile Lys Gln Asn Pro Met Ala Thr Glu Lys
            980                 985                 990
```

```
Leu Leu Ser Leu Leu Pro Glu Tyr  Val Val Pro Tyr Met  Ile His Leu
        995                   1000                  1005

Leu Ala  His Asp Pro Asp Phe  Thr Arg Ser Gln Asp  Val Asp Gln
    1010                 1015                 1020

Leu Arg  Asp Ile Lys Glu Cys  Leu Trp Phe Met Leu  Glu Val Leu
    1025                 1030                 1035

Met Thr  Lys Asn Glu Asn Asn  Ser His Ala Phe Met  Lys Lys Met
    1040                 1045                 1050

Ala Glu  Asn Ile Lys Leu Thr  Lys Asp Ala Gln Ser  Pro Asp Glu
    1055                 1060                 1065

Ser Lys  Met Asn Glu Lys Leu  Tyr Thr Val Cys Asp  Val Ala Leu
    1070                 1075                 1080

Cys Val  Ile Asn Ser Lys Ser  Ala Leu Cys Asn Ala  Asp Ser Pro
    1085                 1090                 1095

Lys Asp  Pro Val Leu Pro Met  Lys Phe Phe Thr Gln  Pro Glu Lys
    1100                 1105                 1110

Asp Phe  Cys Asn Asp Lys Ser  Tyr Ile Ser Glu Glu  Thr Arg Val
    1115                 1120                 1125

Leu Leu  Leu Thr Gly Lys Pro  Lys Pro Ala Gly Val  Leu Gly Ala
    1130                 1135                 1140

Val Asn  Lys Pro Leu Ser Ala  Thr Gly Arg Lys Pro  Tyr Val Arg
    1145                 1150                 1155

Ser Thr  Gly Ala Glu Thr Gly  Ser Asn Ile Asn Val  Asn Ser Glu
    1160                 1165                 1170

Leu Asn  Pro Ser Thr Gly Asn  Arg Ser Arg Glu Gln  Ser Ser Glu
    1175                 1180                 1185

Ala Val  Glu Thr Gly Val Ser  Glu Asn Glu Glu Asn  Pro Val Arg
    1190                 1195                 1200

Ile Ile  Ser Val Thr Pro Val  Lys Asn Ile Asp Pro  Val Lys Asn
    1205                 1210                 1215

Lys Glu  Ile Asn Ser Asp Gln  Thr Thr Gln Gly Asn  Ile Ser Ser
    1220                 1225                 1230

Asp Arg  Gly Lys Lys Arg Ser  Val Ala Ala Ala Gly  Thr Glu Asn
    1235                 1240                 1245

Ile Gln  Gln Lys Thr Asp Glu  Lys Val Asp Glu Ser  Gly Pro Pro
    1250                 1255                 1260

Ala Pro  Ser Lys Pro Arg Arg  Gly Arg Arg Pro Lys  Ser Glu Ser
    1265                 1270                 1275

Gln Gly  Asn Ala Thr Lys Asn  Asp Asp Ile Asn Lys  Pro Leu Gly
    1280                 1285                 1290

Lys Gly  Arg Lys Arg Ala Ala  Val Ser Gln Glu Ser  Pro Gly Gly
    1295                 1300                 1305

Leu Glu  Ala Gly Asn Ala Lys  Ala Pro Lys Leu Gln  Asp Val Ala
    1310                 1315                 1320

Lys Lys  Ala Val Pro Ala Glu  Arg Gln Ile Asp Leu  Gln Arg
    1325                 1330                 1335


<210> SEQ ID NO 3
<211> LENGTH: 6726
<212> TYPE: DNA
<213> ORGANISM: Homo sapiens
<220> FEATURE:
<221> NAME/KEY: CDS
<222> LOCATION: (197)..(4090)
<223> OTHER INFORMATION:
```

<400> SEQUENCE: 3

```
ccggctcccg gggcacggac ggccgggcgc gcgcctctgc gaggggcgtc cgggtccgag     60

tcggcggtcc gggccggcgc gaggtgcgtg cgggcgggcc gcgggggtcc cggacggaca    120

caagcgcaca cactcccgga agatcgctta ccctccgggg gtaaaagaga tcaccgacaa    180

gatcaccacg gacgag atg atc aaa cgc ctg aag atg gta gtg aaa acc ttt    232
                  Met Ile Lys Arg Leu Lys Met Val Val Lys Thr Phe
                  1               5                   10

atg gat atg gat cag gac tca gaa gat gaa aaa cag cag tat ctc cca      280
Met Asp Met Asp Gln Asp Ser Glu Asp Glu Lys Gln Gln Tyr Leu Pro
        15                  20                  25

cta gcc ttg cat ctt gca tct gaa ttc ttc ctc agg aac ccc aat aaa      328
Leu Ala Leu His Leu Ala Ser Glu Phe Phe Leu Arg Asn Pro Asn Lys
    30                  35                  40

gat gtg cgt ctc ctt gta gca tgt tgt ttg gct gat atc ttt cgt atc      376
Asp Val Arg Leu Leu Val Ala Cys Cys Leu Ala Asp Ile Phe Arg Ile
45                  50                  55                  60

tat gcc cca gaa gct cca tat act tcc cat gat aaa ctt aag gac ata      424
Tyr Ala Pro Glu Ala Pro Tyr Thr Ser His Asp Lys Leu Lys Asp Ile
                65                  70                  75

ttt ttg ttt att acc aga caa tta aaa ggt ttg gag gat aca aag agt      472
Phe Leu Phe Ile Thr Arg Gln Leu Lys Gly Leu Glu Asp Thr Lys Ser
            80                  85                  90

cca cag ttt aat aga tac ttt tat tta tta gag aat tta gct tgg gtt      520
Pro Gln Phe Asn Arg Tyr Phe Tyr Leu Leu Glu Asn Leu Ala Trp Val
        95                  100                 105

aaa tca tat aac atc tgc ttt gaa ttg gaa gat tgc aat gaa att ttt      568
Lys Ser Tyr Asn Ile Cys Phe Glu Leu Glu Asp Cys Asn Glu Ile Phe
    110                 115                 120

att cag ctt ttt aga act ctc ttc tca gtg atc aac aat agc cac aat      616
Ile Gln Leu Phe Arg Thr Leu Phe Ser Val Ile Asn Asn Ser His Asn
125                 130                 135                 140

aag aag gta caa atg cac atg cta gat ttg atg agt tct atc atc atg      664
Lys Lys Val Gln Met His Met Leu Asp Leu Met Ser Ser Ile Ile Met
                145                 150                 155

gaa ggt gat gga gtt act caa gaa tta ttg gac tcc att ctt att aac      712
Glu Gly Asp Gly Val Thr Gln Glu Leu Leu Asp Ser Ile Leu Ile Asn
            160                 165                 170

ctc att cct gca cat aag aac tta aat aaa cag tcc ttt gac ctt gca      760
Leu Ile Pro Ala His Lys Asn Leu Asn Lys Gln Ser Phe Asp Leu Ala
        175                 180                 185

aaa gtg cta ttg aaa aga aca gtc cag act att gag gca tgc att gct      808
Lys Val Leu Leu Lys Arg Thr Val Gln Thr Ile Glu Ala Cys Ile Ala
    190                 195                 200

aat ttt ttc aat caa gtc ctg gtg ctg gga aga tca tca gta agt gat      856
Asn Phe Phe Asn Gln Val Leu Val Leu Gly Arg Ser Ser Val Ser Asp
205                 210                 215                 220

ttg tca gaa cat gta ttt gat ctg att cag gaa ctt ttt gct ata gat      904
Leu Ser Glu His Val Phe Asp Leu Ile Gln Glu Leu Phe Ala Ile Asp
                225                 230                 235

cct cat tta tta tta tcc gtc atg cca cag ctt gaa ttc aaa cta aag      952
Pro His Leu Leu Leu Ser Val Met Pro Gln Leu Glu Phe Lys Leu Lys
            240                 245                 250

agc aat gat gga gaa gag cga tta gct gtt gtt cga ctt cta gct aaa     1000
Ser Asn Asp Gly Glu Glu Arg Leu Ala Val Val Arg Leu Leu Ala Lys
        255                 260                 265

ttg ttt ggc tcc aaa gat tct gat ttg gca aca cag aat cgt cct ctt     1048
Leu Phe Gly Ser Lys Asp Ser Asp Leu Ala Thr Gln Asn Arg Pro Leu
```

```
    270                 275                 280

tgg caa tgt ttt ctt gga cga ttt aat gat att cat gtt cct gtg aga     1096
Trp Gln Cys Phe Leu Gly Arg Phe Asn Asp Ile His Val Pro Val Arg
285                 290                 295                 300

tta gaa agt gtg aaa ttt gcc agt cat tgt tta atg aat cac cca gat     1144
Leu Glu Ser Val Lys Phe Ala Ser His Cys Leu Met Asn His Pro Asp
                305                 310                 315

tta gcg aag gat ctc aca gaa tat tta aag gtt aga tca cat gat cca     1192
Leu Ala Lys Asp Leu Thr Glu Tyr Leu Lys Val Arg Ser His Asp Pro
            320                 325                 330

gaa gaa gct att cgt cat gat gtc att gtt act ata ata aca gct gcc     1240
Glu Glu Ala Ile Arg His Asp Val Ile Val Thr Ile Ile Thr Ala Ala
        335                 340                 345

aag agg gac ctg gcc tta gta aat gat cag ctg ctt ggc ttt gta agg     1288
Lys Arg Asp Leu Ala Leu Val Asn Asp Gln Leu Leu Gly Phe Val Arg
    350                 355                 360

gaa aga aca ctg gat aaa cgg tgg cga gta aga aaa gaa gct atg atg     1336
Glu Arg Thr Leu Asp Lys Arg Trp Arg Val Arg Lys Glu Ala Met Met
365                 370                 375                 380

ggt ctg gct cag ctt tat aag aaa tac tgt ctt cat ggt gaa gca gga     1384
Gly Leu Ala Gln Leu Tyr Lys Lys Tyr Cys Leu His Gly Glu Ala Gly
                385                 390                 395

aag gaa gct gca gag aaa gtc agc tgg ata aag gac aaa ctt ctg cat     1432
Lys Glu Ala Ala Glu Lys Val Ser Trp Ile Lys Asp Lys Leu Leu His
            400                 405                 410

att tat tat cag aac agc att gac gac aaa ctg ttg gta gag aaa atc     1480
Ile Tyr Tyr Gln Asn Ser Ile Asp Asp Lys Leu Leu Val Glu Lys Ile
        415                 420                 425

ttt gct cag tat ctt gtc ccc cac aac ctg gaa aca gaa gag aga atg     1528
Phe Ala Gln Tyr Leu Val Pro His Asn Leu Glu Thr Glu Glu Arg Met
    430                 435                 440

aaa tgc tta tat tac tta tat gct agt ttg gat cca aat gct gta aaa     1576
Lys Cys Leu Tyr Tyr Leu Tyr Ala Ser Leu Asp Pro Asn Ala Val Lys
445                 450                 455                 460

gct ctc aac gaa atg tgg aag tgt cag aac atg ctt cgg agc cat gta     1624
Ala Leu Asn Glu Met Trp Lys Cys Gln Asn Met Leu Arg Ser His Val
                465                 470                 475

cgc gaa cta ttg gat ttg cac aag cag cct aca tca gag gct aac tgt     1672
Arg Glu Leu Leu Asp Leu His Lys Gln Pro Thr Ser Glu Ala Asn Cys
            480                 485                 490

tct gcc atg ttt gga aaa ctg atg acc ata gca aag aat ttg cct gac     1720
Ser Ala Met Phe Gly Lys Leu Met Thr Ile Ala Lys Asn Leu Pro Asp
        495                 500                 505

ccc ggg aaa gca caa gat ttt gtg aag aaa ttt aac cag gtt ctc ggc     1768
Pro Gly Lys Ala Gln Asp Phe Val Lys Lys Phe Asn Gln Val Leu Gly
    510                 515                 520

gat gat gag aaa ctt cgg tct cag ttg gag tta tta att agc cca acc     1816
Asp Asp Glu Lys Leu Arg Ser Gln Leu Glu Leu Leu Ile Ser Pro Thr
525                 530                 535                 540

tgt tct tgc aaa caa gca gat att tgt gtg aga gaa ata gcc cgg aaa     1864
Cys Ser Cys Lys Gln Ala Asp Ile Cys Val Arg Glu Ile Ala Arg Lys
                545                 550                 555

ctt gca aat cct aag caa cca aca aat cct ttt cta gag atg gtc aaa     1912
Leu Ala Asn Pro Lys Gln Pro Thr Asn Pro Phe Leu Glu Met Val Lys
            560                 565                 570

ttt ctg ttg gaa aga atc gca cct gtg cac att gat tca gaa gcc ata     1960
Phe Leu Leu Glu Arg Ile Ala Pro Val His Ile Asp Ser Glu Ala Ile
        575                 580                 585

agt gca cta gtg aaa ttg atg aat aag tca ata gag ggg aca gca gat     2008
```

```
Ser Ala Leu Val Lys Leu Met Asn Lys Ser Ile Glu Gly Thr Ala Asp
    590                 595                 600

gat gaa gag gag ggt gta agt cca gat aca gct atc cgt tca gga ctt      2056
Asp Glu Glu Glu Gly Val Ser Pro Asp Thr Ala Ile Arg Ser Gly Leu
605                 610                 615                 620

gaa ctt ctt aag gtt ctg tct ttt aca cat cct acc tcg ttc cac tct      2104
Glu Leu Leu Lys Val Leu Ser Phe Thr His Pro Thr Ser Phe His Ser
                625                 630                 635

gca gag aca tat gag tcc ttg tta cag tgc cta aga atg gag gat gac      2152
Ala Glu Thr Tyr Glu Ser Leu Leu Gln Cys Leu Arg Met Glu Asp Asp
            640                 645                 650

aag gta gca gaa gct gct att caa att ttt aga aat aca ggt cac aaa      2200
Lys Val Ala Glu Ala Ala Ile Gln Ile Phe Arg Asn Thr Gly His Lys
        655                 660                 665

ata gaa aca gac ctt ccc cag ata cga tcg acc tta att ccc att tta      2248
Ile Glu Thr Asp Leu Pro Gln Ile Arg Ser Thr Leu Ile Pro Ile Leu
    670                 675                 680

cat caa aaa gca aag agg ggt act cca cac caa gca aaa cag gct gtg      2296
His Gln Lys Ala Lys Arg Gly Thr Pro His Gln Ala Lys Gln Ala Val
685                 690                 695                 700

cac tgt ata cac gcc ata ttc aca aat aaa gaa gtc cag ctt gca cag      2344
His Cys Ile His Ala Ile Phe Thr Asn Lys Glu Val Gln Leu Ala Gln
                705                 710                 715

att ttt gag cca ctc agt agg agt ctg aat gct gat gtg cca gaa caa      2392
Ile Phe Glu Pro Leu Ser Arg Ser Leu Asn Ala Asp Val Pro Glu Gln
            720                 725                 730

ctt ata act cca tta gtt tca ttg ggc cac att tct atg tta gca cca      2440
Leu Ile Thr Pro Leu Val Ser Leu Gly His Ile Ser Met Leu Ala Pro
        735                 740                 745

gat cag ttt gct tcc cca atg aaa tct gta gta gca aat ttt att gtg      2488
Asp Gln Phe Ala Ser Pro Met Lys Ser Val Val Ala Asn Phe Ile Val
    750                 755                 760

aaa gat ctg cta atg aat gac agg tca aca ggt gaa aag aat gga aaa      2536
Lys Asp Leu Leu Met Asn Asp Arg Ser Thr Gly Glu Lys Asn Gly Lys
765                 770                 775                 780

ctg tgg tct cca gat gaa gag gtt tcc cct gaa gta cta gca aag gta      2584
Leu Trp Ser Pro Asp Glu Glu Val Ser Pro Glu Val Leu Ala Lys Val
                785                 790                 795

cag gca att aaa ctt ctg gta agg tgg ctg ttg ggt atg aaa aac aac      2632
Gln Ala Ile Lys Leu Leu Val Arg Trp Leu Leu Gly Met Lys Asn Asn
            800                 805                 810

cag tct aaa tct gcc aat tca acc ctt cgg tta tta tca gcg atg ttg      2680
Gln Ser Lys Ser Ala Asn Ser Thr Leu Arg Leu Leu Ser Ala Met Leu
        815                 820                 825

gtt agt gag ggt gac ctg aca gag caa aag agg atc agt aaa tct gat      2728
Val Ser Glu Gly Asp Leu Thr Glu Gln Lys Arg Ile Ser Lys Ser Asp
    830                 835                 840

atg tct cgc ttg cga tta gct gct ggt agt gcc ata atg aag ctt gct      2776
Met Ser Arg Leu Arg Leu Ala Ala Gly Ser Ala Ile Met Lys Leu Ala
845                 850                 855                 860

cag gaa cct tgt tac cat gaa att att acc cca gaa cag ttt cag ctc      2824
Gln Glu Pro Cys Tyr His Glu Ile Ile Thr Pro Glu Gln Phe Gln Leu
                865                 870                 875

tgt gca ctt gtt att aat gat gag tgt tac caa gta agg cag ata ttt      2872
Cys Ala Leu Val Ile Asn Asp Glu Cys Tyr Gln Val Arg Gln Ile Phe
            880                 885                 890

gct cag aag ctg cat aag gca ctt gtg aag tta ctg ctc cca ttg gag      2920
Ala Gln Lys Leu His Lys Ala Leu Val Lys Leu Leu Leu Pro Leu Glu
        895                 900                 905
```

```
tat atg gcg atc ttt gcc ttg tgt gcc aaa gat cct gtg aag gag aga     2968
Tyr Met Ala Ile Phe Ala Leu Cys Ala Lys Asp Pro Val Lys Glu Arg
    910                 915                 920

aga gca cac gca cga caa tgt tta ctg aaa aat atc agt ata cgc agg     3016
Arg Ala His Ala Arg Gln Cys Leu Leu Lys Asn Ile Ser Ile Arg Arg
925                 930                 935                 940

gaa tac att aag cag aat cct atg gct act gag aaa tta tta tca ctg     3064
Glu Tyr Ile Lys Gln Asn Pro Met Ala Thr Glu Lys Leu Leu Ser Leu
                945                 950                 955

ttg cct gaa tat gta gtt cca tac atg att cac ctg cta gcc cat gat     3112
Leu Pro Glu Tyr Val Val Pro Tyr Met Ile His Leu Leu Ala His Asp
            960                 965                 970

cca gat ttt aca aga tca caa gat gtt gat cag ctt cgt gat atc aaa     3160
Pro Asp Phe Thr Arg Ser Gln Asp Val Asp Gln Leu Arg Asp Ile Lys
        975                 980                 985

gag tgc cta tgg ttc atg ctt gaa gtt tta atg aca  aag aat gaa aac    3208
Glu Cys Leu Trp Phe Met Leu Glu Val Leu Met Thr  Lys Asn Glu Asn
    990                 995                 1000

aat  agc cat gcc ttt atg  aag aag atg gca gag  aac atc aag tta      3253
Asn  Ser His Ala Phe Met  Lys Lys Met Ala Glu  Asn Ile Lys Leu
1005                 1010                 1015

acc  aga gat gcc cag tct  cca gat gaa tcc aag  aca aat gaa aaa      3298
Thr  Arg Asp Ala Gln Ser  Pro Asp Glu Ser Lys  Thr Asn Glu Lys
1020                 1025                 1030

ctg  tat aca gta tgt gat  gtg gct ctc tgt gtt  ata aat agt aaa      3343
Leu  Tyr Thr Val Cys Asp  Val Ala Leu Cys Val  Ile Asn Ser Lys
1035                 1040                 1045

agt  gct ttg tgc aat gca  gat tca cca aag gac  cca gtc ctc cca      3388
Ser  Ala Leu Cys Asn Ala  Asp Ser Pro Lys Asp  Pro Val Leu Pro
1050                 1055                 1060

atg  aaa ttt ttt aca caa  cct gaa aag gac ttc  tgt aac gat aag      3433
Met  Lys Phe Phe Thr Gln  Pro Glu Lys Asp Phe  Cys Asn Asp Lys
1065                 1070                 1075

agt  tat att tca gaa gag  aca aga gta ctt ctg  tta aca gga aag      3478
Ser  Tyr Ile Ser Glu Glu  Thr Arg Val Leu Leu  Leu Thr Gly Lys
1080                 1085                 1090

cca  aag cct gct gga gta  cta ggt gca gta aat  aag cct tta tca      3523
Pro  Lys Pro Ala Gly Val  Leu Gly Ala Val Asn  Lys Pro Leu Ser
1095                 1100                 1105

gca  acg gga agg aaa ccc  tat gtt aga agc act  ggc act gag act      3568
Ala  Thr Gly Arg Lys Pro  Tyr Val Arg Ser Thr  Gly Thr Glu Thr
1110                 1115                 1120

gga  agc aat att aat gta  aat tca gag ctg aac  cct tca acc gga      3613
Gly  Ser Asn Ile Asn Val  Asn Ser Glu Leu Asn  Pro Ser Thr Gly
1125                 1130                 1135

aat  cga tca agg gaa cag  agt tca gag gca gca  gaa act gga gtt      3658
Asn  Arg Ser Arg Glu Gln  Ser Ser Glu Ala Ala  Glu Thr Gly Val
1140                 1145                 1150

agt  gaa aat gaa gag aac  cct gtg agg att att  tca gtc aca cct      3703
Ser  Glu Asn Glu Glu Asn  Pro Val Arg Ile Ile  Ser Val Thr Pro
1155                 1160                 1165

gta  aag aat att gac cca  gta aag aat aag gaa  att aat tct gat      3748
Val  Lys Asn Ile Asp Pro  Val Lys Asn Lys Glu  Ile Asn Ser Asp
1170                 1175                 1180

cag  gct acc cag ggc aac  atc agc agt gac cga  gga aag aaa aga      3793
Gln  Ala Thr Gln Gly Asn  Ile Ser Ser Asp Arg  Gly Lys Lys Arg
1185                 1190                 1195

aca  gta aca gca gct ggt  gca gag aat atc caa  caa aaa aca gat      3838
Thr  Val Thr Ala Ala Gly  Ala Glu Asn Ile Gln  Gln Lys Thr Asp
1200                 1205                 1210
```

```
gag  aaa gta gat gaa tcg  gga cct ccc gcc cct  tcc aaa ccc agg      3883
Glu  Lys Val Asp Glu Ser  Gly Pro Pro Ala Pro  Ser Lys Pro Arg
1215                 1220                 1225

aga  gga cgt cga ccc aag  tct gaa tct cag ggc  aat gct acc aaa      3928
Arg  Gly Arg Arg Pro Lys  Ser Glu Ser Gln Gly  Asn Ala Thr Lys
1230                 1235                 1240

aat  gat gat cta aat aaa  cct att aac aag gga  agg aag aga gct      3973
Asn  Asp Asp Leu Asn Lys  Pro Ile Asn Lys Gly  Arg Lys Arg Ala
1245                 1250                 1255

gca  gtg ggt cag gag agc  cct ggg ggt ttg gaa  gca ggt aat gcc      4018
Ala  Val Gly Gln Glu Ser  Pro Gly Gly Leu Glu  Ala Gly Asn Ala
1260                 1265                 1270

aaa  gca ccc aaa ctg caa  gat tta gcc aaa aag  gca gca cca gca      4063
Lys  Ala Pro Lys Leu Gln  Asp Leu Ala Lys Lys  Ala Ala Pro Ala
1275                 1280                 1285

gaa  aga caa att gac tta  caa agg taa aaatgcattt gcaaagggag         4110
Glu  Arg Gln Ile Asp Leu  Gln Arg
1290                 1295

aaaatgaagg ccaaacagaa gcaggctcca gcttctgcaa aaacttggat tcacaaatgt   4170

ccctgaacag aaaatgaagc tcacttcaga acacacactc tctgccttga aaactaaaga   4230

gactattact tccttttcac atgaccacaa gtcctctgat ggaaatgtac agcagaaact   4290

cttgagagag aggctaaaag caactctgtt ctccccccttc ccctagactt ttcttacgaa   4350

aagtcaataa ttaagcaaat tgcttaacac ttggttccag ttcctgccta tctggagttt   4410

aaatgcgtaa tacaccatta atttccacgc tgcagttttt attttaaaga aagtaacaag   4470

atgtctttac actgacactg aaaattcatc cattttagag ccaggaattc ccatgttaca   4530

caggaaaaaa tagaagtcta ctgaattaat tttttaaaag aaaagagatc agattaaata   4590

tttctttgtt tttccttttg gaaactttta tgtataattc tttctgcctg cctacttttc   4650

tgcaaaaatg agatgtacag atttcggttc cctgctatga aaagtgatgt ggtagcaatt   4710

ttataaatgt tgctttctga tttttatcag agtgagaaaa ttaaaattat tgatttgcaa   4770

gtagtaaaca gttcatattt tgatttcccc tcattttagt ttaatataat ttgcaataaa   4830

tgtacatatt gttgtttgtt tcataaagca tatcacttta aaatggtttt tactcctgtg   4890

attatgttgg aatatttgga attttaaagg agtaaagact gtccagcatt tggttttata   4950

atgtttgtca ccagattttt attaatgtaa aaaaaatcaa tttttaaaaa atagttggac   5010

tttggcagct tttaaggaaa gttggaggtg ttttaggatt gctatcaatt ttcagcattg   5070

tgctatttgg aaataagtgt tttgcttttg tctgatggtc tgggctcatt tttatgttta   5130

ttttagaaaa ctgttgcatc aatatattat gtttcttggc attgttcagc ataggtaatg   5190

tgtgcacttt atgtgtacac ataatcatat ttaagttttt tgcataaaat aaatgcttct   5250

agatgtcatg gcagtctttt taatcttttt atcatatgct ttcttgtgaa ttttttcatg   5310

ttaaagagct aaagtcataa catgattaca gtcaactctc cattatctat ataaaatagt   5370

gactaagcct caggttttta attttgtgat aacaaaataa cgaaggcatg taagacctga   5430

ttctggagga acatgaaatt tgtcttttct catgtccaga gttctatcct gcccccactg   5490

tccactgtag ggtcatccgc aaagccctag cagaatgtgc tcactccatt tccttacacg   5550

tttctagcat gggtcagagg aaacaacatt tgtgttataa cttcgtcttg ataggctgta   5610

gtgtacatgg gatgtaaaac aaacaagtgt atcaaaggtg gatgattctg ttagagtgaa   5670

gtttgagagt aaatgtcact tacgtttctc atagataatc aagagttggc tgtgtattga   5730
```

```
ctgaaagatg ggtaattatt ttaaatatgc atttacacac atttaggtat cagaagatgc   5790

ttagggaaca atggatacca atgatagaaa atgatacctt tacaggggca gaaaaatccc   5850

cactcttcct tattgcctct tcagaaccct ttagaaagta taaaatattg cctccaacat   5910

gctgaaaaag agtatctatg cataagtatc agagaagtcc ctcaagcaat cagtaggtgt   5970

gttctattta gagagagttt aaagttctct tagcatcaga caacttgatt cctaaggttt   6030

ccagtgtgtc accaacaaaa agtgcattga tagggacctt tgtctcttcc tccctttgat   6090

taattgcccg gcatcacagt ttactagatt accaagtgtt acatcatatt aaataaaatg   6150

tagcagaacc atctgcatca atatattcct gtttagattt ttgcaggaga gaagttaaaa   6210

ggatttgctc cttgtatgat gtaagtggcc caccccaatt ttgtaacatg atgcaagtgt   6270

ctggcactaa gggaagcaag agtagggttg tggaaagacc aagctgatgg ggagggactt   6330

gtttacggga attttttttag ttttcctttt caaaggaaaa cattaaaatc ccttaggaat   6390

ttggtattca catctcagag aactacaaca caaaagtgca gacttatatt tgagaattaa   6450

tgttaaccct ttgtgtctag tttgaagctt cttgtatttg tctaaaacaa caagccagaa   6510

ttttgtatct cctttgataa aaagtgtgta taatgtaaag tagttttgca tattcttgtg   6570

ctgcacatgg gctgaatttt taaatttttt ttaaaaactt gaagcagaac cttgtaattt   6630

gtgtaaatga caagtgtaaa atcctaccat aaaatgctaa aaatatgcac tgtttcaaat   6690

aaaaccaaga aatgcagcat taaaaaaaaa aaaaaa                              6726
```

<210> SEQ ID NO 4
<211> LENGTH: 1297
<212> TYPE: PRT
<213> ORGANISM: Homo sapiens

<400> SEQUENCE: 4

```
Met Ile Lys Arg Leu Lys Met Val Val Lys Thr Phe Met Asp Met Asp
1               5                   10                  15

Gln Asp Ser Glu Asp Glu Lys Gln Gln Tyr Leu Pro Leu Ala Leu His
            20                  25                  30

Leu Ala Ser Glu Phe Phe Leu Arg Asn Pro Asn Lys Asp Val Arg Leu
        35                  40                  45

Leu Val Ala Cys Cys Leu Ala Asp Ile Phe Arg Ile Tyr Ala Pro Glu
    50                  55                  60

Ala Pro Tyr Thr Ser His Asp Lys Leu Lys Asp Ile Phe Leu Phe Ile
65                  70                  75                  80

Thr Arg Gln Leu Lys Gly Leu Glu Asp Thr Lys Ser Pro Gln Phe Asn
                85                  90                  95

Arg Tyr Phe Tyr Leu Leu Glu Asn Leu Ala Trp Val Lys Ser Tyr Asn
            100                 105                 110

Ile Cys Phe Glu Leu Glu Asp Cys Asn Glu Ile Phe Ile Gln Leu Phe
        115                 120                 125

Arg Thr Leu Phe Ser Val Ile Asn Asn Ser His Asn Lys Lys Val Gln
    130                 135                 140

Met His Met Leu Asp Leu Met Ser Ser Ile Ile Met Glu Gly Asp Gly
145                 150                 155                 160

Val Thr Gln Glu Leu Leu Asp Ser Ile Leu Ile Asn Leu Ile Pro Ala
                165                 170                 175

His Lys Asn Leu Asn Lys Gln Ser Phe Asp Leu Ala Lys Val Leu Leu
            180                 185                 190

Lys Arg Thr Val Gln Thr Ile Glu Ala Cys Ile Ala Asn Phe Phe Asn
```

```
        195                 200                 205

Gln Val Leu Val Leu Gly Arg Ser Ser Val Ser Asp Leu Ser Glu His
    210                 215                 220

Val Phe Asp Leu Ile Gln Glu Leu Phe Ala Ile Asp Pro His Leu Leu
225                 230                 235                 240

Leu Ser Val Met Pro Gln Leu Glu Phe Lys Leu Lys Ser Asn Asp Gly
                245                 250                 255

Glu Glu Arg Leu Ala Val Val Arg Leu Leu Ala Lys Leu Phe Gly Ser
            260                 265                 270

Lys Asp Ser Asp Leu Ala Thr Gln Asn Arg Pro Leu Trp Gln Cys Phe
        275                 280                 285

Leu Gly Arg Phe Asn Asp Ile His Val Pro Val Arg Leu Glu Ser Val
    290                 295                 300

Lys Phe Ala Ser His Cys Leu Met Asn His Pro Asp Leu Ala Lys Asp
305                 310                 315                 320

Leu Thr Glu Tyr Leu Lys Val Arg Ser His Asp Pro Glu Glu Ala Ile
                325                 330                 335

Arg His Asp Val Ile Val Thr Ile Ile Thr Ala Ala Lys Arg Asp Leu
            340                 345                 350

Ala Leu Val Asn Asp Gln Leu Leu Gly Phe Val Arg Glu Arg Thr Leu
        355                 360                 365

Asp Lys Arg Trp Arg Val Arg Lys Glu Ala Met Met Gly Leu Ala Gln
    370                 375                 380

Leu Tyr Lys Lys Tyr Cys Leu His Gly Glu Ala Gly Lys Glu Ala Ala
385                 390                 395                 400

Glu Lys Val Ser Trp Ile Lys Asp Lys Leu Leu His Ile Tyr Tyr Gln
                405                 410                 415

Asn Ser Ile Asp Asp Lys Leu Leu Val Glu Lys Ile Phe Ala Gln Tyr
            420                 425                 430

Leu Val Pro His Asn Leu Glu Thr Glu Glu Arg Met Lys Cys Leu Tyr
        435                 440                 445

Tyr Leu Tyr Ala Ser Leu Asp Pro Asn Ala Val Lys Ala Leu Asn Glu
    450                 455                 460

Met Trp Lys Cys Gln Asn Met Leu Arg Ser His Val Arg Glu Leu Leu
465                 470                 475                 480

Asp Leu His Lys Gln Pro Thr Ser Glu Ala Asn Cys Ser Ala Met Phe
                485                 490                 495

Gly Lys Leu Met Thr Ile Ala Lys Asn Leu Pro Asp Pro Gly Lys Ala
            500                 505                 510

Gln Asp Phe Val Lys Lys Phe Asn Gln Val Leu Gly Asp Asp Glu Lys
        515                 520                 525

Leu Arg Ser Gln Leu Glu Leu Leu Ile Ser Pro Thr Cys Ser Cys Lys
    530                 535                 540

Gln Ala Asp Ile Cys Val Arg Glu Ile Ala Arg Lys Leu Ala Asn Pro
545                 550                 555                 560

Lys Gln Pro Thr Asn Pro Phe Leu Glu Met Val Lys Phe Leu Leu Glu
                565                 570                 575

Arg Ile Ala Pro Val His Ile Asp Ser Glu Ala Ile Ser Ala Leu Val
            580                 585                 590

Lys Leu Met Asn Lys Ser Ile Glu Gly Thr Ala Asp Asp Glu Glu Glu
        595                 600                 605

Gly Val Ser Pro Asp Thr Ala Ile Arg Ser Gly Leu Glu Leu Leu Lys
    610                 615                 620
```

```
Val Leu Ser Phe Thr His Pro Thr Ser Phe His Ser Ala Glu Thr Tyr
625                 630                 635                 640

Glu Ser Leu Leu Gln Cys Leu Arg Met Glu Asp Asp Lys Val Ala Glu
                645                 650                 655

Ala Ala Ile Gln Ile Phe Arg Asn Thr Gly His Lys Ile Glu Thr Asp
            660                 665                 670

Leu Pro Gln Ile Arg Ser Thr Leu Ile Pro Ile Leu His Gln Lys Ala
        675                 680                 685

Lys Arg Gly Thr Pro His Gln Ala Lys Gln Ala Val His Cys Ile His
    690                 695                 700

Ala Ile Phe Thr Asn Lys Glu Val Gln Leu Ala Gln Ile Phe Glu Pro
705                 710                 715                 720

Leu Ser Arg Ser Leu Asn Ala Asp Val Pro Glu Gln Leu Ile Thr Pro
                725                 730                 735

Leu Val Ser Leu Gly His Ile Ser Met Leu Ala Pro Asp Gln Phe Ala
            740                 745                 750

Ser Pro Met Lys Ser Val Val Ala Asn Phe Ile Val Lys Asp Leu Leu
        755                 760                 765

Met Asn Asp Arg Ser Thr Gly Glu Lys Asn Gly Lys Leu Trp Ser Pro
    770                 775                 780

Asp Glu Glu Val Ser Pro Glu Val Leu Ala Lys Val Gln Ala Ile Lys
785                 790                 795                 800

Leu Leu Val Arg Trp Leu Leu Gly Met Lys Asn Asn Gln Ser Lys Ser
                805                 810                 815

Ala Asn Ser Thr Leu Arg Leu Leu Ser Ala Met Leu Val Ser Glu Gly
            820                 825                 830

Asp Leu Thr Glu Gln Lys Arg Ile Ser Lys Ser Asp Met Ser Arg Leu
        835                 840                 845

Arg Leu Ala Ala Gly Ser Ala Ile Met Lys Leu Ala Gln Glu Pro Cys
    850                 855                 860

Tyr His Glu Ile Ile Thr Pro Glu Gln Phe Gln Leu Cys Ala Leu Val
865                 870                 875                 880

Ile Asn Asp Glu Cys Tyr Gln Val Arg Gln Ile Phe Ala Gln Lys Leu
                885                 890                 895

His Lys Ala Leu Val Lys Leu Leu Leu Pro Leu Glu Tyr Met Ala Ile
            900                 905                 910

Phe Ala Leu Cys Ala Lys Asp Pro Val Lys Glu Arg Arg Ala His Ala
        915                 920                 925

Arg Gln Cys Leu Leu Lys Asn Ile Ser Ile Arg Arg Glu Tyr Ile Lys
    930                 935                 940

Gln Asn Pro Met Ala Thr Glu Lys Leu Leu Ser Leu Leu Pro Glu Tyr
945                 950                 955                 960

Val Val Pro Tyr Met Ile His Leu Leu Ala His Asp Pro Asp Phe Thr
                965                 970                 975

Arg Ser Gln Asp Val Asp Gln Leu Arg Asp Ile Lys Glu Cys Leu Trp
            980                 985                 990

Phe Met Leu Glu Val Leu Met Thr  Lys Asn Glu Asn Asn  Ser His Ala
        995                 1000                1005

Phe Met  Lys Lys Met Ala Glu  Asn Ile Lys Leu Thr  Arg Asp Ala
    1010                1015                1020

Gln Ser  Pro Asp Glu Ser Lys  Thr Asn Glu Lys Leu  Tyr Thr Val
    1025                1030                1035
```

```
Cys Asp  Val Ala Leu Cys Val  Ile Asn Ser Lys Ser  Ala Leu Cys
    1040                 1045                 1050

Asn Ala  Asp Ser Pro Lys Asp  Pro Val Leu Pro Met  Lys Phe Phe
    1055                 1060                 1065

Thr Gln  Pro Glu Lys Asp Phe  Cys Asn Asp Lys Ser  Tyr Ile Ser
    1070                 1075                 1080

Glu Glu  Thr Arg Val Leu Leu  Leu Thr Gly Lys Pro  Lys Pro Ala
    1085                 1090                 1095

Gly Val  Leu Gly Ala Val Asn  Lys Pro Leu Ser Ala  Thr Gly Arg
    1100                 1105                 1110

Lys Pro  Tyr Val Arg Ser Thr  Gly Thr Glu Thr Gly  Ser Asn Ile
    1115                 1120                 1125

Asn Val  Asn Ser Glu Leu Asn  Pro Ser Thr Gly Asn  Arg Ser Arg
    1130                 1135                 1140

Glu Gln  Ser Ser Glu Ala Ala  Glu Thr Gly Val Ser  Glu Asn Glu
    1145                 1150                 1155

Glu Asn  Pro Val Arg Ile Ile  Ser Val Thr Pro Val  Lys Asn Ile
    1160                 1165                 1170

Asp Pro  Val Lys Asn Lys Glu  Ile Asn Ser Asp Gln  Ala Thr Gln
    1175                 1180                 1185

Gly Asn  Ile Ser Ser Asp Arg  Gly Lys Lys Arg Thr  Val Thr Ala
    1190                 1195                 1200

Ala Gly  Ala Glu Asn Ile Gln  Gln Lys Thr Asp Glu  Lys Val Asp
    1205                 1210                 1215

Glu Ser  Gly Pro Pro Ala Pro  Ser Lys Pro Arg Arg  Gly Arg Arg
    1220                 1225                 1230

Pro Lys  Ser Glu Ser Gln Gly  Asn Ala Thr Lys Asn  Asp Asp Leu
    1235                 1240                 1245

Asn Lys  Pro Ile Asn Lys Gly  Arg Lys Arg Ala Ala  Val Gly Gln
    1250                 1255                 1260

Glu Ser  Pro Gly Gly Leu Glu  Ala Gly Asn Ala Lys  Ala Pro Lys
    1265                 1270                 1275

Leu Gln  Asp Leu Ala Lys Lys  Ala Ala Pro Ala Glu  Arg Gln Ile
    1280                 1285                 1290

Asp Leu  Gln Arg
    1295


<210> SEQ ID NO 5
<211> LENGTH: 4452
<212> TYPE: DNA
<213> ORGANISM: Mus musculus
<220> FEATURE:
<221> NAME/KEY: CDS
<222> LOCATION: (148)..(4146)
<223> OTHER INFORMATION:

<400> SEQUENCE: 5

acggacggag ccgctttgtg tgcagcccga cgaggggcgg cggcggcggc gcaaccacct     60

gacagaggcc cggcgctcgc tgcaccgtcc gcccgcatga ggaggagagg ccggtagagg    120

actgtgagag aaaagttatt ccccagg atg gac ttc acg cag ccg aag cct gcc    174
                              Met Asp Phe Thr Gln Pro Lys Pro Ala
                              1               5

act gcc ctc tgt ggc gtc gtg agt gcg gac ggg aag atc gct tac cct      222
Thr Ala Leu Cys Gly Val Val Ser Ala Asp Gly Lys Ile Ala Tyr Pro
10                  15                  20                  25

ccg gga gta aaa gag atc acc gac aag atc acc acc gat gaa atg atc      270
```

```
Pro Gly Val Lys Glu Ile Thr Asp Lys Ile Thr Thr Asp Glu Met Ile
                30                  35                  40

aaa cgt ctg aag atg gta gtg aaa act ttt atg gat atg gat cag gat      318
Lys Arg Leu Lys Met Val Val Lys Thr Phe Met Asp Met Asp Gln Asp
            45                  50                  55

tca gaa gat gaa aag caa cag tat ctc cca cta gcc ttg cat ctc gca      366
Ser Glu Asp Glu Lys Gln Gln Tyr Leu Pro Leu Ala Leu His Leu Ala
        60                  65                  70

tct gaa ttc ttt ctc agg aac cct aat aaa gat gtg cgc ctt ctc gta      414
Ser Glu Phe Phe Leu Arg Asn Pro Asn Lys Asp Val Arg Leu Leu Val
    75                  80                  85

gca tgt tgt ttg gct gat ata ttt cga atc tat gcc cca gaa gct cca      462
Ala Cys Cys Leu Ala Asp Ile Phe Arg Ile Tyr Ala Pro Glu Ala Pro
90                  95                  100                 105

tat act tcc cat gat aaa ctt aag gac ata ttt ctc ttt att acc aga      510
Tyr Thr Ser His Asp Lys Leu Lys Asp Ile Phe Leu Phe Ile Thr Arg
                110                 115                 120

cag tta aaa ggt ttg gag gat aca aag agt cca cag ttt aat aga tat      558
Gln Leu Lys Gly Leu Glu Asp Thr Lys Ser Pro Gln Phe Asn Arg Tyr
            125                 130                 135

ttt tat tta tta gag aat tta gct tgg gtt aaa tca tat aac atc tgc      606
Phe Tyr Leu Leu Glu Asn Leu Ala Trp Val Lys Ser Tyr Asn Ile Cys
        140                 145                 150

ttt gag ttg gaa gat tgc aat gaa att ttt att cag ctt ttt aga act      654
Phe Glu Leu Glu Asp Cys Asn Glu Ile Phe Ile Gln Leu Phe Arg Thr
    155                 160                 165

ctc ttc tcg gta atc aac aat agc cac aat acg aaa gta caa atg cac      702
Leu Phe Ser Val Ile Asn Asn Ser His Asn Thr Lys Val Gln Met His
170                 175                 180                 185

atg tta gac ttg atg agt tct atc atc atg gaa ggt gat gga gtt act      750
Met Leu Asp Leu Met Ser Ser Ile Ile Met Glu Gly Asp Gly Val Thr
                190                 195                 200

caa gaa tta ttg gat tcc att ctt atc aac ctc atc cct gca cac aag      798
Gln Glu Leu Leu Asp Ser Ile Leu Ile Asn Leu Ile Pro Ala His Lys
            205                 210                 215

aac tta aat aaa cag tcc ttc gac ctt gca aaa gtc cta ctg aaa agg      846
Asn Leu Asn Lys Gln Ser Phe Asp Leu Ala Lys Val Leu Leu Lys Arg
        220                 225                 230

aca gtc cag act att gaa gca tgt att gcc aat ttt ttc aat caa gtc      894
Thr Val Gln Thr Ile Glu Ala Cys Ile Ala Asn Phe Phe Asn Gln Val
    235                 240                 245

ctg gtg ctg ggc aga tca tca gtc agc gac ctg tct gaa cac gta ttt      942
Leu Val Leu Gly Arg Ser Ser Val Ser Asp Leu Ser Glu His Val Phe
250                 255                 260                 265

gat ctg att cag gaa ctt ttt gct atc gat cct cag tta ctg tta tct      990
Asp Leu Ile Gln Glu Leu Phe Ala Ile Asp Pro Gln Leu Leu Leu Ser
                270                 275                 280

gtc atg cca cag ctt gaa ttc aaa ctg aag agc aac gat ggt gaa gaa     1038
Val Met Pro Gln Leu Glu Phe Lys Leu Lys Ser Asn Asp Gly Glu Glu
            285                 290                 295

cgc cta gct gtg gtt cga ctc ctc gca aaa ttg ttc ggc tct aaa gat     1086
Arg Leu Ala Val Val Arg Leu Leu Ala Lys Leu Phe Gly Ser Lys Asp
        300                 305                 310

tca gat tta gca aca cag aat cgg cct ctc tgg cag tgc ttt ctt ggg     1134
Ser Asp Leu Ala Thr Gln Asn Arg Pro Leu Trp Gln Cys Phe Leu Gly
    315                 320                 325

cga ttt aat gac att cat gtt cct gtg agg tta gaa agt gtg aag ttt     1182
Arg Phe Asn Asp Ile His Val Pro Val Arg Leu Glu Ser Val Lys Phe
330                 335                 340                 345
```

```
gcc agc cac tgt ttg atg aat cac cca gac tta gcg aag gat ctg aca      1230
Ala Ser His Cys Leu Met Asn His Pro Asp Leu Ala Lys Asp Leu Thr
                350                 355                 360

gaa tat ttg aaa gtt agg tca cat gat cca gaa gaa gcc att cgt cat      1278
Glu Tyr Leu Lys Val Arg Ser His Asp Pro Glu Glu Ala Ile Arg His
            365                 370                 375

gat gtt att gtt act ata ata aca gct gcc aaa aga gac ctt gcc tta      1326
Asp Val Ile Val Thr Ile Ile Thr Ala Ala Lys Arg Asp Leu Ala Leu
        380                 385                 390

gta aat gat cag ttg ctt ggc ttt gtc agg gaa agg aca ctg gat aaa      1374
Val Asn Asp Gln Leu Leu Gly Phe Val Arg Glu Arg Thr Leu Asp Lys
    395                 400                 405

cgg tgg cga gta aga aaa gaa gcc atg atg ggt ctg gct cag ctc tat      1422
Arg Trp Arg Val Arg Lys Glu Ala Met Met Gly Leu Ala Gln Leu Tyr
410                 415                 420                 425

aag aaa tac tgt ctt cat ggg gaa gca gga aag gaa gcc gcg gag aaa      1470
Lys Lys Tyr Cys Leu His Gly Glu Ala Gly Lys Glu Ala Ala Glu Lys
                430                 435                 440

gtc agc tgg ata aag gac aag ctg ctg cat atc tac tat cag aac agc      1518
Val Ser Trp Ile Lys Asp Lys Leu Leu His Ile Tyr Tyr Gln Asn Ser
            445                 450                 455

att gat gac aaa cta ttg gta gag aaa atc ttt gct cag tat ctt gtt      1566
Ile Asp Asp Lys Leu Leu Val Glu Lys Ile Phe Ala Gln Tyr Leu Val
        460                 465                 470

ccc cac aac ctg gaa aca gaa gag aga atg aaa tgc tta tat tat tta      1614
Pro His Asn Leu Glu Thr Glu Glu Arg Met Lys Cys Leu Tyr Tyr Leu
    475                 480                 485

tat gct agc ttg gat cca aat gct gta aaa gct ctc aat gaa atg tgg      1662
Tyr Ala Ser Leu Asp Pro Asn Ala Val Lys Ala Leu Asn Glu Met Trp
490                 495                 500                 505

aaa tgt cag aac atg ctt cga agt cat gtg cgt gaa cta ttg gac tta      1710
Lys Cys Gln Asn Met Leu Arg Ser His Val Arg Glu Leu Leu Asp Leu
                510                 515                 520

cac aag cag cct aca tca gaa gcg aac tgt tct gcc atg ttt ggg aaa      1758
His Lys Gln Pro Thr Ser Glu Ala Asn Cys Ser Ala Met Phe Gly Lys
            525                 530                 535

ctg atg acc ata gca aag aat ttg cct gac cct gga aaa gca caa gat      1806
Leu Met Thr Ile Ala Lys Asn Leu Pro Asp Pro Gly Lys Ala Gln Asp
        540                 545                 550

ttt gta aag aaa ttt aac cag gtt ctt ggt gat gat gag aaa ctg agg      1854
Phe Val Lys Lys Phe Asn Gln Val Leu Gly Asp Asp Glu Lys Leu Arg
    555                 560                 565

tct cag ttg gaa tta tta atc agc cca acc tgt tca tgc aag cag gct      1902
Ser Gln Leu Glu Leu Leu Ile Ser Pro Thr Cys Ser Cys Lys Gln Ala
570                 575                 580                 585

gac gtt tgt gtg agg gaa ata gct cgg aaa ctt gca aat cct aag cag      1950
Asp Val Cys Val Arg Glu Ile Ala Arg Lys Leu Ala Asn Pro Lys Gln
                590                 595                 600

cca acc aac cct ttt cta gag atg gtc aaa ttt ctt ttg gaa aga att      1998
Pro Thr Asn Pro Phe Leu Glu Met Val Lys Phe Leu Leu Glu Arg Ile
            605                 610                 615

gct cct gtg cac atc gat tca gaa gcc ata agt gca ctg gta aaa ctg      2046
Ala Pro Val His Ile Asp Ser Glu Ala Ile Ser Ala Leu Val Lys Leu
        620                 625                 630

atg aat aag tca atc gaa ggg acg gcc gat gat gaa gag gag ggt gtc      2094
Met Asn Lys Ser Ile Glu Gly Thr Ala Asp Asp Glu Glu Glu Gly Val
    635                 640                 645

agt cca gac tca gcc atc cgc tca gga ctt gag ctt ctt aag gtt ctg      2142
Ser Pro Asp Ser Ala Ile Arg Ser Gly Leu Glu Leu Leu Lys Val Leu
650                 655                 660                 665
```

```
tct ttc aca cat cct acc tcg ttc cac tct gca gag aca tat gag tcc      2190
Ser Phe Thr His Pro Thr Ser Phe His Ser Ala Glu Thr Tyr Glu Ser
                670                 675                 680

ttg tta cag tgc cta aga atg gag gat gac aag gta gca gaa gct gca      2238
Leu Leu Gln Cys Leu Arg Met Glu Asp Asp Lys Val Ala Glu Ala Ala
            685                 690                 695

ata caa att ttt aga aac aca ggc cac aaa ata gaa act gac ctt ccc      2286
Ile Gln Ile Phe Arg Asn Thr Gly His Lys Ile Glu Thr Asp Leu Pro
        700                 705                 710

cag ata cgg tca acc ttg atc ccc att tta cat cag aaa gcc aag cgg      2334
Gln Ile Arg Ser Thr Leu Ile Pro Ile Leu His Gln Lys Ala Lys Arg
    715                 720                 725

ggc act cca cac caa gca aag cag gct gtt cac tgc atc cat gcc atc      2382
Gly Thr Pro His Gln Ala Lys Gln Ala Val His Cys Ile His Ala Ile
730                 735                 740                 745

ttc tca aac aag gag gtc cag ctg gca cag att ttt gag cca ctc agt      2430
Phe Ser Asn Lys Glu Val Gln Leu Ala Gln Ile Phe Glu Pro Leu Ser
                750                 755                 760

agg agt ctg aat gct gat gta cca gag caa ctt ata act cca tta gtt      2478
Arg Ser Leu Asn Ala Asp Val Pro Glu Gln Leu Ile Thr Pro Leu Val
            765                 770                 775

tca ctg ggc cac att tcc atg tta gca cca gat cag ttt gcc tcc ccg      2526
Ser Leu Gly His Ile Ser Met Leu Ala Pro Asp Gln Phe Ala Ser Pro
        780                 785                 790

atg aaa tct gta gtg gca aac ttt att gtt aaa gac ctt cta atg aac      2574
Met Lys Ser Val Val Ala Asn Phe Ile Val Lys Asp Leu Leu Met Asn
    795                 800                 805

gac agg tca aca ggt gag aag aat gga aaa tta tgg tct cca gat gag      2622
Asp Arg Ser Thr Gly Glu Lys Asn Gly Lys Leu Trp Ser Pro Asp Glu
810                 815                 820                 825

gaa gtt tct cct gaa gtt cta gca aag gta cag gca att aaa ctt ctg      2670
Glu Val Ser Pro Glu Val Leu Ala Lys Val Gln Ala Ile Lys Leu Leu
                830                 835                 840

gta agg tgg ctg ttg ggt atg aaa aac aac cag tct aaa tct gcc aac      2718
Val Arg Trp Leu Leu Gly Met Lys Asn Asn Gln Ser Lys Ser Ala Asn
            845                 850                 855

tca act ctt cgg tta tta tca gcc atg ctg gtt agt gag ggc gac ctg      2766
Ser Thr Leu Arg Leu Leu Ser Ala Met Leu Val Ser Glu Gly Asp Leu
        860                 865                 870

aca gag caa aag agg atc agt aaa tct gat atg tct cgc ttg cga tta      2814
Thr Glu Gln Lys Arg Ile Ser Lys Ser Asp Met Ser Arg Leu Arg Leu
    875                 880                 885

gct gct ggt agt gcc ata atg aag ctt gct cag gaa cct tgc tac cat      2862
Ala Ala Gly Ser Ala Ile Met Lys Leu Ala Gln Glu Pro Cys Tyr His
890                 895                 900                 905

gaa att att acc cca gaa cag ttt cag ctc tgt gca ctg gtt att aat      2910
Glu Ile Ile Thr Pro Glu Gln Phe Gln Leu Cys Ala Leu Val Ile Asn
                910                 915                 920

gat gag tgc tac caa gta agg cag ata ttt gcc cag aag ctt cat aag      2958
Asp Glu Cys Tyr Gln Val Arg Gln Ile Phe Ala Gln Lys Leu His Lys
            925                 930                 935

gca ctt gtg aag ttg ctt ctc cca ctg gag tat atg gcc atc ttt gct      3006
Ala Leu Val Lys Leu Leu Leu Pro Leu Glu Tyr Met Ala Ile Phe Ala
        940                 945                 950

ttg tgt gcc aaa gac cct gtg aaa gaa agg aga gca cac gct cgg cag      3054
Leu Cys Ala Lys Asp Pro Val Lys Glu Arg Arg Ala His Ala Arg Gln
    955                 960                 965

tgt ttg tta aag aac atc agc atc cgc agg gag tac atc aaa cag aac      3102
Cys Leu Leu Lys Asn Ile Ser Ile Arg Arg Glu Tyr Ile Lys Gln Asn
```

-continued

```
970                 975                 980                 985

ccc atg gcc act gag aaa tta ttg tca ctg ctg cct gaa tat gtg  gtt     3150
Pro Met Ala Thr Glu Lys Leu Leu Ser Leu Leu Pro Glu Tyr Val  Val
                990                 995                 1000

cca tac atg att  cac ctc cta gcc cat  gat cct gat ttc aca  cgg      3195
Pro Tyr Met Ile  His Leu Leu Ala His  Asp Pro Asp Phe Thr  Arg
            1005                 1010                 1015

tca caa gat gtt  gat caa ctt cgt gat  ata aaa gag tgc ctg  tgg      3240
Ser Gln Asp Val  Asp Gln Leu Arg Asp  Ile Lys Glu Cys Leu  Trp
            1020                 1025                 1030

ttt atg ctt gaa  gtc tta atg aca aag  aat gaa aac aac agc  cat      3285
Phe Met Leu Glu  Val Leu Met Thr Lys  Asn Glu Asn Asn Ser  His
            1035                 1040                 1045

gca ttc atg aaa  aag atg gca gag aat  atc aag cta acc aga  gac      3330
Ala Phe Met Lys  Lys Met Ala Glu Asn  Ile Lys Leu Thr Arg  Asp
            1050                 1055                 1060

gcc cag tct ccc  gat gaa tcc aag aca  aat gaa aaa ctt tat  acg      3375
Ala Gln Ser Pro  Asp Glu Ser Lys Thr  Asn Glu Lys Leu Tyr  Thr
            1065                 1070                 1075

gtt tgt gac gtg  gct ctg tgt gtt ata  aat agt aaa agt gct  ttg      3420
Val Cys Asp Val  Ala Leu Cys Val Ile  Asn Ser Lys Ser Ala  Leu
            1080                 1085                 1090

tgc aat gca gac  tca cca aag gac cca  gtc ctc cca atg aag  ttc      3465
Cys Asn Ala Asp  Ser Pro Lys Asp Pro  Val Leu Pro Met Lys  Phe
            1095                 1100                 1105

ttt aca cag cct  gaa aag gac ttc tgt  aat gac aaa agc tat  att      3510
Phe Thr Gln Pro  Glu Lys Asp Phe Cys  Asn Asp Lys Ser Tyr  Ile
            1110                 1115                 1120

tca gaa gag aca  aga gtt ctt ctg tta  aca gga aag cca aag  cct      3555
Ser Glu Glu Thr  Arg Val Leu Leu Leu  Thr Gly Lys Pro Lys  Pro
            1125                 1130                 1135

act gga gta tta  ggt aca gtg aac aag  cct tta tca gca acg  gga      3600
Thr Gly Val Leu  Gly Thr Val Asn Lys  Pro Leu Ser Ala Thr  Gly
            1140                 1145                 1150

agg aag cct tat  gtt aga agc gcc ggc  aca gag act gga agc  aat      3645
Arg Lys Pro Tyr  Val Arg Ser Ala Gly  Thr Glu Thr Gly Ser  Asn
            1155                 1160                 1165

att aac gcc aat  tca gag ctg agt cct  tca gcc gga agt cgt  tca      3690
Ile Asn Ala Asn  Ser Glu Leu Ser Pro  Ser Ala Gly Ser Arg  Ser
            1170                 1175                 1180

agg gaa cag agt  tca gag gca tca gaa  act gga gtt agt gaa  aat      3735
Arg Glu Gln Ser  Ser Glu Ala Ser Glu  Thr Gly Val Ser Glu  Asn
            1185                 1190                 1195

gag gag aat cct  gtg aga ata att tct  gtc aca cct gta aag  aat      3780
Glu Glu Asn Pro  Val Arg Ile Ile Ser  Val Thr Pro Val Lys  Asn
            1200                 1205                 1210

att gat act gta  aag aat aag gaa att  aat tct gat cag tct  acc      3825
Ile Asp Thr Val  Lys Asn Lys Glu Ile  Asn Ser Asp Gln Ser  Thr
            1215                 1220                 1225

caa ggc aac atc  agc agt gac aga gga  aag aaa aga att gta  aca      3870
Gln Gly Asn Ile  Ser Ser Asp Arg Gly  Lys Lys Arg Ile Val  Thr
            1230                 1235                 1240

gca gct ggt gca  gag aat atc caa aag  cca gac gag aaa gta  gat      3915
Ala Ala Gly Ala  Glu Asn Ile Gln Lys  Pro Asp Glu Lys Val  Asp
            1245                 1250                 1255

gag tca gga ccg  cct gcc cct tcc aaa  ccc cgg aga gga cgt  cgc      3960
Glu Ser Gly Pro  Pro Ala Pro Ser Lys  Pro Arg Arg Gly Arg  Arg
            1260                 1265                 1270

ccc aaa tct gaa  tct cag ggc aat gca  acc aaa aac gat gat  cta      4005
```

```
Pro Lys Ser Glu  Ser Gln Gly Asn Ala  Thr Lys Asn Asp Asp  Leu
            1275                 1280                 1285

aat aaa cct gtt  agc aag gga agg aaa  aga gct gca ggc agc  cag      4050
Asn Lys Pro Val  Ser Lys Gly Arg Lys  Arg Ala Ala Gly Ser  Gln
            1290                 1295                 1300

gag agt ctg gag  gca ggg aat gcc aaa  gcg ccc aag cta caa  gat      4095
Glu Ser Leu Glu  Ala Gly Asn Ala Lys  Ala Pro Lys Leu Gln  Asp
            1305                 1310                 1315

gga gcc aaa aag  gca gtt cca gca gag  aga caa att gat tta  caa      4140
Gly Ala Lys Lys  Ala Val Pro Ala Glu  Arg Gln Ile Asp Leu  Gln
            1320                 1325                 1330

agg taa tgtgacccca ctcatcctca ccttgtcagc agtgggaatg gctggcaata      4196
Arg

gcagatactc agtgtaggat ggactctggc tctgacggag cgggcttccc cacattaccc   4256

attgtatggg aaatagaaag catcttcatt atgtgtactg ctatatatag taaatgtaaa   4316

aaatgagtgt gatggtgcac acgtgtaatc ccagcccttg gaggcagaaa gggggttatg   4376

agtttaaaac cacgctgggc tgtgtagtaa gactttgtct ttaaaaagtg gggagggagg   4436

gcaaggaggg tagaga                                                   4452


<210> SEQ ID NO 6
<211> LENGTH: 1332
<212> TYPE: PRT
<213> ORGANISM: Mus musculus

<400> SEQUENCE: 6

Met Asp Phe Thr Gln Pro Lys Pro Ala Thr Ala Leu Cys Gly Val Val
1               5                   10                  15

Ser Ala Asp Gly Lys Ile Ala Tyr Pro Pro Gly Val Lys Glu Ile Thr
            20                  25                  30

Asp Lys Ile Thr Thr Asp Glu Met Ile Lys Arg Leu Lys Met Val Val
        35                  40                  45

Lys Thr Phe Met Asp Met Asp Gln Asp Ser Glu Asp Glu Lys Gln Gln
    50                  55                  60

Tyr Leu Pro Leu Ala Leu His Leu Ala Ser Glu Phe Phe Leu Arg Asn
65                  70                  75                  80

Pro Asn Lys Asp Val Arg Leu Leu Val Ala Cys Cys Leu Ala Asp Ile
                85                  90                  95

Phe Arg Ile Tyr Ala Pro Glu Ala Pro Tyr Thr Ser His Asp Lys Leu
            100                 105                 110

Lys Asp Ile Phe Leu Phe Ile Thr Arg Gln Leu Lys Gly Leu Glu Asp
        115                 120                 125

Thr Lys Ser Pro Gln Phe Asn Arg Tyr Phe Tyr Leu Leu Glu Asn Leu
    130                 135                 140

Ala Trp Val Lys Ser Tyr Asn Ile Cys Phe Glu Leu Glu Asp Cys Asn
145                 150                 155                 160

Glu Ile Phe Ile Gln Leu Phe Arg Thr Leu Phe Ser Val Ile Asn Asn
                165                 170                 175

Ser His Asn Thr Lys Val Gln Met His Met Leu Asp Leu Met Ser Ser
            180                 185                 190

Ile Ile Met Glu Gly Asp Gly Val Thr Gln Glu Leu Leu Asp Ser Ile
        195                 200                 205

Leu Ile Asn Leu Ile Pro Ala His Lys Asn Leu Asn Lys Gln Ser Phe
    210                 215                 220

Asp Leu Ala Lys Val Leu Leu Lys Arg Thr Val Gln Thr Ile Glu Ala
```

```
225                 230                 235                 240

Cys Ile Ala Asn Phe Phe Asn Gln Val Leu Val Leu Gly Arg Ser Ser
                245                 250                 255

Val Ser Asp Leu Ser Glu His Val Phe Asp Leu Ile Gln Glu Leu Phe
            260                 265                 270

Ala Ile Asp Pro Gln Leu Leu Leu Ser Val Met Pro Gln Leu Glu Phe
        275                 280                 285

Lys Leu Lys Ser Asn Asp Gly Glu Glu Arg Leu Ala Val Val Arg Leu
    290                 295                 300

Leu Ala Lys Leu Phe Gly Ser Lys Asp Ser Asp Leu Ala Thr Gln Asn
305                 310                 315                 320

Arg Pro Leu Trp Gln Cys Phe Leu Gly Arg Phe Asn Asp Ile His Val
                325                 330                 335

Pro Val Arg Leu Glu Ser Val Lys Phe Ala Ser His Cys Leu Met Asn
            340                 345                 350

His Pro Asp Leu Ala Lys Asp Leu Thr Glu Tyr Leu Lys Val Arg Ser
        355                 360                 365

His Asp Pro Glu Glu Ala Ile Arg His Asp Val Ile Val Thr Ile Ile
    370                 375                 380

Thr Ala Ala Lys Arg Asp Leu Ala Leu Val Asn Asp Gln Leu Leu Gly
385                 390                 395                 400

Phe Val Arg Glu Arg Thr Leu Asp Lys Arg Trp Arg Val Arg Lys Glu
                405                 410                 415

Ala Met Met Gly Leu Ala Gln Leu Tyr Lys Lys Tyr Cys Leu His Gly
            420                 425                 430

Glu Ala Gly Lys Glu Ala Ala Glu Lys Val Ser Trp Ile Lys Asp Lys
        435                 440                 445

Leu Leu His Ile Tyr Tyr Gln Asn Ser Ile Asp Asp Lys Leu Leu Val
    450                 455                 460

Glu Lys Ile Phe Ala Gln Tyr Leu Val Pro His Asn Leu Glu Thr Glu
465                 470                 475                 480

Glu Arg Met Lys Cys Leu Tyr Tyr Leu Tyr Ala Ser Leu Asp Pro Asn
                485                 490                 495

Ala Val Lys Ala Leu Asn Glu Met Trp Lys Cys Gln Asn Met Leu Arg
            500                 505                 510

Ser His Val Arg Glu Leu Leu Asp Leu His Lys Gln Pro Thr Ser Glu
        515                 520                 525

Ala Asn Cys Ser Ala Met Phe Gly Lys Leu Met Thr Ile Ala Lys Asn
    530                 535                 540

Leu Pro Asp Pro Gly Lys Ala Gln Asp Phe Val Lys Lys Phe Asn Gln
545                 550                 555                 560

Val Leu Gly Asp Asp Glu Lys Leu Arg Ser Gln Leu Glu Leu Leu Ile
                565                 570                 575

Ser Pro Thr Cys Ser Cys Lys Gln Ala Asp Val Cys Val Arg Glu Ile
            580                 585                 590

Ala Arg Lys Leu Ala Asn Pro Lys Gln Pro Thr Asn Pro Phe Leu Glu
        595                 600                 605

Met Val Lys Phe Leu Leu Glu Arg Ile Ala Pro Val His Ile Asp Ser
    610                 615                 620

Glu Ala Ile Ser Ala Leu Val Lys Leu Met Asn Lys Ser Ile Glu Gly
625                 630                 635                 640

Thr Ala Asp Asp Glu Glu Glu Gly Val Ser Pro Asp Ser Ala Ile Arg
                645                 650                 655
```

```
Ser Gly Leu Glu Leu Leu Lys Val Leu Ser Phe Thr His Pro Thr Ser
            660                 665                 670

Phe His Ser Ala Glu Thr Tyr Glu Ser Leu Leu Gln Cys Leu Arg Met
        675                 680                 685

Glu Asp Asp Lys Val Ala Glu Ala Ala Ile Gln Ile Phe Arg Asn Thr
    690                 695                 700

Gly His Lys Ile Glu Thr Asp Leu Pro Gln Ile Arg Ser Thr Leu Ile
705                 710                 715                 720

Pro Ile Leu His Gln Lys Ala Lys Arg Gly Thr Pro His Gln Ala Lys
                725                 730                 735

Gln Ala Val His Cys Ile His Ala Ile Phe Ser Asn Lys Glu Val Gln
            740                 745                 750

Leu Ala Gln Ile Phe Glu Pro Leu Ser Arg Ser Leu Asn Ala Asp Val
        755                 760                 765

Pro Glu Gln Leu Ile Thr Pro Leu Val Ser Leu Gly His Ile Ser Met
    770                 775                 780

Leu Ala Pro Asp Gln Phe Ala Ser Pro Met Lys Ser Val Val Ala Asn
785                 790                 795                 800

Phe Ile Val Lys Asp Leu Leu Met Asn Asp Arg Ser Thr Gly Glu Lys
                805                 810                 815

Asn Gly Lys Leu Trp Ser Pro Asp Glu Glu Val Ser Pro Glu Val Leu
            820                 825                 830

Ala Lys Val Gln Ala Ile Lys Leu Leu Val Arg Trp Leu Leu Gly Met
        835                 840                 845

Lys Asn Asn Gln Ser Lys Ser Ala Asn Ser Thr Leu Arg Leu Leu Ser
    850                 855                 860

Ala Met Leu Val Ser Glu Gly Asp Leu Thr Glu Gln Lys Arg Ile Ser
865                 870                 875                 880

Lys Ser Asp Met Ser Arg Leu Arg Leu Ala Ala Gly Ser Ala Ile Met
                885                 890                 895

Lys Leu Ala Gln Glu Pro Cys Tyr His Glu Ile Ile Thr Pro Glu Gln
            900                 905                 910

Phe Gln Leu Cys Ala Leu Val Ile Asn Asp Glu Cys Tyr Gln Val Arg
        915                 920                 925

Gln Ile Phe Ala Gln Lys Leu His Lys Ala Leu Val Lys Leu Leu Leu
    930                 935                 940

Pro Leu Glu Tyr Met Ala Ile Phe Ala Leu Cys Ala Lys Asp Pro Val
945                 950                 955                 960

Lys Glu Arg Arg Ala His Ala Arg Gln Cys Leu Leu Lys Asn Ile Ser
                965                 970                 975

Ile Arg Arg Glu Tyr Ile Lys Gln Asn Pro Met Ala Thr Glu Lys Leu
            980                 985                 990

Leu Ser Leu Leu Pro Glu Tyr Val  Val Pro Tyr Met Ile  His Leu Leu
        995                 1000                1005

Ala His  Asp Pro Asp Phe Thr  Arg Ser Gln Asp Val  Asp Gln Leu
    1010                 1015                1020

Arg Asp  Ile Lys Glu Cys Leu  Trp Phe Met Leu Glu  Val Leu Met
    1025                 1030                1035

Thr Lys  Asn Glu Asn Asn Ser  His Ala Phe Met Lys  Lys Met Ala
    1040                 1045                1050

Glu Asn  Ile Lys Leu Thr Arg  Asp Ala Gln Ser Pro  Asp Glu Ser
    1055                 1060                1065
```

```
Lys Thr  Asn Glu Lys Leu Tyr  Thr Val Cys Asp Val  Ala Leu Cys
    1070                 1075                 1080

Val Ile  Asn Ser Lys Ser Ala  Leu Cys Asn Ala Asp  Ser Pro Lys
    1085                 1090                 1095

Asp Pro  Val Leu Pro Met Lys  Phe Phe Thr Gln Pro  Glu Lys Asp
    1100                 1105                 1110

Phe Cys  Asn Asp Lys Ser Tyr  Ile Ser Glu Glu Thr  Arg Val Leu
    1115                 1120                 1125

Leu Leu  Thr Gly Lys Pro Lys  Pro Thr Gly Val Leu  Gly Thr Val
    1130                 1135                 1140

Asn Lys  Pro Leu Ser Ala Thr  Gly Arg Lys Pro Tyr  Val Arg Ser
    1145                 1150                 1155

Ala Gly  Thr Glu Thr Gly Ser  Asn Ile Asn Ala Asn  Ser Glu Leu
    1160                 1165                 1170

Ser Pro  Ser Ala Gly Ser Arg  Ser Arg Glu Gln Ser  Ser Glu Ala
    1175                 1180                 1185

Ser Glu  Thr Gly Val Ser Glu  Asn Glu Glu Asn Pro  Val Arg Ile
    1190                 1195                 1200

Ile Ser  Val Thr Pro Val Lys  Asn Ile Asp Thr Val  Lys Asn Lys
    1205                 1210                 1215

Glu Ile  Asn Ser Asp Gln Ser  Thr Gln Gly Asn Ile  Ser Ser Asp
    1220                 1225                 1230

Arg Gly  Lys Lys Arg Ile Val  Thr Ala Ala Gly Ala  Glu Asn Ile
    1235                 1240                 1245

Gln Lys  Pro Asp Glu Lys Val  Asp Glu Ser Gly Pro  Pro Ala Pro
    1250                 1255                 1260

Ser Lys  Pro Arg Arg Gly Arg  Arg Pro Lys Ser Glu  Ser Gln Gly
    1265                 1270                 1275

Asn Ala  Thr Lys Asn Asp Asp  Leu Asn Lys Pro Val  Ser Lys Gly
    1280                 1285                 1290

Arg Lys  Arg Ala Ala Gly Ser  Gln Glu Ser Leu Glu  Ala Gly Asn
    1295                 1300                 1305

Ala Lys  Ala Pro Lys Leu Gln  Asp Gly Ala Lys Lys  Ala Val Pro
    1310                 1315                 1320

Ala Glu  Arg Gln Ile Asp Leu  Gln Arg
    1325                 1330


<210> SEQ ID NO 7
<211> LENGTH: 6553
<212> TYPE: DNA
<213> ORGANISM: Bos taurus
<220> FEATURE:
<221> NAME/KEY: CDS
<222> LOCATION: (1)..(3912)
<223> OTHER INFORMATION:

<400> SEQUENCE: 7

atg gac ttc acc gcg cag ccc aag cct gcc act gcc ctc tgt ggc gtc       48
Met Asp Phe Thr Ala Gln Pro Lys Pro Ala Thr Ala Leu Cys Gly Val
1               5                   10                  15

gtg agt gcc gac ggg aag atc gct tac cct ccg ggg gta aag gag atc       96
Val Ser Ala Asp Gly Lys Ile Ala Tyr Pro Pro Gly Val Lys Glu Ile
            20                  25                  30

acc gac aag atc acc acg gac gaa atg atc aaa cga ctg aag atg gta      144
Thr Asp Lys Ile Thr Thr Asp Glu Met Ile Lys Arg Leu Lys Met Val
        35                  40                  45

gta aag act ttt atg gat atg gat cag gac tca gaa gat gaa aaa cag      192
```

```
Val Lys Thr Phe Met Asp Met Asp Gln Asp Ser Glu Asp Glu Lys Gln
    50                  55                  60

cag tat ctc cca cta gcc ttg cat cta gca tct gaa ttt ttc ctc agg      240
Gln Tyr Leu Pro Leu Ala Leu His Leu Ala Ser Glu Phe Phe Leu Arg
65                  70                  75                  80

aat ccc aat aaa gat gtg cgt ctc ctt gta gca tgt tgt ttg gct gac      288
Asn Pro Asn Lys Asp Val Arg Leu Leu Val Ala Cys Cys Leu Ala Asp
                85                  90                  95

atc ttt cga atc tat gcc cca gaa gct cca tat act tcc cat gat aaa      336
Ile Phe Arg Ile Tyr Ala Pro Glu Ala Pro Tyr Thr Ser His Asp Lys
            100                 105                 110

ctt aag gac ata ttt ttg ttt att acc aga cag tta aaa ggt ttg gag      384
Leu Lys Asp Ile Phe Leu Phe Ile Thr Arg Gln Leu Lys Gly Leu Glu
        115                 120                 125

gat aca aag agc ccg cag ttt aat aga tac ttt tat tta tta gag aat      432
Asp Thr Lys Ser Pro Gln Phe Asn Arg Tyr Phe Tyr Leu Leu Glu Asn
    130                 135                 140

tta gca tgg gtt aaa tcg tat aac atc tgc ttt gaa ttg gaa gat tgc      480
Leu Ala Trp Val Lys Ser Tyr Asn Ile Cys Phe Glu Leu Glu Asp Cys
145                 150                 155                 160

aat gaa att ttt att cag ctt ttt agg act ctc ttc tca gtg atc aac      528
Asn Glu Ile Phe Ile Gln Leu Phe Arg Thr Leu Phe Ser Val Ile Asn
                165                 170                 175

aat agc cac aat aag aag gta caa atg cac atg tta gac ttg atg agt      576
Asn Ser His Asn Lys Lys Val Gln Met His Met Leu Asp Leu Met Ser
            180                 185                 190

tct atc atc atg gaa ggt gat gga gtt act caa gaa tta ttg gac tcc      624
Ser Ile Ile Met Glu Gly Asp Gly Val Thr Gln Glu Leu Leu Asp Ser
        195                 200                 205

att ctt att aac ctc att cct gca cat aag aac tta aat aaa cag tcg      672
Ile Leu Ile Asn Leu Ile Pro Ala His Lys Asn Leu Asn Lys Gln Ser
    210                 215                 220

ttt gac ctc gca aaa gtc cta ttg aaa agg aca gtc cag act att gaa      720
Phe Asp Leu Ala Lys Val Leu Leu Lys Arg Thr Val Gln Thr Ile Glu
225                 230                 235                 240

gca tgc att gcc aat ttt ttc aat caa gta ctg gtg ctg gga aga tca      768
Ala Cys Ile Ala Asn Phe Phe Asn Gln Val Leu Val Leu Gly Arg Ser
                245                 250                 255

tca gta agt gat ttg tca gaa cat gta ttt gat ctg att cag gaa ctt      816
Ser Val Ser Asp Leu Ser Glu His Val Phe Asp Leu Ile Gln Glu Leu
            260                 265                 270

ttt gct ata gat ccc cat tta tta tta tct gtt atg ccg cag ctt gaa      864
Phe Ala Ile Asp Pro His Leu Leu Leu Ser Val Met Pro Gln Leu Glu
        275                 280                 285

ttc aaa ctg aag agc aat gat gga gaa gaa cga tta gct gtt gtt cga      912
Phe Lys Leu Lys Ser Asn Asp Gly Glu Glu Arg Leu Ala Val Val Arg
    290                 295                 300

ctt tta gct aaa ttg ttt ggc tct aaa gat tcc gat tta gca aca cag      960
Leu Leu Ala Lys Leu Phe Gly Ser Lys Asp Ser Asp Leu Ala Thr Gln
305                 310                 315                 320

aat cgt cct ctg tgg cag tgt ttt ctt gga cga ttt aat gac att cat     1008
Asn Arg Pro Leu Trp Gln Cys Phe Leu Gly Arg Phe Asn Asp Ile His
                325                 330                 335

gtt cct gtg aga tta gaa agt gtg aaa ttt gcc agt cac tgt tta atg     1056
Val Pro Val Arg Leu Glu Ser Val Lys Phe Ala Ser His Cys Leu Met
            340                 345                 350

aat cac cca gat tta gca aag gat ctc aca ggt ttc act ctg gca ctg     1104
Asn His Pro Asp Leu Ala Lys Asp Leu Thr Gly Phe Thr Leu Ala Leu
        355                 360                 365
```

```
ttt cag gtc tct aac agt cat gga cta tgg cga gta aga aaa gaa gct      1152
Phe Gln Val Ser Asn Ser His Gly Leu Trp Arg Val Arg Lys Glu Ala
    370                 375                 380

atg atg ggt ctg gct cag ctt tat aag aaa tac tgt ctt cat ggt gaa      1200
Met Met Gly Leu Ala Gln Leu Tyr Lys Lys Tyr Cys Leu His Gly Glu
385                 390                 395                 400

gca gga aag gaa gct gca gag aaa gtc agc tgg ata aag gac aaa ctt      1248
Ala Gly Lys Glu Ala Ala Glu Lys Val Ser Trp Ile Lys Asp Lys Leu
                405                 410                 415

ttg cat ata tat tat caa aat agc atc gat gac aaa cta ttg gta gag      1296
Leu His Ile Tyr Tyr Gln Asn Ser Ile Asp Asp Lys Leu Leu Val Glu
            420                 425                 430

aaa atc ttt gct caa tat ctt gtc ccc cac aac ctg gaa aca gaa gag      1344
Lys Ile Phe Ala Gln Tyr Leu Val Pro His Asn Leu Glu Thr Glu Glu
        435                 440                 445

aga atg aaa tgc ttg tat tat tta tat gct agt ttg gat cca aat gct      1392
Arg Met Lys Cys Leu Tyr Tyr Leu Tyr Ala Ser Leu Asp Pro Asn Ala
    450                 455                 460

gtc aaa gct ctc aat gaa atg tgg aag tgt cag aac atg ctt aga agt      1440
Val Lys Ala Leu Asn Glu Met Trp Lys Cys Gln Asn Met Leu Arg Ser
465                 470                 475                 480

cat gta cga gaa ctg ttg gat ttg cac aag cag cct aca tca gaa gct      1488
His Val Arg Glu Leu Leu Asp Leu His Lys Gln Pro Thr Ser Glu Ala
                485                 490                 495

aac tgt tct gct atg ttt gga aaa ctg atg acc ata gca aag aat ttg      1536
Asn Cys Ser Ala Met Phe Gly Lys Leu Met Thr Ile Ala Lys Asn Leu
            500                 505                 510

cct gat cct ggg aaa gca caa gat ttt gtg aag aaa ttt aac caa gtt      1584
Pro Asp Pro Gly Lys Ala Gln Asp Phe Val Lys Lys Phe Asn Gln Val
        515                 520                 525

ctt ggt gat gat gag aaa ctg cga tct cag ttg gag ttg tta atc agt      1632
Leu Gly Asp Asp Glu Lys Leu Arg Ser Gln Leu Glu Leu Leu Ile Ser
    530                 535                 540

cca acc tgt tcg tgc aaa cag gca gat gtt tgt gtg aga gaa ata gcc      1680
Pro Thr Cys Ser Cys Lys Gln Ala Asp Val Cys Val Arg Glu Ile Ala
545                 550                 555                 560

cgg aaa ctt gcc aat cct aag cag cca aca aat cct ttt cta gag atg      1728
Arg Lys Leu Ala Asn Pro Lys Gln Pro Thr Asn Pro Phe Leu Glu Met
                565                 570                 575

gtc aaa ttt ctg ttg gaa aga att gca cct gtg cac att gat tca gaa      1776
Val Lys Phe Leu Leu Glu Arg Ile Ala Pro Val His Ile Asp Ser Glu
            580                 585                 590

gcc atc agt gca ctg gta aaa ctg atg aat aaa tca ata gaa ggg aca      1824
Ala Ile Ser Ala Leu Val Lys Leu Met Asn Lys Ser Ile Glu Gly Thr
        595                 600                 605

gca gat gac gaa gag gag ggt gta agt cca gat aca gct att cgt tca      1872
Ala Asp Asp Glu Glu Glu Gly Val Ser Pro Asp Thr Ala Ile Arg Ser
    610                 615                 620

gga ctt gaa ctt ctt aag gtt ctg tct ttc aca cat cct acc tcg ttc      1920
Gly Leu Glu Leu Leu Lys Val Leu Ser Phe Thr His Pro Thr Ser Phe
625                 630                 635                 640

cac tct gca gag aca tat gag tcc ctg ttg cag tgc ctc aga atg gaa      1968
His Ser Ala Glu Thr Tyr Glu Ser Leu Leu Gln Cys Leu Arg Met Glu
                645                 650                 655

gat gac aag gta gca gaa gcc gcc ata cag att ttt aga aac aca ggc      2016
Asp Asp Lys Val Ala Glu Ala Ala Ile Gln Ile Phe Arg Asn Thr Gly
            660                 665                 670

cac aaa ata gaa aca gac cta ccc cag ata cgg tcg acc tta att ccc      2064
His Lys Ile Glu Thr Asp Leu Pro Gln Ile Arg Ser Thr Leu Ile Pro
        675                 680                 685
```

```
att tta cat cag aaa gca aag aga gga act cca cac caa gca aaa cag     2112
Ile Leu His Gln Lys Ala Lys Arg Gly Thr Pro His Gln Ala Lys Gln
    690                 695                 700

gct gtt cac tgt ata cat gcc ata ttc aca aat aaa gaa gtc cag ctt     2160
Ala Val His Cys Ile His Ala Ile Phe Thr Asn Lys Glu Val Gln Leu
705                 710                 715                 720

gca cag att ttt gag cca ctc agt agg agt ctg aat gct gac gta cca     2208
Ala Gln Ile Phe Glu Pro Leu Ser Arg Ser Leu Asn Ala Asp Val Pro
                725                 730                 735

gaa caa ctt ata act ccg tta gtt tca ttg ggc cac att tct atg tta     2256
Glu Gln Leu Ile Thr Pro Leu Val Ser Leu Gly His Ile Ser Met Leu
            740                 745                 750

gca cca gat cag ttt gct tcc cca atg aaa tct gta gta gca aat ttt     2304
Ala Pro Asp Gln Phe Ala Ser Pro Met Lys Ser Val Val Ala Asn Phe
        755                 760                 765

att gtt aaa gat cta cta atg aat gac agg tca aca ggt gag aag aat     2352
Ile Val Lys Asp Leu Leu Met Asn Asp Arg Ser Thr Gly Glu Lys Asn
    770                 775                 780

gga aaa tta tgg tct cca gat gaa gag gtt tcc cct gaa gta cta gca     2400
Gly Lys Leu Trp Ser Pro Asp Glu Glu Val Ser Pro Glu Val Leu Ala
785                 790                 795                 800

aag gta cag gca att aaa ctt ctg gta aga tgg ctg ttg ggt atg aaa     2448
Lys Val Gln Ala Ile Lys Leu Leu Val Arg Trp Leu Leu Gly Met Lys
                805                 810                 815

aac aac cag tct aaa tct gcc aat tca act ctt cgg tta tta tca gca     2496
Asn Asn Gln Ser Lys Ser Ala Asn Ser Thr Leu Arg Leu Leu Ser Ala
            820                 825                 830

atg ttg gtt agt gag ggt gac ctg aca gag cag aag agg atc agt aaa     2544
Met Leu Val Ser Glu Gly Asp Leu Thr Glu Gln Lys Arg Ile Ser Lys
        835                 840                 845

tct gat atg tct cgc ttg cga tta gct gct ggt agt gcc ata atg aag     2592
Ser Asp Met Ser Arg Leu Arg Leu Ala Ala Gly Ser Ala Ile Met Lys
    850                 855                 860

ctt gct cag gaa cct tgt tac cat gaa att ata acc cca gaa cag ttt     2640
Leu Ala Gln Glu Pro Cys Tyr His Glu Ile Ile Thr Pro Glu Gln Phe
865                 870                 875                 880

cag ctc tgt gca ctt gtt att aat gat gag tgc tat caa gta agg cag     2688
Gln Leu Cys Ala Leu Val Ile Asn Asp Glu Cys Tyr Gln Val Arg Gln
                885                 890                 895

ata ttt gct cag aag cta cac aag gca ctt gtg aag tta ctg ctc cca     2736
Ile Phe Ala Gln Lys Leu His Lys Ala Leu Val Lys Leu Leu Leu Pro
            900                 905                 910

ttg gag tat atg gcc atc ttt gcc ttg tgt gcc aaa gat cct gtg aag     2784
Leu Glu Tyr Met Ala Ile Phe Ala Leu Cys Ala Lys Asp Pro Val Lys
        915                 920                 925

gag aga aga gca cat gca cga cag tgt tta cta aaa aac atc agt ata     2832
Glu Arg Arg Ala His Ala Arg Gln Cys Leu Leu Lys Asn Ile Ser Ile
    930                 935                 940

cgc agg gag tac att aaa cag aac ccc atg gct act gag aaa cta tta     2880
Arg Arg Glu Tyr Ile Lys Gln Asn Pro Met Ala Thr Glu Lys Leu Leu
945                 950                 955                 960

tca ctg ttg cct gag tat gta gtt ccg tat atg att cac ctg cta gct     2928
Ser Leu Leu Pro Glu Tyr Val Val Pro Tyr Met Ile His Leu Leu Ala
                965                 970                 975

cat gat cca gat ttt aca aga tca caa gat gtt gat cag ctt cgt gat     2976
His Asp Pro Asp Phe Thr Arg Ser Gln Asp Val Asp Gln Leu Arg Asp
            980                 985                 990

att aaa gag tgc ctc tgg ttc atg  ctt gaa gtt tta atg  aca aaa aat   3024
Ile Lys Glu Cys Leu Trp Phe Met  Leu Glu Val Leu Met  Thr Lys Asn
```

```
        995                 1000                1005

gaa aat  aat agc cat gcc ttt  atg aaa aag atg gca  gag aat atc      3069
Glu Asn  Asn Ser His Ala Phe  Met Lys Lys Met Ala  Glu Asn Ile
    1010                 1015                 1020

aag cta  aca aaa gat gcc cag  tct cca gat gaa tcc  aag aca aat      3114
Lys Leu  Thr Lys Asp Ala Gln  Ser Pro Asp Glu Ser  Lys Thr Asn
    1025                 1030                 1035

gaa aaa  ctt tat aca gtg tgt  gat gtg gcc ctg tgc  gtg ata aat      3159
Glu Lys  Leu Tyr Thr Val Cys  Asp Val Ala Leu Cys  Val Ile Asn
    1040                 1045                 1050

agt aaa  agt gct ttg tgc aat  gca gag tca cca aag  gat cca gtc      3204
Ser Lys  Ser Ala Leu Cys Asn  Ala Glu Ser Pro Lys  Asp Pro Val
    1055                 1060                 1065

ctg cca  gtg aaa ttt ttt aca  caa cct gaa aag gac  ttc tgt aat      3249
Leu Pro  Val Lys Phe Phe Thr  Gln Pro Glu Lys Asp  Phe Cys Asn
    1070                 1075                 1080

gac aag  agt tat att tca gaa  gag aca aga gta ctt  ctg tta aca      3294
Asp Lys  Ser Tyr Ile Ser Glu  Glu Thr Arg Val Leu  Leu Leu Thr
    1085                 1090                 1095

gga aag  cca aaa cct gct gga  gta cta ggt gct gta  aac aag cct      3339
Gly Lys  Pro Lys Pro Ala Gly  Val Leu Gly Ala Val  Asn Lys Pro
    1100                 1105                 1110

ttg tca  gca acg gga agg aaa  cca tat gtt aga agc  act gga gct      3384
Leu Ser  Ala Thr Gly Arg Lys  Pro Tyr Val Arg Ser  Thr Gly Ala
    1115                 1120                 1125

gag acc  gga agc aat att aat  gta aat tca gag ctg  aac cct tcc      3429
Glu Thr  Gly Ser Asn Ile Asn  Val Asn Ser Glu Leu  Asn Pro Ser
    1130                 1135                 1140

acc gga  aat cga cca agg gaa  cag agt tca gag gca  gca gaa act      3474
Thr Gly  Asn Arg Pro Arg Glu  Gln Ser Ser Glu Ala  Ala Glu Thr
    1145                 1150                 1155

ggt gtt  agt gaa aat gag gag  aac cct gta aga att  att tct gtc      3519
Gly Val  Ser Glu Asn Glu Glu  Asn Pro Val Arg Ile  Ile Ser Val
    1160                 1165                 1170

aca cca  gta aag aat att gac  cca gta aag aat aag  gaa att aat      3564
Thr Pro  Val Lys Asn Ile Asp  Pro Val Lys Asn Lys  Glu Ile Asn
    1175                 1180                 1185

tct gat  cag tct gcc cag ggc  aac atc agc agt gac  cga gga aag      3609
Ser Asp  Gln Ser Ala Gln Gly  Asn Ile Ser Ser Asp  Arg Gly Lys
    1190                 1195                 1200

aaa aga  aca gta aca gca gct  ggt gca gag aat atc  caa caa aaa      3654
Lys Arg  Thr Val Thr Ala Ala  Gly Ala Glu Asn Ile  Gln Gln Lys
    1205                 1210                 1215

aca gat  gag aaa gca gat gaa  tca gga cca cct gcc  cct tca aaa      3699
Thr Asp  Glu Lys Ala Asp Glu  Ser Gly Pro Pro Ala  Pro Ser Lys
    1220                 1225                 1230

ccc agg  aga gga cgt cga ccc  aaa tct gaa tct cag  ggc aat gca      3744
Pro Arg  Arg Gly Arg Arg Pro  Lys Ser Glu Ser Gln  Gly Asn Ala
    1235                 1240                 1245

acc aaa  aat gat gat ata aat  aaa cct ctt agt aag  gga aga aag      3789
Thr Lys  Asn Asp Asp Ile Asn  Lys Pro Leu Ser Lys  Gly Arg Lys
    1250                 1255                 1260

aga gct  gca gtc agt cag gag  agc cct gga ggt ctg  gaa gca ggt      3834
Arg Ala  Ala Val Ser Gln Glu  Ser Pro Gly Gly Leu  Glu Ala Gly
    1265                 1270                 1275

aat gcc  aaa gca ccc aaa ctg  caa gac aca gcc aaa  aag gca gca      3879
Asn Ala  Lys Ala Pro Lys Leu  Gln Asp Thr Ala Lys  Lys Ala Ala
    1280                 1285                 1290

ccg aca  gag aga cag att gac  ttg caa agg taa taaatttatt            3922
```

```
Pro Thr  Glu Arg Gln Ile Asp  Leu Gln Arg
    1295                 1300

tgcaaaggga gaaaatgaag gccaaacaga agcaggctct agcttctgca aaaacttgga   3982

ttcagaatga tgttgaacag acaatgaagc taacttcaga acacactttc tgccttgaaa   4042

actgaaaaaa gctattactt cctttttca catgaccaca actcctttga tggaaatgta    4102

cagcagaaac tcttgagaga gaggctaaaa gcaactcttt tccaccctcc ccccagactt   4162

ttcttatgaa aagtcaataa ttaagcaaat tgcttaacac ttggttccag ttcctgcata   4222

tctggagttt aacggcataa tacaccatta atttccatgc tgcagtcttt attttaaaga   4282

aagtaacagg atgtccttac actgacaatg aaaattcatc aattttagag ccaggaattt   4342

cccgtgttac acaagaaaaa atagaagtct actgaattaa ttttttagaa gaagagaaat   4402

cagattaaat gtcttttttt tttccttttg gaaactttta tgtataattc tttctgcctg   4462

cctacttttc tgcaaaatga gatgtacaga tttcagttcc ctgctatgaa aagtgatgtg   4522

gtggcaattt tataaatgtt gctttctgat ttttatcaga gtgagaaaat aattaaaatt   4582

attattgatt tcatatcact tcatattttg atttcccctc cattttagtt taatataatt   4642

tgcaataaat gtacatattg ttgtctgttt cataaagcat atcactttaa agtggttttt   4702

actcctgtga ttatgttgga atatttgaaa ttttaaagga gtaaaaactg tccagcattt   4762

ggttttataa tgtttgtcac cagattttta ttattgatgt aaaaaaaagt caattctttt   4822

taaatagttg gactttggca gctttgtaag gaaagtggga ggtgcttagg attgctatca   4882

atttcagcat tgtgctgttg ggaataagtg ttttgctttt gtctgccagt ctgggctccg   4942

tttttatgtt ttttttgaag acaactattg catcaatata ttgtttcttg gcattgttca   5002

gcataggtaa tgtgtgcact tttcgtgtac acatattcat atttaagttt tttgcataaa   5062

ataaatgctt ctagatgtca tatggtagtc ttttttaatc tttttatcac attatgtttt   5122

cctgtgcagt ttttatgtga aagggctaaa gttataaaga aacaacatga ttacagtcaa   5182

ctctccatta tctatacaaa acagtgacta tgcctcaggt tttggatttt gcataaaatc   5242

acgtaattaa tcataaaatt aaagtaacaa agcataccgt aagagctaat tcaggaggaa   5302

ctcgagattg gtcctttctc acctgccccc actctccact taagcccttt ccccaaagcc   5362

ccatctgaat gtgctcagtg tccttgcgca cacctggcgt gggtttgagg acataaatgt   5422

ttgtgtgata acttggtctt gacaggctgt aagtctacgt gagatgtaaa gagtgaacat   5482

gacctgtgtc caaaaaggat gataatgtta aatgtaaaat ttgttggtag taaatgtcac   5542

ttaatgttct cataggtaat caagagttgg ctgtatactg actgactgaa agatggataa   5602

ttctcttaaa tatgcatata cacacattta ggtattggat gatggctagg gaacaatgga   5662

taccagatat tacctttttaa aagggcagaa aaagttctac tcttccttat tgcctcttca  5722

taatccttta gaaagataag atattgcctc caacatgctg aaaaagaata tctatgcata   5782

agcatcagag aagtccctca agccatcagt gggcatgttc tgtttagatg ttgaagttct   5842

cttagcatca gacagcttga ttcttaaggc caccaatttg ccaccaataa aaagcacact   5902

ggtagaggcc gcctctctct cgtctccttt taactgacca ttcagcatca tagctgacta   5962

gattacctag cgtgaagtca tagctaacgt agtgtagcag ccattcccat cagttatggc   6022

tgcttagatt tttgcaagag agaagttagc tcaaaggatc tggtccatat acaaaatgta   6082

aatggcccac cttggatttt ttttaatacg aagcaagtgt ctggcactaa gggatgggag   6142

agtaggactg agctgatggg gagggactta agggaaattt gtcatttttc ctttgaaaaa   6202
```

```
ggaaaaagta aaatctctta ggaatttggt attcacatct cagagaaata caacacaaag   6262

tgcagactta tatttgagaa ttaatgttaa ccctttgtgt ctagtttgaa gcttcttgta   6322

tttgtctaaa actacaagcc agaattttgt atctcctttg ataaaaagtg tgtataatgt   6382

aaagtagttt tgcatattct tgtgctgcac atgggctgaa tttttaaaaa attttttaaa   6442

agacttgaag agaaccttgt aatttgtgta aatgacaagt gtaaaatcct accataaaat   6502

gctaaaaata tgcattgttt caaataaaac caagaaatgc agcattatat a            6553


<210> SEQ ID NO 8
<211> LENGTH: 1303
<212> TYPE: PRT
<213> ORGANISM: Bos taurus

<400> SEQUENCE: 8

Met Asp Phe Thr Ala Gln Pro Lys Pro Ala Thr Ala Leu Cys Gly Val
1               5                   10                  15

Val Ser Ala Asp Gly Lys Ile Ala Tyr Pro Pro Gly Val Lys Glu Ile
            20                  25                  30

Thr Asp Lys Ile Thr Thr Asp Glu Met Ile Lys Arg Leu Lys Met Val
        35                  40                  45

Val Lys Thr Phe Met Asp Met Asp Gln Asp Ser Glu Asp Glu Lys Gln
    50                  55                  60

Gln Tyr Leu Pro Leu Ala Leu His Leu Ala Ser Glu Phe Phe Leu Arg
65                  70                  75                  80

Asn Pro Asn Lys Asp Val Arg Leu Leu Val Ala Cys Cys Leu Ala Asp
                85                  90                  95

Ile Phe Arg Ile Tyr Ala Pro Glu Ala Pro Tyr Thr Ser His Asp Lys
            100                 105                 110

Leu Lys Asp Ile Phe Leu Phe Ile Thr Arg Gln Leu Lys Gly Leu Glu
        115                 120                 125

Asp Thr Lys Ser Pro Gln Phe Asn Arg Tyr Phe Tyr Leu Leu Glu Asn
    130                 135                 140

Leu Ala Trp Val Lys Ser Tyr Asn Ile Cys Phe Glu Leu Glu Asp Cys
145                 150                 155                 160

Asn Glu Ile Phe Ile Gln Leu Phe Arg Thr Leu Phe Ser Val Ile Asn
                165                 170                 175

Asn Ser His Asn Lys Lys Val Gln Met His Met Leu Asp Leu Met Ser
            180                 185                 190

Ser Ile Ile Met Glu Gly Asp Gly Val Thr Gln Glu Leu Leu Asp Ser
        195                 200                 205

Ile Leu Ile Asn Leu Ile Pro Ala His Lys Asn Leu Asn Lys Gln Ser
    210                 215                 220

Phe Asp Leu Ala Lys Val Leu Leu Lys Arg Thr Val Gln Thr Ile Glu
225                 230                 235                 240

Ala Cys Ile Ala Asn Phe Phe Asn Gln Val Leu Val Leu Gly Arg Ser
                245                 250                 255

Ser Val Ser Asp Leu Ser Glu His Val Phe Asp Leu Ile Gln Glu Leu
            260                 265                 270

Phe Ala Ile Asp Pro His Leu Leu Leu Ser Val Met Pro Gln Leu Glu
        275                 280                 285

Phe Lys Leu Lys Ser Asn Asp Gly Glu Glu Arg Leu Ala Val Val Arg
    290                 295                 300

Leu Leu Ala Lys Leu Phe Gly Ser Lys Asp Ser Asp Leu Ala Thr Gln
305                 310                 315                 320
```

```
Asn Arg Pro Leu Trp Gln Cys Phe Leu Gly Arg Phe Asn Asp Ile His
                325                 330                 335

Val Pro Val Arg Leu Glu Ser Val Lys Phe Ala Ser His Cys Leu Met
            340                 345                 350

Asn His Pro Asp Leu Ala Lys Asp Leu Thr Gly Phe Thr Leu Ala Leu
        355                 360                 365

Phe Gln Val Ser Asn Ser His Gly Leu Trp Arg Val Arg Lys Glu Ala
    370                 375                 380

Met Met Gly Leu Ala Gln Leu Tyr Lys Lys Tyr Cys Leu His Gly Glu
385                 390                 395                 400

Ala Gly Lys Glu Ala Ala Glu Lys Val Ser Trp Ile Lys Asp Lys Leu
                405                 410                 415

Leu His Ile Tyr Tyr Gln Asn Ser Ile Asp Asp Lys Leu Leu Val Glu
            420                 425                 430

Lys Ile Phe Ala Gln Tyr Leu Val Pro His Asn Leu Glu Thr Glu Glu
        435                 440                 445

Arg Met Lys Cys Leu Tyr Tyr Leu Tyr Ala Ser Leu Asp Pro Asn Ala
    450                 455                 460

Val Lys Ala Leu Asn Glu Met Trp Lys Cys Gln Asn Met Leu Arg Ser
465                 470                 475                 480

His Val Arg Glu Leu Leu Asp Leu His Lys Gln Pro Thr Ser Glu Ala
                485                 490                 495

Asn Cys Ser Ala Met Phe Gly Lys Leu Met Thr Ile Ala Lys Asn Leu
            500                 505                 510

Pro Asp Pro Gly Lys Ala Gln Asp Phe Val Lys Lys Phe Asn Gln Val
        515                 520                 525

Leu Gly Asp Asp Glu Lys Leu Arg Ser Gln Leu Glu Leu Leu Ile Ser
    530                 535                 540

Pro Thr Cys Ser Cys Lys Gln Ala Asp Val Cys Val Arg Glu Ile Ala
545                 550                 555                 560

Arg Lys Leu Ala Asn Pro Lys Gln Pro Thr Asn Pro Phe Leu Glu Met
                565                 570                 575

Val Lys Phe Leu Leu Glu Arg Ile Ala Pro Val His Ile Asp Ser Glu
            580                 585                 590

Ala Ile Ser Ala Leu Val Lys Leu Met Asn Lys Ser Ile Glu Gly Thr
        595                 600                 605

Ala Asp Asp Glu Glu Glu Gly Val Ser Pro Asp Thr Ala Ile Arg Ser
    610                 615                 620

Gly Leu Glu Leu Leu Lys Val Leu Ser Phe Thr His Pro Thr Ser Phe
625                 630                 635                 640

His Ser Ala Glu Thr Tyr Glu Ser Leu Leu Gln Cys Leu Arg Met Glu
                645                 650                 655

Asp Asp Lys Val Ala Glu Ala Ala Ile Gln Ile Phe Arg Asn Thr Gly
            660                 665                 670

His Lys Ile Glu Thr Asp Leu Pro Gln Ile Arg Ser Thr Leu Ile Pro
        675                 680                 685

Ile Leu His Gln Lys Ala Lys Arg Gly Thr Pro His Gln Ala Lys Gln
    690                 695                 700

Ala Val His Cys Ile His Ala Ile Phe Thr Asn Lys Glu Val Gln Leu
705                 710                 715                 720

Ala Gln Ile Phe Glu Pro Leu Ser Arg Ser Leu Asn Ala Asp Val Pro
                725                 730                 735
```

```
Glu Gln Leu Ile Thr Pro Leu Val Ser Leu Gly His Ile Ser Met Leu
            740                 745                 750

Ala Pro Asp Gln Phe Ala Ser Pro Met Lys Ser Val Val Ala Asn Phe
        755                 760                 765

Ile Val Lys Asp Leu Leu Met Asn Asp Arg Ser Thr Gly Glu Lys Asn
    770                 775                 780

Gly Lys Leu Trp Ser Pro Asp Glu Glu Val Ser Pro Glu Val Leu Ala
785                 790                 795                 800

Lys Val Gln Ala Ile Lys Leu Leu Val Arg Trp Leu Leu Gly Met Lys
                805                 810                 815

Asn Asn Gln Ser Lys Ser Ala Asn Ser Thr Leu Arg Leu Leu Ser Ala
            820                 825                 830

Met Leu Val Ser Glu Gly Asp Leu Thr Glu Gln Lys Arg Ile Ser Lys
        835                 840                 845

Ser Asp Met Ser Arg Leu Arg Leu Ala Ala Gly Ser Ala Ile Met Lys
    850                 855                 860

Leu Ala Gln Glu Pro Cys Tyr His Glu Ile Ile Thr Pro Glu Gln Phe
865                 870                 875                 880

Gln Leu Cys Ala Leu Val Ile Asn Asp Glu Cys Tyr Gln Val Arg Gln
                885                 890                 895

Ile Phe Ala Gln Lys Leu His Lys Ala Leu Val Lys Leu Leu Leu Pro
            900                 905                 910

Leu Glu Tyr Met Ala Ile Phe Ala Leu Cys Ala Lys Asp Pro Val Lys
        915                 920                 925

Glu Arg Arg Ala His Ala Arg Gln Cys Leu Leu Lys Asn Ile Ser Ile
    930                 935                 940

Arg Arg Glu Tyr Ile Lys Gln Asn Pro Met Ala Thr Glu Lys Leu Leu
945                 950                 955                 960

Ser Leu Leu Pro Glu Tyr Val Val Pro Tyr Met Ile His Leu Leu Ala
                965                 970                 975

His Asp Pro Asp Phe Thr Arg Ser Gln Asp Val Asp Gln Leu Arg Asp
            980                 985                 990

Ile Lys Glu Cys Leu Trp Phe Met  Leu Glu Val Leu Met  Thr Lys Asn
        995                 1000                 1005

Glu Asn  Asn Ser His Ala Phe  Met Lys Lys Met Ala  Glu Asn Ile
    1010                 1015                 1020

Lys Leu  Thr Lys Asp Ala Gln  Ser Pro Asp Glu Ser  Lys Thr Asn
    1025                 1030                 1035

Glu Lys  Leu Tyr Thr Val Cys  Asp Val Ala Leu Cys  Val Ile Asn
    1040                 1045                 1050

Ser Lys  Ser Ala Leu Cys Asn  Ala Glu Ser Pro Lys  Asp Pro Val
    1055                 1060                 1065

Leu Pro  Val Lys Phe Phe Thr  Gln Pro Glu Lys Asp  Phe Cys Asn
    1070                 1075                 1080

Asp Lys  Ser Tyr Ile Ser Glu  Glu Thr Arg Val Leu  Leu Leu Thr
    1085                 1090                 1095

Gly Lys  Pro Lys Pro Ala Gly  Val Leu Gly Ala Val  Asn Lys Pro
    1100                 1105                 1110

Leu Ser  Ala Thr Gly Arg Lys  Pro Tyr Val Arg Ser  Thr Gly Ala
    1115                 1120                 1125

Glu Thr  Gly Ser Asn Ile Asn  Val Asn Ser Glu Leu  Asn Pro Ser
    1130                 1135                 1140

Thr Gly  Asn Arg Pro Arg Glu  Gln Ser Ser Glu Ala  Ala Glu Thr
```

```
    1145                1150                1155

Gly Val  Ser Glu Asn Glu Glu  Asn Pro Val Arg Ile  Ile Ser Val
    1160                1165                1170

Thr Pro  Val Lys Asn Ile Asp  Pro Val Lys Asn Lys  Glu Ile Asn
    1175                1180                1185

Ser Asp  Gln Ser Ala Gln Gly  Asn Ile Ser Ser Asp  Arg Gly Lys
    1190                1195                1200

Lys Arg  Thr Val Thr Ala Ala  Gly Ala Glu Asn Ile  Gln Gln Lys
    1205                1210                1215

Thr Asp  Glu Lys Ala Asp Glu  Ser Gly Pro Pro Ala  Pro Ser Lys
    1220                1225                1230

Pro Arg  Arg Gly Arg Arg Pro  Lys Ser Glu Ser Gln  Gly Asn Ala
    1235                1240                1245

Thr Lys  Asn Asp Asp Ile Asn  Lys Pro Leu Ser Lys  Gly Arg Lys
    1250                1255                1260

Arg Ala  Ala Val Ser Gln Glu  Ser Pro Gly Gly Leu  Glu Ala Gly
    1265                1270                1275

Asn Ala  Lys Ala Pro Lys Leu  Gln Asp Thr Ala Lys  Lys Ala Ala
    1280                1285                1290

Pro Thr  Glu Arg Gln Ile Asp  Leu Gln Arg
    1295                1300


<210> SEQ ID NO 9
<211> LENGTH: 6680
<212> TYPE: DNA
<213> ORGANISM: Equus caballus
<220> FEATURE:
<221> NAME/KEY: CDS
<222> LOCATION: (1)..(4014)
<223> OTHER INFORMATION:

<400> SEQUENCE: 9

atg gac ttc acc gcg cag ccc aag cct gcc act gcc ctc tgt ggc gtc       48
Met Asp Phe Thr Ala Gln Pro Lys Pro Ala Thr Ala Leu Cys Gly Val
1               5                   10                  15

gtg agt gcg gac ggg aag atc gct tac cct ccg ggg gta aag gag atc       96
Val Ser Ala Asp Gly Lys Ile Ala Tyr Pro Pro Gly Val Lys Glu Ile
            20                  25                  30

acc gac aag atc acc act gac gaa atg atc aaa cga ctg aag atg gta      144
Thr Asp Lys Ile Thr Thr Asp Glu Met Ile Lys Arg Leu Lys Met Val
        35                  40                  45

gta aaa act ttt atg gat atg gac cag gac tca gaa gat gaa aaa cag      192
Val Lys Thr Phe Met Asp Met Asp Gln Asp Ser Glu Asp Glu Lys Gln
    50                  55                  60

cag tat ctc cca ctc gcc ttg cat ctt gca tct gaa ttt ttc ctc agg      240
Gln Tyr Leu Pro Leu Ala Leu His Leu Ala Ser Glu Phe Phe Leu Arg
65                  70                  75                  80

aat ccc aat aaa gat gtg cgt ctc ctt gta gca tgt tgt ttg gct gac      288
Asn Pro Asn Lys Asp Val Arg Leu Leu Val Ala Cys Cys Leu Ala Asp
                85                  90                  95

atc ttt cga atc tat gcc cca gaa gct cca tat act tcc cat gat aaa      336
Ile Phe Arg Ile Tyr Ala Pro Glu Ala Pro Tyr Thr Ser His Asp Lys
            100                 105                 110

ctt aag gac ata ttt ttg ttt att acc aga caa tta aaa ggt ttg gag      384
Leu Lys Asp Ile Phe Leu Phe Ile Thr Arg Gln Leu Lys Gly Leu Glu
        115                 120                 125

gat aca aag agt ccg cag ttt aat aga tac ttt tat tta tta gag aat      432
Asp Thr Lys Ser Pro Gln Phe Asn Arg Tyr Phe Tyr Leu Leu Glu Asn
    130                 135                 140
```

```
tta gct tgg gtt aaa tca tat aac atc tgc ttt gaa ttg gaa gat tgc      480
Leu Ala Trp Val Lys Ser Tyr Asn Ile Cys Phe Glu Leu Glu Asp Cys
145                 150                 155                 160

aat gaa att ttt att cag ctt ttt agg act ctc ttc tca gtg atc aac      528
Asn Glu Ile Phe Ile Gln Leu Phe Arg Thr Leu Phe Ser Val Ile Asn
                165                 170                 175

aat agc cac aat aag aag gta caa atg cac atg cta gac ttg atg agt      576
Asn Ser His Asn Lys Lys Val Gln Met His Met Leu Asp Leu Met Ser
            180                 185                 190

tct atc atc atg gaa ggt gat gga gtt act caa gaa tta ttg gac tcc      624
Ser Ile Ile Met Glu Gly Asp Gly Val Thr Gln Glu Leu Leu Asp Ser
        195                 200                 205

att ctt att aac ctc att cct gca cat aag aac tta aac aaa cag tcc      672
Ile Leu Ile Asn Leu Ile Pro Ala His Lys Asn Leu Asn Lys Gln Ser
    210                 215                 220

ttt gac ctc gct aaa gtg ctg ttg aaa agg aca gtc cag act att gag      720
Phe Asp Leu Ala Lys Val Leu Leu Lys Arg Thr Val Gln Thr Ile Glu
225                 230                 235                 240

gca tgc att gct aat ttt ttc aat caa gtc ctg gtg ctg gga aga tca      768
Ala Cys Ile Ala Asn Phe Phe Asn Gln Val Leu Val Leu Gly Arg Ser
                245                 250                 255

tca gta agt gat tta tca gaa cat gta ttt gat ctg att cag gaa ctt      816
Ser Val Ser Asp Leu Ser Glu His Val Phe Asp Leu Ile Gln Glu Leu
            260                 265                 270

ttt gct ata gat cct cat ttg tta tta tct gtc atg cca cag ctt gaa      864
Phe Ala Ile Asp Pro His Leu Leu Leu Ser Val Met Pro Gln Leu Glu
        275                 280                 285

ttc aaa ctg aag agc aat gat gga gaa gag cga cta gct gtt gtt cga      912
Phe Lys Leu Lys Ser Asn Asp Gly Glu Glu Arg Leu Ala Val Val Arg
    290                 295                 300

ctt tta gct aaa ttg ttt ggt tct aaa gat tcc gat ttg gca aca cag      960
Leu Leu Ala Lys Leu Phe Gly Ser Lys Asp Ser Asp Leu Ala Thr Gln
305                 310                 315                 320

aat cgt cct ctt tgg cag tgt ttt ctc gga cga ttt aat gac att cac     1008
Asn Arg Pro Leu Trp Gln Cys Phe Leu Gly Arg Phe Asn Asp Ile His
                325                 330                 335

gtt cct gtg aga tta gaa agt gtg aaa ttt gcc agt cac tgt tta atg     1056
Val Pro Val Arg Leu Glu Ser Val Lys Phe Ala Ser His Cys Leu Met
            340                 345                 350

aac cac cca gat tta gca aag gac ctc aca gaa tat ttg aaa gtt aga     1104
Asn His Pro Asp Leu Ala Lys Asp Leu Thr Glu Tyr Leu Lys Val Arg
        355                 360                 365

tca cat gat cca gaa gaa gcc att cgt cat gat gtc att gtt act ata     1152
Ser His Asp Pro Glu Glu Ala Ile Arg His Asp Val Ile Val Thr Ile
    370                 375                 380

ata aca gct gcc aaa aga gac ctt gcc tta gta aat gat cag ctg ctt     1200
Ile Thr Ala Ala Lys Arg Asp Leu Ala Leu Val Asn Asp Gln Leu Leu
385                 390                 395                 400

ggc ttt gta agg gaa aga aca ctg gat aaa cgg tgg cga gta aga aaa     1248
Gly Phe Val Arg Glu Arg Thr Leu Asp Lys Arg Trp Arg Val Arg Lys
                405                 410                 415

gaa gct atg atg ggt ctg gct cag ctt tat aag aaa tac tgt ctt cat     1296
Glu Ala Met Met Gly Leu Ala Gln Leu Tyr Lys Lys Tyr Cys Leu His
            420                 425                 430

ggt gaa gca gga aag gaa gct gca gag aaa gtc agt tgg ata aag gac     1344
Gly Glu Ala Gly Lys Glu Ala Ala Glu Lys Val Ser Trp Ile Lys Asp
        435                 440                 445

aaa ctt ttg cat att tat tat cag aat agc atc gat gac aaa ctg ttg     1392
Lys Leu Leu His Ile Tyr Tyr Gln Asn Ser Ile Asp Asp Lys Leu Leu
```

```
    450                 455                 460

gta gag aaa atc ttt gct cag tat ctt gtt ccc cac aac ctg gaa aca      1440
Val Glu Lys Ile Phe Ala Gln Tyr Leu Val Pro His Asn Leu Glu Thr
465                 470                 475                 480

gaa gag aga atg aaa tgc tta tat tat tta tat gct agt ttg gat cca      1488
Glu Glu Arg Met Lys Cys Leu Tyr Tyr Leu Tyr Ala Ser Leu Asp Pro
                485                 490                 495

aat gct gtc aaa gct ctc aat gaa atg tgg aag tgt cag aac atg ctt      1536
Asn Ala Val Lys Ala Leu Asn Glu Met Trp Lys Cys Gln Asn Met Leu
            500                 505                 510

aga agt cat gta cga gaa tta ctg gat ttg cat aag cag cct aca tca      1584
Arg Ser His Val Arg Glu Leu Leu Asp Leu His Lys Gln Pro Thr Ser
        515                 520                 525

gag gct aac tgt tct gct atg ttt gga aaa ctg atg acc ata gca aag      1632
Glu Ala Asn Cys Ser Ala Met Phe Gly Lys Leu Met Thr Ile Ala Lys
    530                 535                 540

aat ttg cct gac cct ggg aaa gca caa gat ttt gtg aag aaa ttt aac      1680
Asn Leu Pro Asp Pro Gly Lys Ala Gln Asp Phe Val Lys Lys Phe Asn
545                 550                 555                 560

cag gtt ctc ggt gat gat gag aaa cta cgg tct cag ttg gag tta tta      1728
Gln Val Leu Gly Asp Asp Glu Lys Leu Arg Ser Gln Leu Glu Leu Leu
                565                 570                 575

atc agc cca acc tgt tca tgc aaa cag gca gat gtt tgt gtg aga gaa      1776
Ile Ser Pro Thr Cys Ser Cys Lys Gln Ala Asp Val Cys Val Arg Glu
            580                 585                 590

ata gct cgg aaa ctt gca aat cct aag caa cca aca aat cct ttt cta      1824
Ile Ala Arg Lys Leu Ala Asn Pro Lys Gln Pro Thr Asn Pro Phe Leu
        595                 600                 605

gag atg gtc aaa ttt ctg ttg gaa aga att gca cct gtg cac att gat      1872
Glu Met Val Lys Phe Leu Leu Glu Arg Ile Ala Pro Val His Ile Asp
    610                 615                 620

tcg gaa gcc ata agt gca ctg gta aaa ttg atg aat aaa tcc ata gag      1920
Ser Glu Ala Ile Ser Ala Leu Val Lys Leu Met Asn Lys Ser Ile Glu
625                 630                 635                 640

ggg aca gca gat gat gaa gag gag ggt gta agt cca gat aca gcg att      1968
Gly Thr Ala Asp Asp Glu Glu Glu Gly Val Ser Pro Asp Thr Ala Ile
                645                 650                 655

cgt tca gga ctt gaa ctt ctt aag gtt ctg tct ttc aca cat cct acc      2016
Arg Ser Gly Leu Glu Leu Leu Lys Val Leu Ser Phe Thr His Pro Thr
            660                 665                 670

tcg ttc cac tct gca gag acg tat gag tcc ctg tta cag tgc ctc aga      2064
Ser Phe His Ser Ala Glu Thr Tyr Glu Ser Leu Leu Gln Cys Leu Arg
        675                 680                 685

atg gaa gat gac aag gta gca gaa gct gct ata caa att ttt aga aat      2112
Met Glu Asp Asp Lys Val Ala Glu Ala Ala Ile Gln Ile Phe Arg Asn
    690                 695                 700

aca ggc cac aaa att gaa aca gac ctg ccc cag ata cga tcg acc tta      2160
Thr Gly His Lys Ile Glu Thr Asp Leu Pro Gln Ile Arg Ser Thr Leu
705                 710                 715                 720

att ccc att tta cat cag aaa gca aag aga ggt act cca cac caa gca      2208
Ile Pro Ile Leu His Gln Lys Ala Lys Arg Gly Thr Pro His Gln Ala
                725                 730                 735

aaa cag gct gtt cac tgt ata cat gcc ata ttc aca aat aaa gaa gtc      2256
Lys Gln Ala Val His Cys Ile His Ala Ile Phe Thr Asn Lys Glu Val
            740                 745                 750

cag ctt gca cag att ttt gag cca ctc agt agg agt ctg aat gct gat      2304
Gln Leu Ala Gln Ile Phe Glu Pro Leu Ser Arg Ser Leu Asn Ala Asp
        755                 760                 765

gta cca gaa caa ctt ata act cca tta gtt tca ttg ggc cac ata tct      2352
```

```
Val Pro Glu Gln Leu Ile Thr Pro Leu Val Ser Leu Gly His Ile Ser
    770                 775                 780

atg tta gca cca gat cag ttt gct tct cca atg aaa tct gta gta gca      2400
Met Leu Ala Pro Asp Gln Phe Ala Ser Pro Met Lys Ser Val Val Ala
785                 790                 795                 800

aat ttt att gtg aaa gat ctc cta atg aat gac agg tca aca ggt gag      2448
Asn Phe Ile Val Lys Asp Leu Leu Met Asn Asp Arg Ser Thr Gly Glu
                805                 810                 815

aag aat gga aaa tta tgg tct cca gat gaa gaa gtt tct cct gaa gta      2496
Lys Asn Gly Lys Leu Trp Ser Pro Asp Glu Glu Val Ser Pro Glu Val
            820                 825                 830

tta gca aag gta cag gca att aaa ctt ctg gta agg tgg ctg ttg ggt      2544
Leu Ala Lys Val Gln Ala Ile Lys Leu Leu Val Arg Trp Leu Leu Gly
        835                 840                 845

atg aaa aac aac cag tct aaa tct gcc aat tca act ctt cgg tta tta      2592
Met Lys Asn Asn Gln Ser Lys Ser Ala Asn Ser Thr Leu Arg Leu Leu
    850                 855                 860

tca gcg atg ttg gtt agt gag ggt gac ctg aca gag caa aag agg atc      2640
Ser Ala Met Leu Val Ser Glu Gly Asp Leu Thr Glu Gln Lys Arg Ile
865                 870                 875                 880

agt aaa tct gat atg tct cgc ttg cga tta gct gct ggt agt gcc ata      2688
Ser Lys Ser Asp Met Ser Arg Leu Arg Leu Ala Ala Gly Ser Ala Ile
                885                 890                 895

atg aag ctt gct cag gaa cct tgt tac cat gaa att ata acc cca gaa      2736
Met Lys Leu Ala Gln Glu Pro Cys Tyr His Glu Ile Ile Thr Pro Glu
            900                 905                 910

cag ttt cag ctc tgt gca ctt gtt att aat gat gag tgc tac caa gta      2784
Gln Phe Gln Leu Cys Ala Leu Val Ile Asn Asp Glu Cys Tyr Gln Val
        915                 920                 925

agg cag ata ttt gct cag aag ctg cat aag gcg ctt gta aag ttg ctg      2832
Arg Gln Ile Phe Ala Gln Lys Leu His Lys Ala Leu Val Lys Leu Leu
    930                 935                 940

ctc ccg ttg gag tat atg gcg atc ttt gcc ttg tgt gcc aaa gat cct      2880
Leu Pro Leu Glu Tyr Met Ala Ile Phe Ala Leu Cys Ala Lys Asp Pro
945                 950                 955                 960

gtg aag gaa aga aga gca cat gca cgg cag tgt tta cta aaa aat atc      2928
Val Lys Glu Arg Arg Ala His Ala Arg Gln Cys Leu Leu Lys Asn Ile
                965                 970                 975

agt ata cgc agg gag tac att aaa cag aac ccc atg gct act gag aaa      2976
Ser Ile Arg Arg Glu Tyr Ile Lys Gln Asn Pro Met Ala Thr Glu Lys
            980                 985                 990

tta tta tca ctg ttg cct gaa tat  gta gtt cca tat atg  att cac cta    3024
Leu Leu Ser Leu Leu Pro Glu Tyr  Val Val Pro Tyr Met  Ile His Leu
        995                 1000                1005

tta gcc  cat gat cca gat ttt  aca aga tca caa gat  gtt gat caa      3069
Leu Ala  His Asp Pro Asp Phe  Thr Arg Ser Gln Asp  Val Asp Gln
    1010                1015                1020

ctt cgt  gat att aaa gag tgc  cta tgg ttc atg ctt  gaa gtt tta      3114
Leu Arg  Asp Ile Lys Glu Cys  Leu Trp Phe Met Leu  Glu Val Leu
    1025                1030                1035

atg aca  aag aat gaa aac aat  agc cat gcc ttt atg  aag aag atg      3159
Met Thr  Lys Asn Glu Asn Asn  Ser His Ala Phe Met  Lys Lys Met
    1040                1045                1050

gca gaa  aac atc aag tta aca  aaa gat gcc cag tct  cca gat gaa      3204
Ala Glu  Asn Ile Lys Leu Thr  Lys Asp Ala Gln Ser  Pro Asp Glu
    1055                1060                1065

tcc aag  aca aat gaa aaa ctt  tat aca gtg tgt gat  gtg gct ctg      3249
Ser Lys  Thr Asn Glu Lys Leu  Tyr Thr Val Cys Asp  Val Ala Leu
    1070                1075                1080
```

```
tgt gtt ata aac agt aaa agt gct ttg tgc aat gca gat tca cca      3294
Cys Val Ile Asn Ser Lys Ser Ala Leu Cys Asn Ala Asp Ser Pro
    1085                1090                1095

aag gat cca gtc ctt cca atg aaa ttt ttt aca caa cct gaa aag      3339
Lys Asp Pro Val Leu Pro Met Lys Phe Phe Thr Gln Pro Glu Lys
    1100                1105                1110

gac ttc tgt aat gac aag agt tat att tca gaa gag aca aga gta      3384
Asp Phe Cys Asn Asp Lys Ser Tyr Ile Ser Glu Glu Thr Arg Val
    1115                1120                1125

ctt ctg tta aca gga aag cca aaa cct gct gga gta ctt ggt gca      3429
Leu Leu Leu Thr Gly Lys Pro Lys Pro Ala Gly Val Leu Gly Ala
    1130                1135                1140

gta aac aag cct tta tcg gca acg gga agg aaa cca tat gtt aga      3474
Val Asn Lys Pro Leu Ser Ala Thr Gly Arg Lys Pro Tyr Val Arg
    1145                1150                1155

agc act gga act gag act gga agc act att aat gtc aat tca gag      3519
Ser Thr Gly Thr Glu Thr Gly Ser Thr Ile Asn Val Asn Ser Glu
    1160                1165                1170

ctg aac cct tca act gga agt cga tca aga gaa cag agt tca gag      3564
Leu Asn Pro Ser Thr Gly Ser Arg Ser Arg Glu Gln Ser Ser Glu
    1175                1180                1185

gca gca gaa act gga gtt agt gaa aat gaa gag aac cct gtg aga      3609
Ala Ala Glu Thr Gly Val Ser Glu Asn Glu Glu Asn Pro Val Arg
    1190                1195                1200

att att tct gtc acg cct gta aag aat att gac ccg gta aag aat      3654
Ile Ile Ser Val Thr Pro Val Lys Asn Ile Asp Pro Val Lys Asn
    1205                1210                1215

aag gag att aat tct gat cag gct acc cag ggc aac atc agc agt      3699
Lys Glu Ile Asn Ser Asp Gln Ala Thr Gln Gly Asn Ile Ser Ser
    1220                1225                1230

gac cga gga aag aaa aga aca gta aca gca gct ggt aca gag aat      3744
Asp Arg Gly Lys Lys Arg Thr Val Thr Ala Ala Gly Thr Glu Asn
    1235                1240                1245

atc caa caa aaa aca gat gag aaa gtg gat gaa tca gga cca cct      3789
Ile Gln Gln Lys Thr Asp Glu Lys Val Asp Glu Ser Gly Pro Pro
    1250                1255                1260

gcc cct tca aaa ccc agg aga gga cgt cga ccc aag tct gaa tct      3834
Ala Pro Ser Lys Pro Arg Arg Gly Arg Arg Pro Lys Ser Glu Ser
    1265                1270                1275

cag ggc aat gca acc aaa aat gat gat ata aat aaa cct ctt agc      3879
Gln Gly Asn Ala Thr Lys Asn Asp Asp Ile Asn Lys Pro Leu Ser
    1280                1285                1290

aag gga aga aag aga gcc gcg gtc agt cag gaa agc cct ggg ggt      3924
Lys Gly Arg Lys Arg Ala Ala Val Ser Gln Glu Ser Pro Gly Gly
    1295                1300                1305

ttg gaa gca ggt aat gcc aaa gca ccc aaa ctg caa gac ata gcc      3969
Leu Glu Ala Gly Asn Ala Lys Ala Pro Lys Leu Gln Asp Ile Ala
    1310                1315                1320

aaa aag gca gca cca gca gag aga cag att gac cta caa agg taa      4014
Lys Lys Ala Ala Pro Ala Glu Arg Gln Ile Asp Leu Gln Arg
    1325                1330                1335

taaaactcgt ttgcaaaggg agaaaatgaa ggccaaacag aagcaggctc cagcttctgt   4074

aaaacttgga ttcaaaatgt ccctgaagag aaatgaagtt aagttcagaa cacacacttt   4134

ctgccttgaa aactgaaaga aaccattact ttcttttcac atgaccacaa gtctttgatg   4194

gaaatgtaca gcagaaactc ttgagagagg ctaaaagcaa ctctattcta cccttccccc   4254

cagacttttc ttatgaaaag tcaataatta agcaaattgc ttaacacttg gttccagttc   4314

ctgcatatct ggagtttaaa ggcatagtac accattaatt tccatgctgc agtttttatt   4374
```

```
ttaaagaaag taacaggatg tccttacact gacactgaaa attcatcaat tttagagcca   4434
ggaattcccg ttgttacaca agaaaaaaat agaagtctac tgaattaatt ttttagaaga   4494
aaaaagatca gattaaatat ttctttgttt ttccttttgg aaacttttat gtataattct   4554
ttctgcctgc ctacttttct gcaaaaatga gatgtacaga tttcagttcc ctgctatgaa   4614
aagtgatgtg gtggcaattt tataaatgtt gctttctgat ttttatcaga gtgagaaaat   4674
aattaaaatt attattgatt tcatatcact tcatattttg atttcccctc cattttagtt   4734
taatataatt tgcaataaat gtacatattg ttgtttgttt cataaagcat atcactttaa   4794
agtggttttt actcctgtga ttatgttggg atatttggaa ttttaaagga gtaaagactg   4854
tccagcattt ggttttataa tgtttgtcac cagattttta ttattgatgt aaaaaaacaa   4914
agtcaatttt ttaaaatagt tggactttgg cagctttgta aggaaagttg gaagtgttta   4974
ggattgctat caatttcagc attgtgctat tgggaaataa gtgttttgct tttgtctgcc   5034
gatctgggct cagtttttat gtttatttta gaagacaact gttgcatcaa tatattgctt   5094
cttggcattg ttcagcatag gtaatgtgtg cacttttgtg tacacatgct catatttaag   5154
ttttcgcata aaataaatgc ttctagatgt catatggtag tctttttttaa tctttttatc   5214
atatgttgtg aatttttttt atgtgaaagg gctaatgtca ttaaacaaag aacatgatta   5274
cagtcaactc tccattatct atataaaata gtgactgtgc ctcaggtttt gaattttgca   5334
gtaatcataa acttaaaata atgaaggcat actgcaggag ctaattcagg aggaacttga   5394
aatttgtcct ttctcacgct cagagttatg gcctgccccc attctccatt gtaggctctt   5454
tcccaaagcc ctagctgggt gttcttactc cattcccaca cacatgccta gcctgggtta   5514
gaggatggaa acgacgcttg cattataact tggtcttcat aggctgtagt ctacatggga   5574
tgtacaaaca gtgaatgtga gctgtgacaa aaaaggatgg ttatgttaat gcgaaaattt   5634
gctggtagta aatgtcactt atgttctcat agataatcaa gagttggctg tatattgact   5694
gagtgaaaaa tgggtagttc ttttaaatat gcatatacac acatttaggt atcatgatga   5754
ttagggaaca atggatacca gtgacagaaa acagtatctt ttgaaagggc agaaacagcc   5814
ctactcttcc ttattgcctc ttcctaaccc tttagaagga aagtataaaa aaaacattgc   5874
ctccaacatg ctgaagaaga atatctatgc ataagcatct gagaagtccc tcaagcaatc   5934
agtgggcacg ttctatttag aaagatttta aagttccctt agcatcagac agcttggttc   5994
ttaaggccac caattggtca ccaataagaa gcacacctgt agggaacttc tttctctctt   6054
aactcctttt gataattact cagcaccaca gctgagagat tacatagtgt tcagtcatat   6114
tcaacataat gtagcagaac catttgcatc agtttatggc tgctgagatt attgcaggag   6174
aggagttagc tgaaaggatc tggtccgcat acacatgtaa ctggcccact catgatttta   6234
taacatgtct ggcactaagg gaagggagaa taggatgata ggaaagattg agctgatgtg   6294
gagggacttg tttaagggaa atttgtcatt tttcctttga aaaaggaaaa agtaaaatcc   6354
cttaggaatt tggtattcgt atctcagaga aatacaacac aaagtgcaga cttatatttg   6414
agaattaatg ttaacccttt gtgtctagtt tgaagcttct tgtatttgtc taaaactaca   6474
agccagaatt ttgtatctcc tttgataaaa agtgtgtata atgtaaagta gttttgcata   6534
ttgtgctgca catgggctga atttttaaaa tttttttaaa gacttgaagc agaaccttgt   6594
aatttgtgta aatgacaagt gtaaaatcct accataaaat gctaaaaata tgcattgttt   6654
caaataaaac caagaaatgc agcatt                                        6680
```

<210> SEQ ID NO 10
<211> LENGTH: 1337
<212> TYPE: PRT
<213> ORGANISM: Equus caballus

<400> SEQUENCE: 10

```
Met Asp Phe Thr Ala Gln Pro Lys Pro Ala Thr Ala Leu Cys Gly Val
1               5                   10                  15

Val Ser Ala Asp Gly Lys Ile Ala Tyr Pro Pro Gly Val Lys Glu Ile
            20                  25                  30

Thr Asp Lys Ile Thr Thr Asp Glu Met Ile Lys Arg Leu Lys Met Val
        35                  40                  45

Val Lys Thr Phe Met Asp Met Asp Gln Asp Ser Glu Asp Glu Lys Gln
    50                  55                  60

Gln Tyr Leu Pro Leu Ala Leu His Leu Ala Ser Glu Phe Phe Leu Arg
65                  70                  75                  80

Asn Pro Asn Lys Asp Val Arg Leu Leu Val Ala Cys Cys Leu Ala Asp
                85                  90                  95

Ile Phe Arg Ile Tyr Ala Pro Glu Ala Pro Tyr Thr Ser His Asp Lys
            100                 105                 110

Leu Lys Asp Ile Phe Leu Phe Ile Thr Arg Gln Leu Lys Gly Leu Glu
        115                 120                 125

Asp Thr Lys Ser Pro Gln Phe Asn Arg Tyr Phe Tyr Leu Leu Glu Asn
    130                 135                 140

Leu Ala Trp Val Lys Ser Tyr Asn Ile Cys Phe Glu Leu Glu Asp Cys
145                 150                 155                 160

Asn Glu Ile Phe Ile Gln Leu Phe Arg Thr Leu Phe Ser Val Ile Asn
                165                 170                 175

Asn Ser His Asn Lys Lys Val Gln Met His Met Leu Asp Leu Met Ser
            180                 185                 190

Ser Ile Ile Met Glu Gly Asp Gly Val Thr Gln Glu Leu Leu Asp Ser
        195                 200                 205

Ile Leu Ile Asn Leu Ile Pro Ala His Lys Asn Leu Asn Lys Gln Ser
    210                 215                 220

Phe Asp Leu Ala Lys Val Leu Leu Lys Arg Thr Val Gln Thr Ile Glu
225                 230                 235                 240

Ala Cys Ile Ala Asn Phe Phe Asn Gln Val Leu Val Leu Gly Arg Ser
                245                 250                 255

Ser Val Ser Asp Leu Ser Glu His Val Phe Asp Leu Ile Gln Glu Leu
            260                 265                 270

Phe Ala Ile Asp Pro His Leu Leu Leu Ser Val Met Pro Gln Leu Glu
        275                 280                 285

Phe Lys Leu Lys Ser Asn Asp Gly Glu Glu Arg Leu Ala Val Val Arg
    290                 295                 300

Leu Leu Ala Lys Leu Phe Gly Ser Lys Asp Ser Asp Leu Ala Thr Gln
305                 310                 315                 320

Asn Arg Pro Leu Trp Gln Cys Phe Leu Gly Arg Phe Asn Asp Ile His
                325                 330                 335

Val Pro Val Arg Leu Glu Ser Val Lys Phe Ala Ser His Cys Leu Met
            340                 345                 350

Asn His Pro Asp Leu Ala Lys Asp Leu Thr Glu Tyr Leu Lys Val Arg
        355                 360                 365

Ser His Asp Pro Glu Glu Ala Ile Arg His Asp Val Ile Val Thr Ile
    370                 375                 380
```

```
Ile Thr Ala Ala Lys Arg Asp Leu Ala Leu Val Asn Asp Gln Leu Leu
385                 390                 395                 400

Gly Phe Val Arg Glu Arg Thr Leu Asp Lys Arg Trp Arg Val Arg Lys
                405                 410                 415

Glu Ala Met Met Gly Leu Ala Gln Leu Tyr Lys Lys Tyr Cys Leu His
            420                 425                 430

Gly Glu Ala Gly Lys Glu Ala Ala Glu Lys Val Ser Trp Ile Lys Asp
        435                 440                 445

Lys Leu Leu His Ile Tyr Tyr Gln Asn Ser Ile Asp Asp Lys Leu Leu
    450                 455                 460

Val Glu Lys Ile Phe Ala Gln Tyr Leu Val Pro His Asn Leu Glu Thr
465                 470                 475                 480

Glu Glu Arg Met Lys Cys Leu Tyr Tyr Leu Tyr Ala Ser Leu Asp Pro
                485                 490                 495

Asn Ala Val Lys Ala Leu Asn Glu Met Trp Lys Cys Gln Asn Met Leu
            500                 505                 510

Arg Ser His Val Arg Glu Leu Leu Asp Leu His Lys Gln Pro Thr Ser
        515                 520                 525

Glu Ala Asn Cys Ser Ala Met Phe Gly Lys Leu Met Thr Ile Ala Lys
    530                 535                 540

Asn Leu Pro Asp Pro Gly Lys Ala Gln Asp Phe Val Lys Lys Phe Asn
545                 550                 555                 560

Gln Val Leu Gly Asp Asp Glu Lys Leu Arg Ser Gln Leu Glu Leu Leu
                565                 570                 575

Ile Ser Pro Thr Cys Ser Cys Lys Gln Ala Asp Val Cys Val Arg Glu
            580                 585                 590

Ile Ala Arg Lys Leu Ala Asn Pro Lys Gln Pro Thr Asn Pro Phe Leu
        595                 600                 605

Glu Met Val Lys Phe Leu Leu Glu Arg Ile Ala Pro Val His Ile Asp
    610                 615                 620

Ser Glu Ala Ile Ser Ala Leu Val Lys Leu Met Asn Lys Ser Ile Glu
625                 630                 635                 640

Gly Thr Ala Asp Asp Glu Glu Glu Gly Val Ser Pro Asp Thr Ala Ile
                645                 650                 655

Arg Ser Gly Leu Glu Leu Leu Lys Val Leu Ser Phe Thr His Pro Thr
            660                 665                 670

Ser Phe His Ser Ala Glu Thr Tyr Glu Ser Leu Leu Gln Cys Leu Arg
        675                 680                 685

Met Glu Asp Asp Lys Val Ala Glu Ala Ala Ile Gln Ile Phe Arg Asn
    690                 695                 700

Thr Gly His Lys Ile Glu Thr Asp Leu Pro Gln Ile Arg Ser Thr Leu
705                 710                 715                 720

Ile Pro Ile Leu His Gln Lys Ala Lys Arg Gly Thr Pro His Gln Ala
                725                 730                 735

Lys Gln Ala Val His Cys Ile His Ala Ile Phe Thr Asn Lys Glu Val
            740                 745                 750

Gln Leu Ala Gln Ile Phe Glu Pro Leu Ser Arg Ser Leu Asn Ala Asp
        755                 760                 765

Val Pro Glu Gln Leu Ile Thr Pro Leu Val Ser Leu Gly His Ile Ser
    770                 775                 780

Met Leu Ala Pro Asp Gln Phe Ala Ser Pro Met Lys Ser Val Val Ala
785                 790                 795                 800
```

```
Asn Phe Ile Val Lys Asp Leu Leu Met Asn Asp Arg Ser Thr Gly Glu
                805                 810                 815

Lys Asn Gly Lys Leu Trp Ser Pro Asp Glu Glu Val Ser Pro Glu Val
            820                 825                 830

Leu Ala Lys Val Gln Ala Ile Lys Leu Leu Val Arg Trp Leu Leu Gly
        835                 840                 845

Met Lys Asn Asn Gln Ser Lys Ser Ala Asn Ser Thr Leu Arg Leu Leu
    850                 855                 860

Ser Ala Met Leu Val Ser Glu Gly Asp Leu Thr Glu Gln Lys Arg Ile
865                 870                 875                 880

Ser Lys Ser Asp Met Ser Arg Leu Arg Leu Ala Ala Gly Ser Ala Ile
                885                 890                 895

Met Lys Leu Ala Gln Glu Pro Cys Tyr His Glu Ile Ile Thr Pro Glu
            900                 905                 910

Gln Phe Gln Leu Cys Ala Leu Val Ile Asn Asp Glu Cys Tyr Gln Val
        915                 920                 925

Arg Gln Ile Phe Ala Gln Lys Leu His Lys Ala Leu Val Lys Leu Leu
    930                 935                 940

Leu Pro Leu Glu Tyr Met Ala Ile Phe Ala Leu Cys Ala Lys Asp Pro
945                 950                 955                 960

Val Lys Glu Arg Arg Ala His Ala Arg Gln Cys Leu Leu Lys Asn Ile
                965                 970                 975

Ser Ile Arg Arg Glu Tyr Ile Lys Gln Asn Pro Met Ala Thr Glu Lys
            980                 985                 990

Leu Leu Ser Leu Leu Pro Glu Tyr  Val Val Pro Tyr Met  Ile His Leu
        995                 1000                1005

Leu Ala  His Asp Pro Asp Phe  Thr Arg Ser Gln Asp  Val Asp Gln
    1010                 1015                 1020

Leu Arg  Asp Ile Lys Glu Cys  Leu Trp Phe Met Leu  Glu Val Leu
    1025                 1030                 1035

Met Thr  Lys Asn Glu Asn Asn  Ser His Ala Phe Met  Lys Lys Met
    1040                 1045                 1050

Ala Glu  Asn Ile Lys Leu Thr  Lys Asp Ala Gln Ser  Pro Asp Glu
    1055                 1060                 1065

Ser Lys  Thr Asn Glu Lys Leu  Tyr Thr Val Cys Asp  Val Ala Leu
    1070                 1075                 1080

Cys Val  Ile Asn Ser Lys Ser  Ala Leu Cys Asn Ala  Asp Ser Pro
    1085                 1090                 1095

Lys Asp  Pro Val Leu Pro Met  Lys Phe Phe Thr Gln  Pro Glu Lys
    1100                 1105                 1110

Asp Phe  Cys Asn Asp Lys Ser  Tyr Ile Ser Glu Glu  Thr Arg Val
    1115                 1120                 1125

Leu Leu  Leu Thr Gly Lys Pro  Lys Pro Ala Gly Val  Leu Gly Ala
    1130                 1135                 1140

Val Asn  Lys Pro Leu Ser Ala  Thr Gly Arg Lys Pro  Tyr Val Arg
    1145                 1150                 1155

Ser Thr  Gly Thr Glu Thr Gly  Ser Thr Ile Asn Val  Asn Ser Glu
    1160                 1165                 1170

Leu Asn  Pro Ser Thr Gly Ser  Arg Ser Arg Glu Gln  Ser Ser Glu
    1175                 1180                 1185

Ala Ala  Glu Thr Gly Val Ser  Glu Asn Glu Glu Asn  Pro Val Arg
    1190                 1195                 1200

Ile Ile  Ser Val Thr Pro Val  Lys Asn Ile Asp Pro  Val Lys Asn
```

```
    1205                1210                1215

Lys Glu  Ile Asn Ser Asp Gln  Ala Thr Gln Gly Asn  Ile Ser Ser
    1220                1225                1230

Asp Arg  Gly Lys Lys Arg Thr  Val Thr Ala Ala Gly  Thr Glu Asn
    1235                1240                1245

Ile Gln  Gln Lys Thr Asp Glu  Lys Val Asp Glu Ser  Gly Pro Pro
    1250                1255                1260

Ala Pro  Ser Lys Pro Arg Arg  Gly Arg Arg Pro Lys  Ser Glu Ser
    1265                1270                1275

Gln Gly  Asn Ala Thr Lys Asn  Asp Asp Ile Asn Lys  Pro Leu Ser
    1280                1285                1290

Lys Gly  Arg Lys Arg Ala Ala  Val Ser Gln Glu Ser  Pro Gly Gly
    1295                1300                1305

Leu Glu  Ala Gly Asn Ala Lys  Ala Pro Lys Leu Gln  Asp Ile Ala
    1310                1315                1320

Lys Lys  Ala Ala Pro Ala Glu  Arg Gln Ile Asp Leu  Gln Arg
    1325                1330                1335


<210> SEQ ID NO 11
<211> LENGTH: 4809
<212> TYPE: DNA
<213> ORGANISM: Gallus gallus
<220> FEATURE:
<221> NAME/KEY: CDS
<222> LOCATION: (231)..(4301)
<223> OTHER INFORMATION:

<400> SEQUENCE: 11

ggctgttctt ccccggccgg acggagagcg gcactgtgtc cccgcggcgc gcgctcggcg     60

gagcctcccc ctctccgctg ctgccgccgc cgccaccgag cagctccccc tccccccttcc    120

gagcagagcc gccgcaccgc cgcgcaggga ggaggcggcg ggagcgggcg ggcagcggcc    180

ggcggggcgg cggcggagcg gcgaggagcg gccggcgcgg aggccgctcc atg ctg       236
                                                       Met Leu
                                                       1

cac ctt ccg gag ctg cgt gag agg ccg gta gag gac tgt gca gaa gga      284
His Leu Pro Glu Leu Arg Glu Arg Pro Val Glu Asp Cys Ala Glu Gly
        5                   10                  15

aag ttt ctg agc agc ggc acc agg atg gac ttc ccg gct gcc caa cca      332
Lys Phe Leu Ser Ser Gly Thr Arg Met Asp Phe Pro Ala Ala Gln Pro
    20                  25                  30

aaa ccc gcc gcc gat ggt aaa atc atc tac tac ccg ccc gga gtg aag      380
Lys Pro Ala Ala Asp Gly Lys Ile Ile Tyr Tyr Pro Pro Gly Val Lys
35                  40                  45                  50

gag acc acc gac aaa att acc aac gat gag gtg gtg aaa cgg tta aag      428
Glu Thr Thr Asp Lys Ile Thr Asn Asp Glu Val Val Lys Arg Leu Lys
                55                  60                  65

atg gtg gta aaa acg ttc atg gat atg gac cag gac tca gaa gac gag      476
Met Val Val Lys Thr Phe Met Asp Met Asp Gln Asp Ser Glu Asp Glu
            70                  75                  80

aaa cag cag tat ctc cca tta gcc ttg cac ctt gca tct gaa ttc ttc      524
Lys Gln Gln Tyr Leu Pro Leu Ala Leu His Leu Ala Ser Glu Phe Phe
        85                  90                  95

ctc agg aat ccc aat aaa gat gtg cgc ctc ctt gta gca tgt tgc ttg      572
Leu Arg Asn Pro Asn Lys Asp Val Arg Leu Leu Val Ala Cys Cys Leu
    100                 105                 110

gct gat atc ttt cgt atc tat gct cct gaa gct cca tat act tcc cat      620
Ala Asp Ile Phe Arg Ile Tyr Ala Pro Glu Ala Pro Tyr Thr Ser His
115                 120                 125                 130
```

```
gac aaa ctt aag gac ata ttc ttg ttt att aca aga caa tta aaa ggc      668
Asp Lys Leu Lys Asp Ile Phe Leu Phe Ile Thr Arg Gln Leu Lys Gly
                135                 140                 145

ttg gag gac aca aag agc cct cag ttt aac aga tac ttt tac ttg tta      716
Leu Glu Asp Thr Lys Ser Pro Gln Phe Asn Arg Tyr Phe Tyr Leu Leu
            150                 155                 160

gag aat tta gct tgg gtt aaa tct tac aac atc tgc ttt gag ttg gaa      764
Glu Asn Leu Ala Trp Val Lys Ser Tyr Asn Ile Cys Phe Glu Leu Glu
        165                 170                 175

gat tgc aat gaa att ttt att cag ctt ttt agg act ctt ttt tca gtt      812
Asp Cys Asn Glu Ile Phe Ile Gln Leu Phe Arg Thr Leu Phe Ser Val
    180                 185                 190

atc aat aat agc cac aac cag aag gta caa atg cat atg ctg gat ttg      860
Ile Asn Asn Ser His Asn Gln Lys Val Gln Met His Met Leu Asp Leu
195                 200                 205                 210

atg agt tct atc atc atg gaa ggc gat gga gta act cag gag ctg ctg      908
Met Ser Ser Ile Ile Met Glu Gly Asp Gly Val Thr Gln Glu Leu Leu
                215                 220                 225

gac tcc att ttg att aac ctc att cct gca cac aag aac ctt aat aag      956
Asp Ser Ile Leu Ile Asn Leu Ile Pro Ala His Lys Asn Leu Asn Lys
            230                 235                 240

caa gca ttt gat ctt gca aaa gtc ctg ctg aaa agg act gtc cag acc     1004
Gln Ala Phe Asp Leu Ala Lys Val Leu Leu Lys Arg Thr Val Gln Thr
        245                 250                 255

att gaa ccg tgc att gcc aat ttt ttt aac cag gtt ctg gta ctg gga     1052
Ile Glu Pro Cys Ile Ala Asn Phe Phe Asn Gln Val Leu Val Leu Gly
    260                 265                 270

aag tct tca gta agt gac tta tca gaa cat gta ttt gac ttg ata cta     1100
Lys Ser Ser Val Ser Asp Leu Ser Glu His Val Phe Asp Leu Ile Leu
275                 280                 285                 290

gag ctt ttt gcc ata gat cct cac tta ctg ctg tct gtc atg ccc cag     1148
Glu Leu Phe Ala Ile Asp Pro His Leu Leu Leu Ser Val Met Pro Gln
                295                 300                 305

ctt gaa ttc aaa ctg aag agc aat gat gga gaa gaa cgt ttg gct gtt     1196
Leu Glu Phe Lys Leu Lys Ser Asn Asp Gly Glu Glu Arg Leu Ala Val
            310                 315                 320

gtt cga ctt ttg gct aaa ctc ttt ggc tct aaa gat tct gat ctg gcc     1244
Val Arg Leu Leu Ala Lys Leu Phe Gly Ser Lys Asp Ser Asp Leu Ala
        325                 330                 335

aca caa aat cgt cct ctt tgg cag tgc ttt ctt ggg cgg ttc aat gat     1292
Thr Gln Asn Arg Pro Leu Trp Gln Cys Phe Leu Gly Arg Phe Asn Asp
    340                 345                 350

atc cat gtc cct gtg aga tta gag agt gtg aaa ttc gcc agt cat tgt     1340
Ile His Val Pro Val Arg Leu Glu Ser Val Lys Phe Ala Ser His Cys
355                 360                 365                 370

tta atg aac cat cca gac tta gcg aaa gac ctc act gaa tat ttg aag     1388
Leu Met Asn His Pro Asp Leu Ala Lys Asp Leu Thr Glu Tyr Leu Lys
                375                 380                 385

gtt agg tca cat gac cca gag gaa gct att cga cac gat gtt att gtt     1436
Val Arg Ser His Asp Pro Glu Glu Ala Ile Arg His Asp Val Ile Val
            390                 395                 400

aca att att act gcg ggc aag aga gat ctt tcc tta gtc aat gat cag     1484
Thr Ile Ile Thr Ala Gly Lys Arg Asp Leu Ser Leu Val Asn Asp Gln
        405                 410                 415

ctg ctg ggc ttc gta agg gaa aga aca cta gac aaa cga tgg cga gta     1532
Leu Leu Gly Phe Val Arg Glu Arg Thr Leu Asp Lys Arg Trp Arg Val
    420                 425                 430

aga aaa gaa gct atg atg ggt ctt gcc cag cta tac aag aaa tac tgt     1580
Arg Lys Glu Ala Met Met Gly Leu Ala Gln Leu Tyr Lys Lys Tyr Cys
```

-continued

```
435                 440                 445                 450

ctt cat gcc gag gct gga aaa gat gct gca gag aaa gtg agc tgg ata      1628
Leu His Ala Glu Ala Gly Lys Asp Ala Ala Glu Lys Val Ser Trp Ile
                455                 460                 465

aag gat aaa ctt ttg cac ata tat tat caa aat agc att gat gac aaa      1676
Lys Asp Lys Leu Leu His Ile Tyr Tyr Gln Asn Ser Ile Asp Asp Lys
            470                 475                 480

tta cta gta gag aaa atc ttt gct cag tat ctt gtt cca cac aat ttg      1724
Leu Leu Val Glu Lys Ile Phe Ala Gln Tyr Leu Val Pro His Asn Leu
        485                 490                 495

gaa aca gaa gag cga atg aag tgc ttg tat tat ttg tat gcc agc ttg      1772
Glu Thr Glu Glu Arg Met Lys Cys Leu Tyr Tyr Leu Tyr Ala Ser Leu
    500                 505                 510

gat cca aat gct gtc aaa gca ctg aat gag atg tgg aag tgc cag aac      1820
Asp Pro Asn Ala Val Lys Ala Leu Asn Glu Met Trp Lys Cys Gln Asn
515                 520                 525                 530

atg ctg agg agt cac gta cga gaa tta cta gac ttg cat aag cag ccc      1868
Met Leu Arg Ser His Val Arg Glu Leu Leu Asp Leu His Lys Gln Pro
                535                 540                 545

aca tca gaa gca aac agt gct gcc atg ttt ggg aag ctg atg acc ata      1916
Thr Ser Glu Ala Asn Ser Ala Ala Met Phe Gly Lys Leu Met Thr Ile
            550                 555                 560

gca aaa aac ctt cca gat cct gga aaa gca caa gat ttt gtg aag aaa      1964
Ala Lys Asn Leu Pro Asp Pro Gly Lys Ala Gln Asp Phe Val Lys Lys
        565                 570                 575

ttc aat cag gtt cta ggc gat gat gaa aag ctt cgg tcc cag ctt gaa      2012
Phe Asn Gln Val Leu Gly Asp Asp Glu Lys Leu Arg Ser Gln Leu Glu
    580                 585                 590

ctg tta att agc cct acg tgt tct tgt aaa cag gca gat gtc tgt gtg      2060
Leu Leu Ile Ser Pro Thr Cys Ser Cys Lys Gln Ala Asp Val Cys Val
595                 600                 605                 610

aga gag ata gcc cgg aaa ctt gca aat cct aag cag cca aca aat cct      2108
Arg Glu Ile Ala Arg Lys Leu Ala Asn Pro Lys Gln Pro Thr Asn Pro
                615                 620                 625

ttt ctg gaa atg gtc aaa ttt ctt ttg gaa aga att gct cct gta cat      2156
Phe Leu Glu Met Val Lys Phe Leu Leu Glu Arg Ile Ala Pro Val His
            630                 635                 640

att gac tca gaa gcc att agt gca cta gta aaa ttg atg aat aaa tca      2204
Ile Asp Ser Glu Ala Ile Ser Ala Leu Val Lys Leu Met Asn Lys Ser
        645                 650                 655

ata gag ggg aca gct gat gat gaa gag gag ggt gta agt cct gat act      2252
Ile Glu Gly Thr Ala Asp Asp Glu Glu Glu Gly Val Ser Pro Asp Thr
    660                 665                 670

gca att cgt gca gga ctt gaa ctt ctc aag gtt ctg tcc ttt aca cat      2300
Ala Ile Arg Ala Gly Leu Glu Leu Leu Lys Val Leu Ser Phe Thr His
675                 680                 685                 690

cct acc tcg ttt cac tct gcg gag acc tat gag tct ctg ctg cag tgc      2348
Pro Thr Ser Phe His Ser Ala Glu Thr Tyr Glu Ser Leu Leu Gln Cys
                695                 700                 705

ctc agg atg gaa gat gat aag gta gct gag gca gcc ata cag att ttc      2396
Leu Arg Met Glu Asp Asp Lys Val Ala Glu Ala Ala Ile Gln Ile Phe
            710                 715                 720

aga aac acg ggt cac aaa ata gaa aca gac ctg cca cag ata aga tca      2444
Arg Asn Thr Gly His Lys Ile Glu Thr Asp Leu Pro Gln Ile Arg Ser
        725                 730                 735

aca tta att cca att ttg cat cag aaa gca aaa aga ggc act ccc cat      2492
Thr Leu Ile Pro Ile Leu His Gln Lys Ala Lys Arg Gly Thr Pro His
    740                 745                 750

cag gca aaa caa gcc gtt cac tgt ata cat gcc ata ttt tca aat aaa      2540
```

```
Gln Ala Lys Gln Ala Val His Cys Ile His Ala Ile Phe Ser Asn Lys
755                 760                 765                 770

gaa gtg caa ctt gct cag atc ttt gag cct ctt agt aga agt ttg aat      2588
Glu Val Gln Leu Ala Gln Ile Phe Glu Pro Leu Ser Arg Ser Leu Asn
                775                 780                 785

gct gat gta cca gaa caa ctg ata act cca tta gtc tca ctg ggt cac      2636
Ala Asp Val Pro Glu Gln Leu Ile Thr Pro Leu Val Ser Leu Gly His
            790                 795                 800

att tct atg ttg gct cca gac cag ttt gct tct cca atg aaa tct gtt      2684
Ile Ser Met Leu Ala Pro Asp Gln Phe Ala Ser Pro Met Lys Ser Val
        805                 810                 815

gtt gca aat ttc gtt gta aaa gat ctt cta atg aat gac agg tca aca      2732
Val Ala Asn Phe Val Val Lys Asp Leu Leu Met Asn Asp Arg Ser Thr
    820                 825                 830

ggt gag aaa aat gga aag ttg tgg tct cca gat gaa gag gtg tct cca      2780
Gly Glu Lys Asn Gly Lys Leu Trp Ser Pro Asp Glu Glu Val Ser Pro
835                 840                 845                 850

gaa gta cta gca aag gtg caa gca att aaa ctt ttg gta cgc tgg ctg      2828
Glu Val Leu Ala Lys Val Gln Ala Ile Lys Leu Leu Val Arg Trp Leu
                855                 860                 865

ctg ggt atg aaa aac aac cag tca aaa tct gca aat tcc aca ctc cga      2876
Leu Gly Met Lys Asn Asn Gln Ser Lys Ser Ala Asn Ser Thr Leu Arg
            870                 875                 880

ttg tta tca gct atg ctt gtc agt gaa gga gac ttg aca gaa cag aag      2924
Leu Leu Ser Ala Met Leu Val Ser Glu Gly Asp Leu Thr Glu Gln Lys
        885                 890                 895

cga atc agt aaa tcc gat atg tct cga cta cga tta gct gct ggc agt      2972
Arg Ile Ser Lys Ser Asp Met Ser Arg Leu Arg Leu Ala Ala Gly Ser
    900                 905                 910

gca ata atg aag ctt gca cag gaa cca tgt tac cat gaa ata att acc      3020
Ala Ile Met Lys Leu Ala Gln Glu Pro Cys Tyr His Glu Ile Ile Thr
915                 920                 925                 930

cca gaa cag ttc caa ctc tgt gcg ctc gtc att aat gat gag tgc tac      3068
Pro Glu Gln Phe Gln Leu Cys Ala Leu Val Ile Asn Asp Glu Cys Tyr
                935                 940                 945

caa gtg agg cag ata ttt gcc cag aaa ctg cat aaa gca ctt gtg aaa      3116
Gln Val Arg Gln Ile Phe Ala Gln Lys Leu His Lys Ala Leu Val Lys
            950                 955                 960

tta ctg ctc cct ttg gaa tat atg gca atc ttt gct ttg tgt gcc aaa      3164
Leu Leu Leu Pro Leu Glu Tyr Met Ala Ile Phe Ala Leu Cys Ala Lys
        965                 970                 975

gat cct gtg aaa gag aga aga gca cat gcc aga cag tgc ttg ctt aaa      3212
Asp Pro Val Lys Glu Arg Arg Ala His Ala Arg Gln Cys Leu Leu Lys
    980                 985                 990

aac atc agt ata cga aga  gag tat att aag cag  aat cct atg gct       3257
Asn Ile Ser Ile Arg Arg  Glu Tyr Ile Lys Gln  Asn Pro Met Ala
995                 1000                1005

aac  gaa aaa ttg ctg tcc  ttg ctg cct gaa tat  gtg gta cca tat      3302
Asn  Glu Lys Leu Leu Ser  Leu Leu Pro Glu Tyr  Val Val Pro Tyr
1010                 1015                 1020

atg  att cat tta ctg gca  cat gat cca gat ttc  aca aaa cct cag      3347
Met  Ile His Leu Leu Ala  His Asp Pro Asp Phe  Thr Lys Pro Gln
1025                 1030                 1035

gat  gtt gat cag ctt cgt  gat gtc aaa gag tgc  ctg tgg ttc atg      3392
Asp  Val Asp Gln Leu Arg  Asp Val Lys Glu Cys  Leu Trp Phe Met
1040                 1045                 1050

ctt  gaa gtt tta atg aca  aag aat gag aac aat  agc cat gcc ttc      3437
Leu  Glu Val Leu Met Thr  Lys Asn Glu Asn Asn  Ser His Ala Phe
1055                 1060                 1065
```

-continued

```
atg  aaa aag atg gca gaa  aac atc aag ctt aca  cga gat gcc cag      3482
Met  Lys Lys Met Ala Glu  Asn Ile Lys Leu Thr  Arg Asp Ala Gln
1070                 1075                 1080

tct  cct gat gag cca aag  gcc aat gag aaa ctt  tat aca gta tgt      3527
Ser  Pro Asp Glu Pro Lys  Ala Asn Glu Lys Leu  Tyr Thr Val Cys
1085                 1090                 1095

gat  gta gca ctg tgt gta  atc aac agc aaa agt  gct tta tgc aat      3572
Asp  Val Ala Leu Cys Val  Ile Asn Ser Lys Ser  Ala Leu Cys Asn
1100                 1105                 1110

gca  gat tca cca aag gac  cct gta ttg cca acc  aaa ttt ttt aca      3617
Ala  Asp Ser Pro Lys Asp  Pro Val Leu Pro Thr  Lys Phe Phe Thr
1115                 1120                 1125

caa  cct gaa aag gat ttt  tcc aat gac cgg aat  tac att tca gaa      3662
Gln  Pro Glu Lys Asp Phe  Ser Asn Asp Arg Asn  Tyr Ile Ser Glu
1130                 1135                 1140

gag  aca aga gtt ctt ctt  ttg aca gga aag cca  aaa cca act ggt      3707
Glu  Thr Arg Val Leu Leu  Leu Thr Gly Lys Pro  Lys Pro Thr Gly
1145                 1150                 1155

gtg  tta gat aca gta aac  aag cca ttg tct gca  act gga agg aga      3752
Val  Leu Asp Thr Val Asn  Lys Pro Leu Ser Ala  Thr Gly Arg Arg
1160                 1165                 1170

ccg  tat att aga act aca  gga tca gag act gga  agc aat atc agt      3797
Pro  Tyr Ile Arg Thr Thr  Gly Ser Glu Thr Gly  Ser Asn Ile Ser
1175                 1180                 1185

gta  aac tct gag ctg agc  tct tct gca gga aac  aga tca agg gaa      3842
Val  Asn Ser Glu Leu Ser  Ser Ser Ala Gly Asn  Arg Ser Arg Glu
1190                 1195                 1200

caa  agt tca gat ata tca  gaa act ggt gtc agt  gaa aac gat gaa      3887
Gln  Ser Ser Asp Ile Ser  Glu Thr Gly Val Ser  Glu Asn Asp Glu
1205                 1210                 1215

aac  cct gtg cga att att  tca gtc aca cca gca  aag aca gaa cct      3932
Asn  Pro Val Arg Ile Ile  Ser Val Thr Pro Ala  Lys Thr Glu Pro
1220                 1225                 1230

gtg  aaa aat aag gaa att  aat tct gac cag gct  acg caa gga aac      3977
Val  Lys Asn Lys Glu Ile  Asn Ser Asp Gln Ala  Thr Gln Gly Asn
1235                 1240                 1245

agt  act gaa cgt ggg aaa  aaa aga aca gca aca  gca tct gga act      4022
Ser  Thr Glu Arg Gly Lys  Lys Arg Thr Ala Thr  Ala Ser Gly Thr
1250                 1255                 1260

gag  aat att cat cag aaa  gca gaa gaa aac aat  gca gat gaa aca      4067
Glu  Asn Ile His Gln Lys  Ala Glu Glu Asn Asn  Ala Asp Glu Thr
1265                 1270                 1275

gga  cca tcg ctt gca gca  aaa acc agg aga ggg  cgt cca ccc aaa      4112
Gly  Pro Ser Leu Ala Ala  Lys Thr Arg Arg Gly  Arg Pro Pro Lys
1280                 1285                 1290

cct  gaa cct cag ggt acc  act gca aaa aat gag  gaa aca aat aag      4157
Pro  Glu Pro Gln Gly Thr  Thr Ala Lys Asn Glu  Glu Thr Asn Lys
1295                 1300                 1305

cca  cct gtc agg gga aga  aaa agg gca gca gcc  agt caa gaa agt      4202
Pro  Pro Val Arg Gly Arg  Lys Arg Ala Ala Ala  Ser Gln Glu Ser
1310                 1315                 1320

cca  ggg agt tta gag gca  ggt aac gcc aaa gca  cca aaa cag caa      4247
Pro  Gly Ser Leu Glu Ala  Gly Asn Ala Lys Ala  Pro Lys Gln Gln
1325                 1330                 1335

gac  aca gca aaa aag cca  gca gca gca cag aga  cag atc gat cta      4292
Asp  Thr Ala Lys Lys Pro  Ala Ala Ala Gln Arg  Gln Ile Asp Leu
1340                 1345                 1350

caa  agg taa aaagaaaact cactcgaaaa gggaggaaat gaaggccaaa            4341
Gln  Arg
1355
```

```
taaaggcatg ctccaagctt ctgcaaaaac taggattcag aaatttcctg tacaggaact   4401

gaaattgctt caaaacacac agctttcagc tctgaaaaca gaaggaaaac tatgcttccc   4461

tttcacgtga aattaatcct tctcaatgga aatgtaaagc agaaactctt gagaaagagg   4521

ctaaaagcat ctgtacttat ttccccagag actttttttta tgaaaagtca ataattaagc   4581

aaattgctta acacttggtt ccagttcctg cattctggag tttaaaagtg tatttacacc   4641

attaattttc atgctgcatt ttcttttttt ttttaaagga agtcagaggg aggtccttac   4701

actgacactg aaaattcgcg atcctagagc caggtattcc catgttccac agaaaaagta   4761

gaagtctact gaatggattt taaataagac tagaaaaaaa aaaaaaaa                4809
```

```
<210> SEQ ID NO 12
<211> LENGTH: 1356
<212> TYPE: PRT
<213> ORGANISM: Gallus gallus

<400> SEQUENCE: 12

Met Leu His Leu Pro Glu Leu Arg Glu Arg Pro Val Glu Asp Cys Ala
1               5                   10                  15

Glu Gly Lys Phe Leu Ser Ser Gly Thr Arg Met Asp Phe Pro Ala Ala
            20                  25                  30

Gln Pro Lys Pro Ala Ala Asp Gly Lys Ile Ile Tyr Tyr Pro Pro Gly
        35                  40                  45

Val Lys Glu Thr Thr Asp Lys Ile Thr Asn Asp Glu Val Val Lys Arg
    50                  55                  60

Leu Lys Met Val Val Lys Thr Phe Met Asp Met Asp Gln Asp Ser Glu
65                  70                  75                  80

Asp Glu Lys Gln Gln Tyr Leu Pro Leu Ala Leu His Leu Ala Ser Glu
                85                  90                  95

Phe Phe Leu Arg Asn Pro Asn Lys Asp Val Arg Leu Leu Val Ala Cys
            100                 105                 110

Cys Leu Ala Asp Ile Phe Arg Ile Tyr Ala Pro Glu Ala Pro Tyr Thr
        115                 120                 125

Ser His Asp Lys Leu Lys Asp Ile Phe Leu Phe Ile Thr Arg Gln Leu
    130                 135                 140

Lys Gly Leu Glu Asp Thr Lys Ser Pro Gln Phe Asn Arg Tyr Phe Tyr
145                 150                 155                 160

Leu Leu Glu Asn Leu Ala Trp Val Lys Ser Tyr Asn Ile Cys Phe Glu
                165                 170                 175

Leu Glu Asp Cys Asn Glu Ile Phe Ile Gln Leu Phe Arg Thr Leu Phe
            180                 185                 190

Ser Val Ile Asn Asn Ser His Asn Gln Lys Val Gln Met His Met Leu
        195                 200                 205

Asp Leu Met Ser Ser Ile Ile Met Glu Gly Asp Gly Val Thr Gln Glu
    210                 215                 220

Leu Leu Asp Ser Ile Leu Ile Asn Leu Ile Pro Ala His Lys Asn Leu
225                 230                 235                 240

Asn Lys Gln Ala Phe Asp Leu Ala Lys Val Leu Leu Lys Arg Thr Val
                245                 250                 255

Gln Thr Ile Glu Pro Cys Ile Ala Asn Phe Phe Asn Gln Val Leu Val
            260                 265                 270

Leu Gly Lys Ser Ser Val Ser Asp Leu Ser Glu His Val Phe Asp Leu
        275                 280                 285
```

```
Ile Leu Glu Leu Phe Ala Ile Asp Pro His Leu Leu Leu Ser Val Met
    290                 295                 300

Pro Gln Leu Glu Phe Lys Leu Lys Ser Asn Asp Gly Glu Glu Arg Leu
305                 310                 315                 320

Ala Val Val Arg Leu Leu Ala Lys Leu Phe Gly Ser Lys Asp Ser Asp
                325                 330                 335

Leu Ala Thr Gln Asn Arg Pro Leu Trp Gln Cys Phe Leu Gly Arg Phe
            340                 345                 350

Asn Asp Ile His Val Pro Val Arg Leu Glu Ser Val Lys Phe Ala Ser
        355                 360                 365

His Cys Leu Met Asn His Pro Asp Leu Ala Lys Asp Leu Thr Glu Tyr
    370                 375                 380

Leu Lys Val Arg Ser His Asp Pro Glu Glu Ala Ile Arg His Asp Val
385                 390                 395                 400

Ile Val Thr Ile Ile Thr Ala Gly Lys Arg Asp Leu Ser Leu Val Asn
                405                 410                 415

Asp Gln Leu Leu Gly Phe Val Arg Glu Arg Thr Leu Asp Lys Arg Trp
            420                 425                 430

Arg Val Arg Lys Glu Ala Met Met Gly Leu Ala Gln Leu Tyr Lys Lys
        435                 440                 445

Tyr Cys Leu His Ala Glu Ala Gly Lys Asp Ala Ala Glu Lys Val Ser
    450                 455                 460

Trp Ile Lys Asp Lys Leu Leu His Ile Tyr Tyr Gln Asn Ser Ile Asp
465                 470                 475                 480

Asp Lys Leu Leu Val Glu Lys Ile Phe Ala Gln Tyr Leu Val Pro His
                485                 490                 495

Asn Leu Glu Thr Glu Glu Arg Met Lys Cys Leu Tyr Tyr Leu Tyr Ala
            500                 505                 510

Ser Leu Asp Pro Asn Ala Val Lys Ala Leu Asn Glu Met Trp Lys Cys
        515                 520                 525

Gln Asn Met Leu Arg Ser His Val Arg Glu Leu Leu Asp Leu His Lys
    530                 535                 540

Gln Pro Thr Ser Glu Ala Asn Ser Ala Ala Met Phe Gly Lys Leu Met
545                 550                 555                 560

Thr Ile Ala Lys Asn Leu Pro Asp Pro Gly Lys Ala Gln Asp Phe Val
                565                 570                 575

Lys Lys Phe Asn Gln Val Leu Gly Asp Asp Glu Lys Leu Arg Ser Gln
            580                 585                 590

Leu Glu Leu Leu Ile Ser Pro Thr Cys Ser Cys Lys Gln Ala Asp Val
        595                 600                 605

Cys Val Arg Glu Ile Ala Arg Lys Leu Ala Asn Pro Lys Gln Pro Thr
    610                 615                 620

Asn Pro Phe Leu Glu Met Val Lys Phe Leu Leu Glu Arg Ile Ala Pro
625                 630                 635                 640

Val His Ile Asp Ser Glu Ala Ile Ser Ala Leu Val Lys Leu Met Asn
                645                 650                 655

Lys Ser Ile Glu Gly Thr Ala Asp Asp Glu Glu Glu Gly Val Ser Pro
            660                 665                 670

Asp Thr Ala Ile Arg Ala Gly Leu Glu Leu Leu Lys Val Leu Ser Phe
        675                 680                 685

Thr His Pro Thr Ser Phe His Ser Ala Glu Thr Tyr Glu Ser Leu Leu
    690                 695                 700

Gln Cys Leu Arg Met Glu Asp Asp Lys Val Ala Glu Ala Ala Ile Gln
```

```
705                 710                 715                 720

Ile Phe Arg Asn Thr Gly His Lys Ile Glu Thr Asp Leu Pro Gln Ile
                725                 730                 735

Arg Ser Thr Leu Ile Pro Ile Leu His Gln Lys Ala Lys Arg Gly Thr
            740                 745                 750

Pro His Gln Ala Lys Gln Ala Val His Cys Ile His Ala Ile Phe Ser
        755                 760                 765

Asn Lys Glu Val Gln Leu Ala Gln Ile Phe Glu Pro Leu Ser Arg Ser
    770                 775                 780

Leu Asn Ala Asp Val Pro Glu Gln Leu Ile Thr Pro Leu Val Ser Leu
785                 790                 795                 800

Gly His Ile Ser Met Leu Ala Pro Asp Gln Phe Ala Ser Pro Met Lys
                805                 810                 815

Ser Val Val Ala Asn Phe Val Val Lys Asp Leu Leu Met Asn Asp Arg
            820                 825                 830

Ser Thr Gly Glu Lys Asn Gly Lys Leu Trp Ser Pro Asp Glu Glu Val
        835                 840                 845

Ser Pro Glu Val Leu Ala Lys Val Gln Ala Ile Lys Leu Leu Val Arg
    850                 855                 860

Trp Leu Leu Gly Met Lys Asn Asn Gln Ser Lys Ser Ala Asn Ser Thr
865                 870                 875                 880

Leu Arg Leu Leu Ser Ala Met Leu Val Ser Glu Gly Asp Leu Thr Glu
                885                 890                 895

Gln Lys Arg Ile Ser Lys Ser Asp Met Ser Arg Leu Arg Leu Ala Ala
            900                 905                 910

Gly Ser Ala Ile Met Lys Leu Ala Gln Glu Pro Cys Tyr His Glu Ile
        915                 920                 925

Ile Thr Pro Glu Gln Phe Gln Leu Cys Ala Leu Val Ile Asn Asp Glu
    930                 935                 940

Cys Tyr Gln Val Arg Gln Ile Phe Ala Gln Lys Leu His Lys Ala Leu
945                 950                 955                 960

Val Lys Leu Leu Leu Pro Leu Glu Tyr Met Ala Ile Phe Ala Leu Cys
                965                 970                 975

Ala Lys Asp Pro Val Lys Glu Arg Arg Ala His Ala Arg Gln Cys Leu
            980                 985                 990

Leu Lys Asn Ile Ser Ile Arg Arg  Glu Tyr Ile Lys Gln  Asn Pro Met
        995                 1000                1005

Ala Asn  Glu Lys Leu Leu Ser  Leu Leu Pro Glu Tyr  Val Val Pro
    1010                1015                1020

Tyr Met  Ile His Leu Leu Ala  His Asp Pro Asp Phe  Thr Lys Pro
    1025                1030                1035

Gln Asp  Val Asp Gln Leu Arg  Asp Val Lys Glu Cys  Leu Trp Phe
    1040                1045                1050

Met Leu  Glu Val Leu Met Thr  Lys Asn Glu Asn Asn  Ser His Ala
    1055                1060                1065

Phe Met  Lys Lys Met Ala Glu  Asn Ile Lys Leu Thr  Arg Asp Ala
    1070                1075                1080

Gln Ser  Pro Asp Glu Pro Lys  Ala Asn Glu Lys Leu  Tyr Thr Val
    1085                1090                1095

Cys Asp  Val Ala Leu Cys Val  Ile Asn Ser Lys Ser  Ala Leu Cys
    1100                1105                1110

Asn Ala  Asp Ser Pro Lys Asp  Pro Val Leu Pro Thr  Lys Phe Phe
    1115                1120                1125
```

```
Thr Gln  Pro Glu Lys Asp Phe  Ser Asn Asp Arg Asn  Tyr Ile Ser
    1130                 1135                 1140

Glu Glu  Thr Arg Val Leu Leu  Leu Thr Gly Lys Pro  Lys Pro Thr
    1145                 1150                 1155

Gly Val  Leu Asp Thr Val Asn  Lys Pro Leu Ser Ala  Thr Gly Arg
    1160                 1165                 1170

Arg Pro  Tyr Ile Arg Thr Thr  Gly Ser Glu Thr Gly  Ser Asn Ile
    1175                 1180                 1185

Ser Val  Asn Ser Glu Leu Ser  Ser Ser Ala Gly Asn  Arg Ser Arg
    1190                 1195                 1200

Glu Gln  Ser Ser Asp Ile Ser  Glu Thr Gly Val Ser  Glu Asn Asp
    1205                 1210                 1215

Glu Asn  Pro Val Arg Ile Ile  Ser Val Thr Pro Ala  Lys Thr Glu
    1220                 1225                 1230

Pro Val  Lys Asn Lys Glu Ile  Asn Ser Asp Gln Ala  Thr Gln Gly
    1235                 1240                 1245

Asn Ser  Thr Glu Arg Gly Lys  Lys Arg Thr Ala Thr  Ala Ser Gly
    1250                 1255                 1260

Thr Glu  Asn Ile His Gln Lys  Ala Glu Glu Asn Asn  Ala Asp Glu
    1265                 1270                 1275

Thr Gly  Pro Ser Leu Ala Ala  Lys Thr Arg Arg Gly  Arg Pro Pro
    1280                 1285                 1290

Lys Pro  Glu Pro Gln Gly Thr  Thr Ala Lys Asn Glu  Glu Thr Asn
    1295                 1300                 1305

Lys Pro  Pro Val Arg Gly Arg  Lys Arg Ala Ala Ala  Ser Gln Glu
    1310                 1315                 1320

Ser Pro  Gly Ser Leu Glu Ala  Gly Asn Ala Lys Ala  Pro Lys Gln
    1325                 1330                 1335

Gln Asp  Thr Ala Lys Lys Pro  Ala Ala Ala Gln Arg  Gln Ile Asp
    1340                 1345                 1350

Leu Gln  Arg
    1355
```

<210> SEQ ID NO 13
<211> LENGTH: 20
<212> TYPE: DNA
<213> ORGANISM: Artificial
<220> FEATURE:
<223> OTHER INFORMATION: T3 primer

<400> SEQUENCE: 13
aattaaccct cactaaaggg 20

<210> SEQ ID NO 14
<211> LENGTH: 19
<212> TYPE: DNA
<213> ORGANISM: Artificial
<220> FEATURE:
<223> OTHER INFORMATION: T7 primer

<400> SEQUENCE: 14
taatacgact cactatagg 19

<210> SEQ ID NO 15
<211> LENGTH: 25
<212> TYPE: DNA
<213> ORGANISM: Artificial
<220> FEATURE:

<223> OTHER INFORMATION: primer sense

<400> SEQUENCE: 15
aatagcatcg atgacaaact gttgg 25

<210> SEQ ID NO 16
<211> LENGTH: 24
<212> TYPE: DNA
<213> ORGANISM: Artificial
<220> FEATURE:
<223> OTHER INFORMATION: primer antisense

<400> SEQUENCE: 16
ggtcaggcaa attctttgct atgg 24

<210> SEQ ID NO 17
<211> LENGTH: 21
<212> TYPE: DNA
<213> ORGANISM: Artificial
<220> FEATURE:
<223> OTHER INFORMATION: primer sense

<400> SEQUENCE: 17
gtaaggtggc tgttgggtat g 21

<210> SEQ ID NO 18
<211> LENGTH: 24
<212> TYPE: DNA
<213> ORGANISM: Artificial
<220> FEATURE:
<223> OTHER INFORMATION: primer antisense

<400> SEQUENCE: 18
ggctagcagg tgaatcatgt atgg 24

<210> SEQ ID NO 19
<211> LENGTH: 23
<212> TYPE: DNA
<213> ORGANISM: Artificial
<220> FEATURE:
<223> OTHER INFORMATION: primer antisense

<400> SEQUENCE: 19
acttctggta aggtggctgt tgg 23

<210> SEQ ID NO 20
<211> LENGTH: 25
<212> TYPE: DNA
<213> ORGANISM: Artificial
<220> FEATURE:
<223> OTHER INFORMATION: primer antisense

<400> SEQUENCE: 20
gggctaggag gtgaatcatg tatgg 25

<210> SEQ ID NO 21
<211> LENGTH: 18
<212> TYPE: DNA
<213> ORGANISM: Artificial
<220> FEATURE:
<223> OTHER INFORMATION: GAPDH primer

<400> SEQUENCE: 21
gggctgcttt taactctg 18

<210> SEQ ID NO 22
<211> LENGTH: 18
<212> TYPE: DNA
<213> ORGANISM: Artificial
<220> FEATURE:
<223> OTHER INFORMATION: GAPDH primer

<400> SEQUENCE: 22
ccaggaaatg agcttgac 18

<210> SEQ ID NO 23
<211> LENGTH: 20
<212> TYPE: DNA
<213> ORGANISM: Artificial
<220> FEATURE:
<223> OTHER INFORMATION: gapdh primer

<400> SEQUENCE: 23
cttcaccacc atggagaagg 20

<210> SEQ ID NO 24
<211> LENGTH: 20
<212> TYPE: DNA
<213> ORGANISM: Artificial
<220> FEATURE:
<223> OTHER INFORMATION: gapdh primer

<400> SEQUENCE: 24
tgaagtcgca ggagacaacc 20

<210> SEQ ID NO 25
<211> LENGTH: 33
<212> TYPE: DNA
<213> ORGANISM: Artificial
<220> FEATURE:
<223> OTHER INFORMATION: primer sense

<400> SEQUENCE: 25
atggacttca cgcagccgaa gcctgccact gcc 33

<210> SEQ ID NO 26
<211> LENGTH: 40
<212> TYPE: DNA
<213> ORGANISM: Artificial
<220> FEATURE:
<223> OTHER INFORMATION: primer antisense

<400> SEQUENCE: 26
ttacctttgt aaatcaattt gtctctctgc tggaactgcc 40

<210> SEQ ID NO 27
<211> LENGTH: 9
<212> TYPE: PRT
<213> ORGANISM: Homo sapiens

<400> SEQUENCE: 27

Asn Leu Ile Pro Ala His Lys Asn Leu
1               5

<210> SEQ ID NO 28
<211> LENGTH: 10
<212> TYPE: PRT
<213> ORGANISM: Homo sapiens

<400> SEQUENCE: 28

Lys Glu Cys Leu Trp Phe Met Leu Glu Val 1 5 10

<210> SEQ ID NO 29
<211> LENGTH: 10
<212> TYPE: PRT
<213> ORGANISM: Homo sapiens

<400> SEQUENCE: 29

Phe Leu Gly Arg Phe Asn Asp Ile His Val
1 5 10

<210> SEQ ID NO 30
<211> LENGTH: 10
<212> TYPE: PRT
<213> ORGANISM: Homo sapiens

<400> SEQUENCE: 30

Leu Leu Leu Pro Leu Glu Tyr Met Ala Ile
1 5 10

<210> SEQ ID NO 31
<211> LENGTH: 10
<212> TYPE: PRT
<213> ORGANISM: Homo sapiens

<400> SEQUENCE: 31

Ser Leu Asp Pro Asn Ala Val Lys Ala Leu
1 5 10

<210> SEQ ID NO 32
<211> LENGTH: 9
<212> TYPE: PRT
<213> ORGANISM: Homo sapiens

<400> SEQUENCE: 32

Lys Leu Lys Asp Ile Phe Leu Phe Ile
1 5

<210> SEQ ID NO 33
<211> LENGTH: 10
<212> TYPE: PRT
<213> ORGANISM: Homo sapiens

<400> SEQUENCE: 33

Leu Leu Ser Leu Leu Pro Glu Tyr Val Val
1 5 10

<210> SEQ ID NO 34
<211> LENGTH: 9
<212> TYPE: PRT
<213> ORGANISM: Homo sapiens

<400> SEQUENCE: 34

Lys Met Ala Glu Asn Ile Lys Leu Thr
1 5

<210> SEQ ID NO 35
<211> LENGTH: 10
<212> TYPE: PRT
<213> ORGANISM: Homo sapiens

<400> SEQUENCE: 35

Gln Val Leu Val Leu Gly Arg Ser Ser Val
1 5 10

<210> SEQ ID NO 36
<211> LENGTH: 9
<212> TYPE: PRT
<213> ORGANISM: Homo sapiens

<400> SEQUENCE: 36

Leu Gln Cys Cys Ser Ala Tyr Lys Leu
1               5

<210> SEQ ID NO 37
<211> LENGTH: 34
<212> TYPE: DNA
<213> ORGANISM: Artificial
<220> FEATURE:
<223> OTHER INFORMATION: primer sense

<400> SEQUENCE: 37
gcggccgcat ggacttcacc gcgcagccca agcc 34

<210> SEQ ID NO 38
<211> LENGTH: 45
<212> TYPE: DNA
<213> ORGANISM: Artificial
<220> FEATURE:
<223> OTHER INFORMATION: primer antisense

<400> SEQUENCE: 38
ctcgagttac ctttgtaagt caatctgtct ctctgctggt actgc 45

<210> SEQ ID NO 39
<211> LENGTH: 29
<212> TYPE: DNA
<213> ORGANISM: Artificial
<220> FEATURE:
<223> OTHER INFORMATION: primer sense

<400> SEQUENCE: 39
gcggccgcat ggacttcacc gcgcagccc 29

<210> SEQ ID NO 40
<211> LENGTH: 29
<212> TYPE: DNA
<213> ORGANISM: Artificial
<220> FEATURE:
<223> OTHER INFORMATION: primer antisense

<400> SEQUENCE: 40
ctcgagttac ctttgtaagt caatttgtc 29

<210> SEQ ID NO 41
<211> LENGTH: 31
<212> TYPE: DNA
<213> ORGANISM: Artificial
<220> FEATURE:
<223> OTHER INFORMATION: primer sense

<400> SEQUENCE: 41
gcggccgcat ggacttcacg cagccgaagc c 31

<210> SEQ ID NO 42
<211> LENGTH: 27
<212> TYPE: DNA
<213> ORGANISM: Artificial
<220> FEATURE:
<223> OTHER INFORMATION: primer antisense

```
<400> SEQUENCE: 42

ctcgagttac ctttgtaaat caatttg                                         27


<210> SEQ ID NO 43
<211> LENGTH: 7190
<212> TYPE: DNA
<213> ORGANISM: Homo sapiens
<220> FEATURE:
<221> NAME/KEY: CDS
<222> LOCATION: (541)..(4554)
<223> OTHER INFORMATION:

<400> SEQUENCE: 43

ggccggcgga ggaaggggag ggagcgagga gcgcgcgctg ctctcgcgtg ctctcgcgcc     60

gctcgcgtga ccggccggtg tgtgcgcgag gccccggctc ccggggcacg gacggccggg    120

cgcgcgcctc tgcgaggggc gtccgggtcc gagtcggcgg tccgggccgg cgcgaggtgc    180

gtgcgggcgg gccgcggggg tcccggacgg acacaagcgc acacactccc ggaggagcct    240

tcgaggctgc tcttcctcgg ccagacggag agcggcactg tctccccgcc cagcgctcac    300

tcgccccgcg tctccccccg cggcggctgc tcctcctcgg caccgccagc cccagcgccg    360

ctcccgggcg ggcgggcggc ggcggcggcg gcggcgggac ccgcggagcc gctttgtgtg    420

cagcccgact aggggcggcg gcgcaaccac ctgacagagg cccgggcgct cgatgcacct    480

tccgcccgca tgaggaggag aggccggtag aggactgtga accaaaagtt gtcccccagg    540

atg gac ttc acc gcg cag ccc aag cct gcc act gcc ctc tgt ggc gtc      588
Met Asp Phe Thr Ala Gln Pro Lys Pro Ala Thr Ala Leu Cys Gly Val
1               5                   10                  15

gtg agt gcc gac ggg aag atc gct tac cct ccg ggg gta aaa gag atc      636
Val Ser Ala Asp Gly Lys Ile Ala Tyr Pro Pro Gly Val Lys Glu Ile
            20                  25                  30

acc gac aag atc acc acg gac gag atg atc aaa cgc ctg aag atg gta      684
Thr Asp Lys Ile Thr Thr Asp Glu Met Ile Lys Arg Leu Lys Met Val
        35                  40                  45

gtg aaa acc ttt atg gat atg gat cag gac tca gaa gat gaa aaa cag      732
Val Lys Thr Phe Met Asp Met Asp Gln Asp Ser Glu Asp Glu Lys Gln
    50                  55                  60

cag tat ctc cca cta gcc ttg cat ctt gca tct gaa ttc ttc ctc agg      780
Gln Tyr Leu Pro Leu Ala Leu His Leu Ala Ser Glu Phe Phe Leu Arg
65                  70                  75                  80

aac ccc aat aaa gat gtg cgt ctc ctt gta gca tgt tgt ttg gct gat      828
Asn Pro Asn Lys Asp Val Arg Leu Leu Val Ala Cys Cys Leu Ala Asp
                85                  90                  95

atc ttt cgt atc tat gcc cca gaa gct cca tat act tcc cat gat aaa      876
Ile Phe Arg Ile Tyr Ala Pro Glu Ala Pro Tyr Thr Ser His Asp Lys
            100                 105                 110

ctt aag gac ata ttt ttg ttt att acc aga caa tta aaa ggt ttg gag      924
Leu Lys Asp Ile Phe Leu Phe Ile Thr Arg Gln Leu Lys Gly Leu Glu
        115                 120                 125

gat aca aag agt cca cag ttt aat aga tac ttt tat tta tta gag aat      972
Asp Thr Lys Ser Pro Gln Phe Asn Arg Tyr Phe Tyr Leu Leu Glu Asn
    130                 135                 140

tta gct tgg gtt aaa tca tat aac atc tgc ttt gaa ttg gaa gat tgc     1020
Leu Ala Trp Val Lys Ser Tyr Asn Ile Cys Phe Glu Leu Glu Asp Cys
145                 150                 155                 160

aat gaa att ttt att cag ctt ttt aga act ctc ttc tca gtg atc aac     1068
Asn Glu Ile Phe Ile Gln Leu Phe Arg Thr Leu Phe Ser Val Ile Asn
                165                 170                 175

aat agc cac aat aag aag gta caa atg cac atg cta gat ttg atg agt     1116
```

-continued

```
Asn Ser His Asn Lys Lys Val Gln Met His Met Leu Asp Leu Met Ser
            180                 185                 190

tct atc atc atg gaa ggt gat gga gtt act caa gaa tta ttg gac tcc      1164
Ser Ile Ile Met Glu Gly Asp Gly Val Thr Gln Glu Leu Leu Asp Ser
        195                 200                 205

att ctt att aac ctc att cct gca cat aag aac tta aat aaa cag tcc      1212
Ile Leu Ile Asn Leu Ile Pro Ala His Lys Asn Leu Asn Lys Gln Ser
    210                 215                 220

ttt gac ctt gca aaa gtg cta ttg aaa aga aca gtc cag act att gag      1260
Phe Asp Leu Ala Lys Val Leu Leu Lys Arg Thr Val Gln Thr Ile Glu
225                 230                 235                 240

gca tgc att gct aat ttt ttc aat caa gtc ctg gtg ctg gga aga tca      1308
Ala Cys Ile Ala Asn Phe Phe Asn Gln Val Leu Val Leu Gly Arg Ser
                245                 250                 255

tca gta agt gat ttg tca gaa cat gta ttt gat ctg att cag gaa ctt      1356
Ser Val Ser Asp Leu Ser Glu His Val Phe Asp Leu Ile Gln Glu Leu
            260                 265                 270

ttt gct ata gat cct cat tta tta tta tcc gtc atg cca cag ctt gaa      1404
Phe Ala Ile Asp Pro His Leu Leu Leu Ser Val Met Pro Gln Leu Glu
        275                 280                 285

ttc aaa cta aag agc aat gat gga gaa gag cga tta gct gtt gtt cga      1452
Phe Lys Leu Lys Ser Asn Asp Gly Glu Glu Arg Leu Ala Val Val Arg
    290                 295                 300

ctt cta gct aaa ttg ttt ggc tcc aaa gat tct gat ttg gca aca cag      1500
Leu Leu Ala Lys Leu Phe Gly Ser Lys Asp Ser Asp Leu Ala Thr Gln
305                 310                 315                 320

aat cgt cct ctt tgg caa tgt ttt ctt gga cga ttt aat gat att cat      1548
Asn Arg Pro Leu Trp Gln Cys Phe Leu Gly Arg Phe Asn Asp Ile His
                325                 330                 335

gtt cct gtg aga tta gaa agt gtg aaa ttt gcc agt cat tgt tta atg      1596
Val Pro Val Arg Leu Glu Ser Val Lys Phe Ala Ser His Cys Leu Met
            340                 345                 350

aat cac cca gat tta gcg aag gat ctc aca gaa tat tta aag gtt aga      1644
Asn His Pro Asp Leu Ala Lys Asp Leu Thr Glu Tyr Leu Lys Val Arg
        355                 360                 365

tca cat gat cca gaa gaa gct att cgt cat gat gtc att gtt act ata      1692
Ser His Asp Pro Glu Glu Ala Ile Arg His Asp Val Ile Val Thr Ile
    370                 375                 380

ata aca gct gcc aag agg gac ctg gcc tta gta aat gat cag ctg ctt      1740
Ile Thr Ala Ala Lys Arg Asp Leu Ala Leu Val Asn Asp Gln Leu Leu
385                 390                 395                 400

ggc ttt gta agg gaa aga aca ctg gat aaa cgg tgg cga gta aga aaa      1788
Gly Phe Val Arg Glu Arg Thr Leu Asp Lys Arg Trp Arg Val Arg Lys
                405                 410                 415

gaa gct atg atg ggt ctg gct cag ctt tat aag aaa tac tgt ctt cat      1836
Glu Ala Met Met Gly Leu Ala Gln Leu Tyr Lys Lys Tyr Cys Leu His
            420                 425                 430

ggt gaa gca gga aag gaa gct gca gag aaa gtc agc tgg ata aag gac      1884
Gly Glu Ala Gly Lys Glu Ala Ala Glu Lys Val Ser Trp Ile Lys Asp
        435                 440                 445

aaa ctt ctg cat att tat tat cag aac agc att gac gac aaa ctg ttg      1932
Lys Leu Leu His Ile Tyr Tyr Gln Asn Ser Ile Asp Asp Lys Leu Leu
    450                 455                 460

gta gag aaa atc ttt gct cag tat ctt gtc ccc cac aac ctg gaa aca      1980
Val Glu Lys Ile Phe Ala Gln Tyr Leu Val Pro His Asn Leu Glu Thr
465                 470                 475                 480

gaa gag aga atg aaa tgc tta tat tac tta tat gct agt ttg gat cca      2028
Glu Glu Arg Met Lys Cys Leu Tyr Tyr Leu Tyr Ala Ser Leu Asp Pro
                485                 490                 495
```

```
aat gct gta aaa gct ctc aac gaa atg tgg aag tgt cag aac atg ctt      2076
Asn Ala Val Lys Ala Leu Asn Glu Met Trp Lys Cys Gln Asn Met Leu
            500                 505                 510

cgg agc cat gta cgc gaa cta ttg gat ttg cac aag cag cct aca tca      2124
Arg Ser His Val Arg Glu Leu Leu Asp Leu His Lys Gln Pro Thr Ser
        515                 520                 525

gag gct aac tgt tct gcc atg ttt gga aaa ctg atg acc ata gca aag      2172
Glu Ala Asn Cys Ser Ala Met Phe Gly Lys Leu Met Thr Ile Ala Lys
    530                 535                 540

aat ttg cct gac ccc ggg aaa gca caa gat ttt gtg aag aaa ttt aac      2220
Asn Leu Pro Asp Pro Gly Lys Ala Gln Asp Phe Val Lys Lys Phe Asn
545                 550                 555                 560

cag gtt ctc ggc gat gat gag aaa ctt cgg tct cag ttg gag tta tta      2268
Gln Val Leu Gly Asp Asp Glu Lys Leu Arg Ser Gln Leu Glu Leu Leu
                565                 570                 575

att agc cca acc tgt tct tgc aaa caa gca gat att tgt gtg aga gaa      2316
Ile Ser Pro Thr Cys Ser Cys Lys Gln Ala Asp Ile Cys Val Arg Glu
            580                 585                 590

ata gcc cgg aaa ctt gca aat cct aag caa cca aca aat cct ttt cta      2364
Ile Ala Arg Lys Leu Ala Asn Pro Lys Gln Pro Thr Asn Pro Phe Leu
        595                 600                 605

gag atg gtc aaa ttt ctg ttg gaa aga atc gca cct gtg cac att gat      2412
Glu Met Val Lys Phe Leu Leu Glu Arg Ile Ala Pro Val His Ile Asp
    610                 615                 620

tca gaa gcc ata agt gca cta gtg aaa ttg atg aat aag tca ata gag      2460
Ser Glu Ala Ile Ser Ala Leu Val Lys Leu Met Asn Lys Ser Ile Glu
625                 630                 635                 640

ggg aca gca gat gat gaa gag gag ggt gta agt cca gat aca gct atc      2508
Gly Thr Ala Asp Asp Glu Glu Glu Gly Val Ser Pro Asp Thr Ala Ile
                645                 650                 655

cgt tca gga ctt gaa ctt ctt aag gtt ctg tct ttt aca cat cct acc      2556
Arg Ser Gly Leu Glu Leu Leu Lys Val Leu Ser Phe Thr His Pro Thr
            660                 665                 670

tcg ttc cac tct gca gag aca tat gag tcc ttg tta cag tgc cta aga      2604
Ser Phe His Ser Ala Glu Thr Tyr Glu Ser Leu Leu Gln Cys Leu Arg
        675                 680                 685

atg gag gat gac aag gta gca gaa gct gct att caa att ttt aga aat      2652
Met Glu Asp Asp Lys Val Ala Glu Ala Ala Ile Gln Ile Phe Arg Asn
    690                 695                 700

aca ggt cac aaa ata gaa aca gac ctt ccc cag ata cga tcg acc tta      2700
Thr Gly His Lys Ile Glu Thr Asp Leu Pro Gln Ile Arg Ser Thr Leu
705                 710                 715                 720

att ccc att tta cat caa aaa gca aag agg ggt act cca cac caa gca      2748
Ile Pro Ile Leu His Gln Lys Ala Lys Arg Gly Thr Pro His Gln Ala
                725                 730                 735

aaa cag gct gtg cac tgt ata cac gcc ata ttc aca aat aaa gaa gtc      2796
Lys Gln Ala Val His Cys Ile His Ala Ile Phe Thr Asn Lys Glu Val
            740                 745                 750

cag ctt gca cag att ttt gag cca ctc agt agg agt ctg aat gct gat      2844
Gln Leu Ala Gln Ile Phe Glu Pro Leu Ser Arg Ser Leu Asn Ala Asp
        755                 760                 765

gtg cca gaa caa ctt ata act cca tta gtt tca ttg ggc cac att tct      2892
Val Pro Glu Gln Leu Ile Thr Pro Leu Val Ser Leu Gly His Ile Ser
    770                 775                 780

atg tta gca cca gat cag ttt gct tcc cca atg aaa tct gta gta gca      2940
Met Leu Ala Pro Asp Gln Phe Ala Ser Pro Met Lys Ser Val Val Ala
785                 790                 795                 800

aat ttt att gtg aaa gat ctg cta atg aat gac agg tca aca ggt gaa      2988
Asn Phe Ile Val Lys Asp Leu Leu Met Asn Asp Arg Ser Thr Gly Glu
                805                 810                 815
```

```
aag aat gga aaa ctg tgg tct cca gat gaa gag gtt tcc cct gaa gta      3036
Lys Asn Gly Lys Leu Trp Ser Pro Asp Glu Glu Val Ser Pro Glu Val
            820                 825                 830

cta gca aag gta cag gca att aaa ctt ctg gta agg tgg ctg ttg ggt      3084
Leu Ala Lys Val Gln Ala Ile Lys Leu Leu Val Arg Trp Leu Leu Gly
        835                 840                 845

atg aaa aac aac cag tct aaa tct gcc aat tca acc ctt cgg tta tta      3132
Met Lys Asn Asn Gln Ser Lys Ser Ala Asn Ser Thr Leu Arg Leu Leu
    850                 855                 860

tca gcg atg ttg gtt agt gag ggt gac ctg aca gag caa aag agg atc      3180
Ser Ala Met Leu Val Ser Glu Gly Asp Leu Thr Glu Gln Lys Arg Ile
865                 870                 875                 880

agt aaa tct gat atg tct cgc ttg cga tta gct gct ggt agt gcc ata      3228
Ser Lys Ser Asp Met Ser Arg Leu Arg Leu Ala Ala Gly Ser Ala Ile
                885                 890                 895

atg aag ctt gct cag gaa cct tgt tac cat gaa att att acc cca gaa      3276
Met Lys Leu Ala Gln Glu Pro Cys Tyr His Glu Ile Ile Thr Pro Glu
            900                 905                 910

cag ttt cag ctc tgt gca ctt gtt att aat gat gag tgt tac caa gta      3324
Gln Phe Gln Leu Cys Ala Leu Val Ile Asn Asp Glu Cys Tyr Gln Val
        915                 920                 925

agg cag ata ttt gct cag aag ctg cat aag gca ctt gtg aag tta ctg      3372
Arg Gln Ile Phe Ala Gln Lys Leu His Lys Ala Leu Val Lys Leu Leu
    930                 935                 940

ctc cca ttg gag tat atg gcg atc ttt gcc ttg tgt gcc aaa gat cct      3420
Leu Pro Leu Glu Tyr Met Ala Ile Phe Ala Leu Cys Ala Lys Asp Pro
945                 950                 955                 960

gtg aag gag aga aga gca cac gca cga caa tgt tta ctg aaa aat atc      3468
Val Lys Glu Arg Arg Ala His Ala Arg Gln Cys Leu Leu Lys Asn Ile
                965                 970                 975

agt ata cgc agg gaa tac att aag cag aat cct atg gct act gag aaa      3516
Ser Ile Arg Arg Glu Tyr Ile Lys Gln Asn Pro Met Ala Thr Glu Lys
            980                 985                 990

tta tta tca ctg ttg cct gaa tat  gta gtt cca tac atg  att cac ctg   3564
Leu Leu Ser Leu Leu Pro Glu Tyr  Val Val Pro Tyr Met  Ile His Leu
        995                 1000                1005

cta gcc  cat gat cca gat ttt  aca aga tca caa gat  gtt gat cag      3609
Leu Ala  His Asp Pro Asp Phe  Thr Arg Ser Gln Asp  Val Asp Gln
    1010                1015                1020

ctt cgt  gat atc aaa gag tgc  cta tgg ttc atg ctt  gaa gtt tta      3654
Leu Arg  Asp Ile Lys Glu Cys  Leu Trp Phe Met Leu  Glu Val Leu
    1025                1030                1035

atg aca  aag aat gaa aac aat  agc cat gcc ttt atg  aag aag atg      3699
Met Thr  Lys Asn Glu Asn Asn  Ser His Ala Phe Met  Lys Lys Met
    1040                1045                1050

gca gag  aac atc aag tta acc  aga gat gcc cag tct  cca gat gaa      3744
Ala Glu  Asn Ile Lys Leu Thr  Arg Asp Ala Gln Ser  Pro Asp Glu
    1055                1060                1065

tcc aag  aca aat gaa aaa ctg  tat aca gta tgt gat  gtg gct ctc      3789
Ser Lys  Thr Asn Glu Lys Leu  Tyr Thr Val Cys Asp  Val Ala Leu
    1070                1075                1080

tgt gtt  ata aat agt aaa agt  gct ttg tgc aat gca  gat tca cca      3834
Cys Val  Ile Asn Ser Lys Ser  Ala Leu Cys Asn Ala  Asp Ser Pro
    1085                1090                1095

aag gac  cca gtc ctc cca atg  aaa ttt ttt aca caa  cct gaa aag      3879
Lys Asp  Pro Val Leu Pro Met  Lys Phe Phe Thr Gln  Pro Glu Lys
    1100                1105                1110

gac ttc  tgt aac gat aag agt  tat att tca gaa gag  aca aga gta      3924
Asp Phe  Cys Asn Asp Lys Ser  Tyr Ile Ser Glu Glu  Thr Arg Val
```

```
    1115                1120                1125

ctt ctg  tta aca gga aag cca  aag cct gct gga gta  cta ggt gca      3969
Leu Leu  Leu Thr Gly Lys Pro  Lys Pro Ala Gly Val  Leu Gly Ala
    1130                1135                1140

gta aat  aag cct tta tca gca  acg gga agg aaa ccc  tat gtt aga      4014
Val Asn  Lys Pro Leu Ser Ala  Thr Gly Arg Lys Pro  Tyr Val Arg
    1145                1150                1155

agc act  ggc act gag act gga  agc aat att aat gta  aat tca gag      4059
Ser Thr  Gly Thr Glu Thr Gly  Ser Asn Ile Asn Val  Asn Ser Glu
    1160                1165                1170

ctg aac  cct tca acc gga aat  cga tca agg gaa cag  agt tca gag      4104
Leu Asn  Pro Ser Thr Gly Asn  Arg Ser Arg Glu Gln  Ser Ser Glu
    1175                1180                1185

gca gca  gaa act gga gtt agt  gaa aat gaa gag aac  cct gtg agg      4149
Ala Ala  Glu Thr Gly Val Ser  Glu Asn Glu Glu Asn  Pro Val Arg
    1190                1195                1200

att att  tca gtc aca cct gta  aag aat att gac cca  gta aag aat      4194
Ile Ile  Ser Val Thr Pro Val  Lys Asn Ile Asp Pro  Val Lys Asn
    1205                1210                1215

aag gaa  att aat tct gat cag  gct acc cag ggc aac  atc agc agt      4239
Lys Glu  Ile Asn Ser Asp Gln  Ala Thr Gln Gly Asn  Ile Ser Ser
    1220                1225                1230

gac cga  gga aag aaa aga aca  gta aca gca gct ggt  gca gag aat      4284
Asp Arg  Gly Lys Lys Arg Thr  Val Thr Ala Ala Gly  Ala Glu Asn
    1235                1240                1245

atc caa  caa aaa aca gat gag  aaa gta gat gaa tcg  gga cct ccc      4329
Ile Gln  Gln Lys Thr Asp Glu  Lys Val Asp Glu Ser  Gly Pro Pro
    1250                1255                1260

gcc cct  tcc aaa ccc agg aga  gga cgt cga ccc aag  tct gaa tct      4374
Ala Pro  Ser Lys Pro Arg Arg  Gly Arg Arg Pro Lys  Ser Glu Ser
    1265                1270                1275

cag ggc  aat gct acc aaa aat  gat gat cta aat aaa  cct att aac      4419
Gln Gly  Asn Ala Thr Lys Asn  Asp Asp Leu Asn Lys  Pro Ile Asn
    1280                1285                1290

aag gga  agg aag aga gct gca  gtg ggt cag gag agc  cct ggg ggt      4464
Lys Gly  Arg Lys Arg Ala Ala  Val Gly Gln Glu Ser  Pro Gly Gly
    1295                1300                1305

ttg gaa  gca ggt aat gcc aaa  gca ccc aaa ctg caa  gat tta gcc      4509
Leu Glu  Ala Gly Asn Ala Lys  Ala Pro Lys Leu Gln  Asp Leu Ala
    1310                1315                1320

aaa aag  gca gca cca gca gaa  aga caa att gac tta  caa agg taa      4554
Lys Lys  Ala Ala Pro Ala Glu  Arg Gln Ile Asp Leu  Gln Arg
    1325                1330                1335

aaatgcattt gcaaagggag aaaatgaagg ccaaacagaa gcaggctcca gcttctgcaa   4614

aaacttggat tcacaaatgt ccctgaacag aaaatgaagc tcacttcaga acacacactc   4674

tctgccttga aaactaaaga gactattact tccttttcac atgaccacaa gtcctctgat   4734

ggaaatgtac agcagaaact cttgagagag aggctaaaag caactctgtt ctccccccttc  4794

ccctagactt ttcttacgaa aagtcaataa ttaagcaaat tgcttaacac ttggttccag   4854

ttcctgccta tctggagttt aaatgcgtaa tacaccatta atttccacgc tgcagttttt   4914

attttaaaga aagtaacaag atgtctttac actgacactg aaaattcatc cattttagag   4974

ccaggaattc ccatgttaca caggaaaaaa tagaagtcta ctgaattaat tttttaaaag   5034

aaaagagatc agattaaata tttctttgtt tttccttttg gaaactttta tgtataattc   5094

tttctgcctg cctacttttc tgcaaaaatg agatgtacag atttcggttc cctgctatga   5154

aaagtgatgt ggtagcaatt ttataaatgt tgctttctga tttttatcag agtgagaaaa   5214
```

```
ttaaaattat tgatttgcaa gtagtaaaca gttcatattt tgatttcccc tcattttagt   5274
ttaatataat ttgcaataaa tgtacatatt gttgtttgtt tcataaagca tatcacttta   5334
aaatggtttt tactcctgtg attatgttgg aatatttgga attttaaagg agtaaagact   5394
gtccagcatt tggttttata atgtttgtca ccagattttt attaatgtaa aaaaaatcaa   5454
tttttaaaaa atagttggac tttggcagct tttaaggaaa gttggaggtg ttttaggatt   5514
gctatcaatt ttcagcattg tgctatttgg aaataagtgt tttgcttttg tctgatggtc   5574
tgggctcatt tttatgttta ttttagaaaa ctgttgcatc aatatattat gtttcttggc   5634
attgttcagc ataggtaatg tgtgcacttt atgtgtacac ataatcatat ttaagttttt   5694
tgcataaaat aaatgcttct agatgtcatg gcagtctttt taatcttttt atcatatgct   5754
ttcttgtgaa ttttttcatg ttaaagagct aaagtcataa catgattaca gtcaactctc   5814
cattatctat ataaaatagt gactaagcct caggttttta attttgtgat aacaaaataa   5874
cgaaggcatg taagacctga ttctggagga acatgaaatt tgtcttttct catgtccaga   5934
gttctatcct gcccccactg tccactgtag ggtcatccgc aaagccctag cagaatgtgc   5994
tcactccatt tccttacacg tttctagcat gggtcagagg aaacaacatt tgtgttataa   6054
cttcgtcttg ataggctgta gtgtacatgg gatgtaaaac aaacaagtgt atcaaaggtg   6114
gatgattctg ttagagtgaa gtttgagagt aaatgtcact tacgtttctc atagataatc   6174
aagagttggc tgtgtattga ctgaaagatg ggtaattatt ttaaatatgc atttacacac   6234
atttaggtat cagaagatgc ttagggaaca atggatacca atgatagaaa atgatacctt   6294
tacaggggca gaaaaatccc cactcttcct tattgcctct tcagaaccct ttagaaagta   6354
taaaatattg cctccaacat gctgaaaaag agtatctatg cataagtatc agagaagtcc   6414
ctcaagcaat cagtaggtgt gttctattta gagagagttt aaagttctct tagcatcaga   6474
caacttgatt cctaaggttt ccagtgtgtc accaacaaaa agtgcattga tagggacctt   6534
tgtctcttcc tccctttgat taattgcccg gcatcacagt ttactagatt accaagtgtt   6594
acatcatatt aaataaaatg tagcagaacc atctgcatca atatattcct gtttagattt   6654
ttgcaggaga gaagttaaaa ggatttgctc cttgtatgat gtaagtggcc caccccaatt   6714
ttgtaacatg atgcaagtgt ctggcactaa gggaagcaag agtagggttg tggaaagacc   6774
aagctgatgg ggagggactt gtttacggga atttttttag ttttcctttt caaaggaaaa   6834
cattaaaatc ccttaggaat ttggtattca catctcagag aactacaaca caaaagtgca   6894
gacttatatt tgagaattaa tgttaaccct ttgtgtctag tttgaagctt cttgtatttg   6954
tctaaaacaa caagccagaa ttttgtatct cctttgataa aaagtgtgta taatgtaaag   7014
tagttttgca tattcttgtg ctgcacatgg gctgaatttt taaatttttt ttaaaaactt   7074
gaagcagaac cttgtaattt gtgtaaatga caagtgtaaa atcctaccat aaaatgctaa   7134
aaatatgcac tgtttcaaat aaaaccaaga aatgcagcat taaaaaaaaa aaaaaa       7190
```

<210> SEQ ID NO 44
<211> LENGTH: 1337
<212> TYPE: PRT
<213> ORGANISM: Homo sapiens

<400> SEQUENCE: 44

```
Met Asp Phe Thr Ala Gln Pro Lys Pro Ala Thr Ala Leu Cys Gly Val
1               5                   10                  15

Val Ser Ala Asp Gly Lys Ile Ala Tyr Pro Pro Gly Val Lys Glu Ile
```

```
            20                  25                  30

Thr Asp Lys Ile Thr Thr Asp Glu Met Ile Lys Arg Leu Lys Met Val
        35                  40                  45

Val Lys Thr Phe Met Asp Met Asp Gln Asp Ser Glu Asp Glu Lys Gln
    50                  55                  60

Gln Tyr Leu Pro Leu Ala Leu His Leu Ala Ser Glu Phe Phe Leu Arg
65                  70                  75                  80

Asn Pro Asn Lys Asp Val Arg Leu Leu Val Ala Cys Cys Leu Ala Asp
                85                  90                  95

Ile Phe Arg Ile Tyr Ala Pro Glu Ala Pro Tyr Thr Ser His Asp Lys
            100                 105                 110

Leu Lys Asp Ile Phe Leu Phe Ile Thr Arg Gln Leu Lys Gly Leu Glu
        115                 120                 125

Asp Thr Lys Ser Pro Gln Phe Asn Arg Tyr Phe Tyr Leu Leu Glu Asn
    130                 135                 140

Leu Ala Trp Val Lys Ser Tyr Asn Ile Cys Phe Glu Leu Glu Asp Cys
145                 150                 155                 160

Asn Glu Ile Phe Ile Gln Leu Phe Arg Thr Leu Phe Ser Val Ile Asn
                165                 170                 175

Asn Ser His Asn Lys Lys Val Gln Met His Met Leu Asp Leu Met Ser
            180                 185                 190

Ser Ile Ile Met Glu Gly Asp Gly Val Thr Gln Glu Leu Leu Asp Ser
        195                 200                 205

Ile Leu Ile Asn Leu Ile Pro Ala His Lys Asn Leu Asn Lys Gln Ser
    210                 215                 220

Phe Asp Leu Ala Lys Val Leu Leu Lys Arg Thr Val Gln Thr Ile Glu
225                 230                 235                 240

Ala Cys Ile Ala Asn Phe Phe Asn Gln Val Leu Val Leu Gly Arg Ser
                245                 250                 255

Ser Val Ser Asp Leu Ser Glu His Val Phe Asp Leu Ile Gln Glu Leu
            260                 265                 270

Phe Ala Ile Asp Pro His Leu Leu Leu Ser Val Met Pro Gln Leu Glu
        275                 280                 285

Phe Lys Leu Lys Ser Asn Asp Gly Glu Glu Arg Leu Ala Val Val Arg
    290                 295                 300

Leu Leu Ala Lys Leu Phe Gly Ser Lys Asp Ser Asp Leu Ala Thr Gln
305                 310                 315                 320

Asn Arg Pro Leu Trp Gln Cys Phe Leu Gly Arg Phe Asn Asp Ile His
                325                 330                 335

Val Pro Val Arg Leu Glu Ser Val Lys Phe Ala Ser His Cys Leu Met
            340                 345                 350

Asn His Pro Asp Leu Ala Lys Asp Leu Thr Glu Tyr Leu Lys Val Arg
        355                 360                 365

Ser His Asp Pro Glu Glu Ala Ile Arg His Asp Val Ile Val Thr Ile
    370                 375                 380

Ile Thr Ala Ala Lys Arg Asp Leu Ala Leu Val Asn Asp Gln Leu Leu
385                 390                 395                 400

Gly Phe Val Arg Glu Arg Thr Leu Asp Lys Arg Trp Arg Val Arg Lys
                405                 410                 415

Glu Ala Met Met Gly Leu Ala Gln Leu Tyr Lys Lys Tyr Cys Leu His
            420                 425                 430

Gly Glu Ala Gly Lys Glu Ala Ala Glu Lys Val Ser Trp Ile Lys Asp
        435                 440                 445
```

```
Lys Leu Leu His Ile Tyr Tyr Gln Asn Ser Ile Asp Asp Lys Leu Leu
    450                 455                 460

Val Glu Lys Ile Phe Ala Gln Tyr Leu Val Pro His Asn Leu Glu Thr
465                 470                 475                 480

Glu Glu Arg Met Lys Cys Leu Tyr Tyr Leu Tyr Ala Ser Leu Asp Pro
                485                 490                 495

Asn Ala Val Lys Ala Leu Asn Glu Met Trp Lys Cys Gln Asn Met Leu
            500                 505                 510

Arg Ser His Val Arg Glu Leu Leu Asp Leu His Lys Gln Pro Thr Ser
        515                 520                 525

Glu Ala Asn Cys Ser Ala Met Phe Gly Lys Leu Met Thr Ile Ala Lys
    530                 535                 540

Asn Leu Pro Asp Pro Gly Lys Ala Gln Asp Phe Val Lys Lys Phe Asn
545                 550                 555                 560

Gln Val Leu Gly Asp Asp Glu Lys Leu Arg Ser Gln Leu Glu Leu Leu
                565                 570                 575

Ile Ser Pro Thr Cys Ser Cys Lys Gln Ala Asp Ile Cys Val Arg Glu
            580                 585                 590

Ile Ala Arg Lys Leu Ala Asn Pro Lys Gln Pro Thr Asn Pro Phe Leu
        595                 600                 605

Glu Met Val Lys Phe Leu Leu Glu Arg Ile Ala Pro Val His Ile Asp
    610                 615                 620

Ser Glu Ala Ile Ser Ala Leu Val Lys Leu Met Asn Lys Ser Ile Glu
625                 630                 635                 640

Gly Thr Ala Asp Asp Glu Glu Glu Gly Val Ser Pro Asp Thr Ala Ile
                645                 650                 655

Arg Ser Gly Leu Glu Leu Leu Lys Val Leu Ser Phe Thr His Pro Thr
            660                 665                 670

Ser Phe His Ser Ala Glu Thr Tyr Glu Ser Leu Leu Gln Cys Leu Arg
        675                 680                 685

Met Glu Asp Asp Lys Val Ala Glu Ala Ala Ile Gln Ile Phe Arg Asn
    690                 695                 700

Thr Gly His Lys Ile Glu Thr Asp Leu Pro Gln Ile Arg Ser Thr Leu
705                 710                 715                 720

Ile Pro Ile Leu His Gln Lys Ala Lys Arg Gly Thr Pro His Gln Ala
                725                 730                 735

Lys Gln Ala Val His Cys Ile His Ala Ile Phe Thr Asn Lys Glu Val
            740                 745                 750

Gln Leu Ala Gln Ile Phe Glu Pro Leu Ser Arg Ser Leu Asn Ala Asp
        755                 760                 765

Val Pro Glu Gln Leu Ile Thr Pro Leu Val Ser Leu Gly His Ile Ser
    770                 775                 780

Met Leu Ala Pro Asp Gln Phe Ala Ser Pro Met Lys Ser Val Val Ala
785                 790                 795                 800

Asn Phe Ile Val Lys Asp Leu Leu Met Asn Asp Arg Ser Thr Gly Glu
                805                 810                 815

Lys Asn Gly Lys Leu Trp Ser Pro Asp Glu Glu Val Ser Pro Glu Val
            820                 825                 830

Leu Ala Lys Val Gln Ala Ile Lys Leu Leu Val Arg Trp Leu Leu Gly
        835                 840                 845

Met Lys Asn Asn Gln Ser Lys Ser Ala Asn Ser Thr Leu Arg Leu Leu
    850                 855                 860
```

```
Ser Ala Met Leu Val Ser Glu Gly Asp Leu Thr Glu Gln Lys Arg Ile
865                 870                 875                 880

Ser Lys Ser Asp Met Ser Arg Leu Arg Leu Ala Ala Gly Ser Ala Ile
                885                 890                 895

Met Lys Leu Ala Gln Glu Pro Cys Tyr His Glu Ile Ile Thr Pro Glu
            900                 905                 910

Gln Phe Gln Leu Cys Ala Leu Val Ile Asn Asp Glu Cys Tyr Gln Val
        915                 920                 925

Arg Gln Ile Phe Ala Gln Lys Leu His Lys Ala Leu Val Lys Leu Leu
    930                 935                 940

Leu Pro Leu Glu Tyr Met Ala Ile Phe Ala Leu Cys Ala Lys Asp Pro
945                 950                 955                 960

Val Lys Glu Arg Arg Ala His Ala Arg Gln Cys Leu Leu Lys Asn Ile
                965                 970                 975

Ser Ile Arg Arg Glu Tyr Ile Lys Gln Asn Pro Met Ala Thr Glu Lys
            980                 985                 990

Leu Leu Ser Leu Leu Pro Glu Tyr  Val Val Pro Tyr Met  Ile His Leu
        995                 1000                1005

Leu Ala  His Asp Pro Asp Phe  Thr Arg Ser Gln Asp  Val Asp Gln
    1010                 1015                 1020

Leu Arg  Asp Ile Lys Glu Cys  Leu Trp Phe Met Leu  Glu Val Leu
    1025                 1030                 1035

Met Thr  Lys Asn Glu Asn Asn  Ser His Ala Phe Met  Lys Lys Met
    1040                 1045                 1050

Ala Glu  Asn Ile Lys Leu Thr  Arg Asp Ala Gln Ser  Pro Asp Glu
    1055                 1060                 1065

Ser Lys  Thr Asn Glu Lys Leu  Tyr Thr Val Cys Asp  Val Ala Leu
    1070                 1075                 1080

Cys Val  Ile Asn Ser Lys Ser  Ala Leu Cys Asn Ala  Asp Ser Pro
    1085                 1090                 1095

Lys Asp  Pro Val Leu Pro Met  Lys Phe Phe Thr Gln  Pro Glu Lys
    1100                 1105                 1110

Asp Phe  Cys Asn Asp Lys Ser  Tyr Ile Ser Glu Glu  Thr Arg Val
    1115                 1120                 1125

Leu Leu  Leu Thr Gly Lys Pro  Lys Pro Ala Gly Val  Leu Gly Ala
    1130                 1135                 1140

Val Asn  Lys Pro Leu Ser Ala  Thr Gly Arg Lys Pro  Tyr Val Arg
    1145                 1150                 1155

Ser Thr  Gly Thr Glu Thr Gly  Ser Asn Ile Asn Val  Asn Ser Glu
    1160                 1165                 1170

Leu Asn  Pro Ser Thr Gly Asn  Arg Ser Arg Glu Gln  Ser Ser Glu
    1175                 1180                 1185

Ala Ala  Glu Thr Gly Val Ser  Glu Asn Glu Glu Asn  Pro Val Arg
    1190                 1195                 1200

Ile Ile  Ser Val Thr Pro Val  Lys Asn Ile Asp Pro  Val Lys Asn
    1205                 1210                 1215

Lys Glu  Ile Asn Ser Asp Gln  Ala Thr Gln Gly Asn  Ile Ser Ser
    1220                 1225                 1230

Asp Arg  Gly Lys Lys Arg Thr  Val Thr Ala Ala Gly  Ala Glu Asn
    1235                 1240                 1245

Ile Gln  Gln Lys Thr Asp Glu  Lys Val Asp Glu Ser  Gly Pro Pro
    1250                 1255                 1260

Ala Pro  Ser Lys Pro Arg Arg  Gly Arg Arg Pro Lys  Ser Glu Ser
```

-continued

```
    1265                1270                1275

Gln Gly  Asn Ala Thr Lys Asn  Asp Asp Leu Asn Lys  Pro Ile Asn
    1280                1285                1290

Lys Gly  Arg Lys Arg Ala Ala  Val Gly Gln Glu Ser  Pro Gly Gly
    1295                1300                1305

Leu Glu  Ala Gly Asn Ala Lys  Ala Pro Lys Leu Gln  Asp Leu Ala
    1310                1315                1320

Lys Lys  Ala Ala Pro Ala Glu  Arg Gln Ile Asp Leu  Gln Arg
    1325                1330                1335
```